(12) United States Patent
Oomori et al.

(10) Patent No.: US 12,011,225 B2
(45) Date of Patent: Jun. 18, 2024

(54) SLIT LAMP MICROSCOPE AND OPHTHALMIC SYSTEM

(71) Applicant: Topcon Corporation, Tokyo (JP)

(72) Inventors: Kazuhiro Oomori, Tokyo (JP); Yasufumi Fukuma, Wako (JP); Hitoshi Shimizu, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 638 days.

(21) Appl. No.: 17/251,210

(22) PCT Filed: Jun. 12, 2019

(86) PCT No.: PCT/JP2019/023199
§ 371 (c)(1),
(2) Date: Dec. 11, 2020

(87) PCT Pub. No.: WO2019/240148
PCT Pub. Date: Dec. 19, 2019

(65) Prior Publication Data
US 2021/0153740 A1    May 27, 2021

(30) Foreign Application Priority Data

Jun. 13, 2018 (JP) ................................ 2018-112893

(51) Int. Cl.
*A61B 3/135* (2006.01)
*A61B 3/00* (2006.01)
*A61B 3/14* (2006.01)

(52) U.S. Cl.
CPC ............ *A61B 3/135* (2013.01); *A61B 3/0008* (2013.01); *A61B 3/14* (2013.01)

(58) Field of Classification Search
CPC ......... A61B 3/135; A61B 3/0008; A61B 3/14; A61B 3/024; A61B 3/12
(Continued)

(56) References Cited

U.S. PATENT DOCUMENTS 5,512,965 A    4/1996 Snook
5,735,283 A    4/1998 Snook
(Continued)

FOREIGN PATENT DOCUMENTS

EP    3491996 A1      6/2019
EP    3888527 A1 * 10/2021 ........... A61B 3/0025
(Continued)

OTHER PUBLICATIONS

Japanese Office Action dated Jul. 12, 2022 in corresponding Japanese Patent Application No. 2018-112893 (with machine-generated English Translation), 8 pages.
(Continued)

*Primary Examiner* — Mohammed A Hasan
(74) *Attorney, Agent, or Firm* — XSENSUS LLP

(57) ABSTRACT

A slit lamp microscope of some embodiment examples includes an illumination system, photography system, and movement mechanism. The illumination system projects slit light onto an anterior segment of an eye. The photography system includes an optical system and image sensor. The optical system directs light coming from the anterior segment onto which the slit light is being projected. The image sensor includes a light detecting plane that receives the light directed by the optical system. The movement mechanism moves the illumination and photography systems. The subject plane along the optical axis of the illumination system, the optical system, and the light detecting plane satisfy the Scheimpflug condition. The photography system acquires a plurality of images of the anterior segment by performing repetitive photography in parallel with movement of the illumination and photography systems performed by the movement mechanism.

14 Claims, 35 Drawing Sheets

(58) Field of Classification Search
USPC .......................................................... 351/214
See application file for complete search history.

(56) References Cited

U.S. PATENT DOCUMENTS

| | | | |
|---|---|---|---|
| 2002/0060778 A1* | 5/2002 | Su ........................ | A61B 3/154 351/206 |
| 2004/0119943 A1 | 6/2004 | Rathjen | |
| 2005/0084179 A1 | 4/2005 | Hanna et al. | |
| 2009/0303437 A1 | 12/2009 | Cattin-Liebl | |
| 2010/0097573 A1 | 4/2010 | Verdooner et al. | |
| 2010/0142780 A1 | 6/2010 | Yasuno et al. | |
| 2013/0321770 A1 | 12/2013 | Mizuno | |
| 2014/0228681 A1 | 8/2014 | Jia et al. | |
| 2015/0085252 A1 | 3/2015 | Fujimura et al. | |
| 2015/0265762 A1* | 9/2015 | Friedman ............. | A61K 49/006 600/431 |
| 2016/0029887 A1 | 2/2016 | Su | |
| 2016/0295109 A1 | 10/2016 | Henriksen | |
| 2016/0345822 A1 | 12/2016 | Fujimura et al. | |
| 2017/0262163 A1 | 9/2017 | Nimura | |
| 2018/0153399 A1 | 6/2018 | Fink et al. | |
| 2018/0242862 A1 | 8/2018 | Jia et al. | |
| 2021/0153740 A1 | 5/2021 | Oomori et al. | |

FOREIGN PATENT DOCUMENTS

| | | | | |
|---|---|---|---|---|
| EP | 3888529 A1 * | 10/2021 | ........... | A61B 3/0008 |
| JP | H11-239565 A | 9/1999 | | |
| JP | 3013356 B2 | 2/2000 | | |
| JP | 2000-116732 A | 4/2000 | | |
| JP | 2003-111728 A | 4/2003 | | |
| JP | 2005-028097 A | 2/2005 | | |
| JP | 2007-130403 A | 5/2007 | | |
| JP | 2008-011878 A | 1/2008 | | |
| JP | 2008-284273 A | 11/2008 | | |
| JP | 2012-055337 A | 3/2012 | | |
| JP | 2012-505729 A | 3/2012 | | |
| JP | 2013-248376 A | 12/2013 | | |
| JP | 2014-193410 A | 10/2014 | | |
| JP | 2015-511146 A | 4/2015 | | |
| JP | 2016-159073 A | 9/2016 | | |
| JP | 2016-179004 A | 10/2016 | | |
| JP | 2016-209453 A | 12/2016 | | |
| JP | 2017-501005 A | 1/2017 | | |
| JP | 2017-148241 A | 8/2017 | | |
| JP | 2017-163465 A | 9/2017 | | |
| JP | 2019-213729 A | 12/2019 | | |
| WO | WO-2010040484 A1 * | 4/2010 | ............ | A61B 3/135 |
| WO | 2018/021561 A1 | 2/2018 | | |

OTHER PUBLICATIONS

Extended European search report dated Feb. 1, 2022, in corresponding European patent Application No. 19818732.0, 8 pages.
Cristina M Oliveira et al., "Corneal imaging with slit-scanning and Scheimpflug imaging techniques", Optometry, Clinical and Experimental Optometry, vol. 94, No. 1, Jan. 2011, pp. 33-42.
Office Action dated Feb. 14, 2023 in corresponding Japanese Patent Application No. 2018-112893 and computer-generated English translation thereof, 9 pages.
International Search Report and Written Opinion dated Sep. 3, 2019, received for PCT Application No. PCT/JP2019/023199, Filed on Jun. 12, 2019, 9 pages including English Translation.
Office Action dated Nov. 21, 2023 in Japanese Patent Application No. 2023-057833 with computer-generated English translation thereof.
Communication pursuant to Article 94(3) EPC issued Dec. 18, 2023, in corresponding European Patent Application No. 19818732.0, 8 pages.
Japan Office Action issued Feb. 20, 2024, in corresponding Japanese Patent Application No. 2023-121910, 9 pages.
Chinese Office Action issued Mar. 20, 2024, in corresponding Chinese Patent Application No. 201980048321.X, 26 pages.

* cited by examiner

SLIT LAMP MICROSCOPE AND OPHTHALMIC SYSTEM

CROSS-REFERENCE TO RELATED APPLICATIONS

This application is a national stage (under 35 U.S.C. 371) of International Patent Application No. PCT/JP2019/023199, filed Jun. 12, 2019, claiming priority to Japanese Patent Application No. 2018-112893, filed Jun. 13, 2018, both of which are herein incorporated by reference in their entirety.

FIELD

The present disclosure relates to a slit lamp microscope and an ophthalmic system.

BACKGROUND

Diagnostic imaging serves an important role in the field of ophthalmology. Diagnostic imaging uses various kinds of ophthalmic imaging apparatuses. Examples of ophthalmic imaging apparatuses include a slit lamp microscope, a fundus camera, a scanning laser ophthalmoscope (SLO), an optical coherence tomography (OCT) apparatus, and the like. In addition, various kinds of ophthalmic examination apparatuses and ophthalmic measurement apparatuses, such as a refractometer, a keratometer, a tonometer, a specular microscope, a wave front analyzer, and a micro perimeter, are equipped with the function of imaging anterior eye segment, eye fundus, etc.

A slit lamp microscope is one of the most widely and frequently utilized apparatuses among various kinds of ophthalmic apparatuses. A slit lamp microscope is an ophthalmic apparatus for illuminating a subject's eye with slit light and observing and/or photographing the illuminated cross section from an oblique position with a microscope (see, for example, Patent Documents 1 and 2).

A slit lamp microscope is utilized in general for observation and diagnosis of anterior segments such as corneas or crystalline lenses. For example, a doctor observes an entire diagnostic site while moving the focal position and the area illuminated by the slit light to determine the presence or absence of abnormality. Further, a slit lamp microscope may also be used for prescription of vision correction devices such as for checking of fitting states of contact lenses. Furthermore, those who have qualifications other than medical doctors, such as optometrists, and clerks in optician's stores may use slit lamp microscopes for the purpose of screening for eye diseases or the like.

Incidentally, research and development related to telemedicine technology is showing progress with recent advances in information and communication technology. Telemedicine is the act of using information technology such as the Internet to provide medical care (diagnosis, treatment) to a patient in a remote place. Patent Documents 3 and 4 disclose a technique for operating a slit lamp microscope from a remote location.

However, acquisition of an adequate images using a slit lamp microscope requires fine and complicated operations such as illumination angle adjustment and photographing angle adjustment. The techniques disclosed in Patent Documents 3 and 4 require an examiner, who is at a remote place, to conduct operations that are difficult even in the case where the examiner is observing the eyes of a subject face to face. This causes problems such as the duration of examination becoming long, and being unable to obtain an adequate image.

In addition, while slit lamp microscopes are effective for screening and other examinations as described above, the current situation is that there is a shortage of persons who have expertise in this equipment, and it is not possible to provide high quality examinations to many people.

Japanese Unexamined Patent Application Publication No. 2016-159073 is cited as the PATENT DOCUMENT 1, Japanese Unexamined Patent Application Publication No. 2016-179004 is cited as the PATENT DOCUMENT 2, Japanese Unexamined Patent Application Publication No. 2000-116732 is cited as the PATENT DOCUMENT 3, and Japanese Unexamined Patent Application Publication No. 2008-284273 is cited as the PATENT DOCUMENT 4 in the present specification.

BRIEF SUMMARY

An object of the present disclosure is to make it possible to widely provide high quality slit lamp microscope examinations.

The first aspect of some embodiment examples is a slit lamp microscope comprising: an illumination system configured to project slit light onto an anterior segment of an eye; a photography system including an optical system and an image sensor, the optical system being configured to direct light coming from the anterior segment onto which the slit light is being projected, and the image sensor including a light detecting plane that receives the light directed by the optical system; and a movement mechanism configured to move the illumination system and the photography system, wherein a subject plane along an optical axis of the illumination system, the optical system, and the light detecting plane satisfy a Scheimpflug condition, and the photography system acquires a plurality of images of the anterior segment by performing repetitive photography in parallel with movement of the illumination system and the photography system performed by the movement mechanism.

The second aspect of some embodiment examples is the slit lamp microscope of the first aspect, wherein the photography system includes a first photography system and a second photography system, wherein the first photography system includes a first optical system and a first image sensor, the first optical system being configured to direct the light coming from the anterior segment onto which the slit light is being projected, and the first image sensor including a first light detecting plane that receives the light directed by the first optical system, wherein the first photography system acquires a first image group by performing repetitive photography in parallel with the movement, and the second photography system includes a second optical system and a second image sensor, the second optical system being configured to direct the light coming from the anterior segment onto which the slit light is being projected, and the second image sensor including a second light detecting plane that receives the light directed by the second optical system, wherein the second photography system acquires a second image group by performing repetitive photography in parallel with the movement, wherein an orientation of an optical axis of the first optical system and an orientation of an optical axis of the second optical system are different from each other, and the subject plane, the first optical system, and the first light detecting plane satisfy the Scheimpflug condition, and the subject plane, the second optical system, and the second light detecting plane satisfy the Scheimpflug condition.

The third aspect of some embodiment examples is the slit lamp microscope of the second aspect, wherein the optical axis of the first optical system and the optical axis of the second optical system are tilted in mutually opposite directions with respect to the optical axis of the illumination system, and the slit lamp microscope further comprising an image selecting processor configured to judge whether at least one of two images substantially simultaneously acquired by the first photography system and the second photography system contains an artifact, and select a first image of the two images if a second image of the two images is judged to contain the artifact.

The fourth aspect of some embodiment examples is the slit lamp microscope of the third aspect, further comprising a three dimensional image constructing processor configured to construct a three dimensional image based on an image group including images selected from the first image group and the second image group by the image selecting processor.

The fifth aspect of some embodiment examples is the slit lamp microscope of the second aspect, further comprising an artifact eliminating processor configured to judge whether at least one of two images substantially simultaneously acquired by the first photography system and the second photography system contains an artifact by comparing the two images, and eliminate the artifact if the at least one of the two images is judged to contain the artifact.

The sixth aspect of some embodiment examples is the slit lamp microscope of the fifth aspect, further comprising a three dimensional image constructing processor configured to construct a three dimensional image based on an image group including an image from which the artifact is eliminated by the artifact eliminating processor.

The seventh aspect of some embodiment examples is the slit lamp microscope of the first aspect, further comprising a three dimensional image constructing processor configured to construct a three dimensional image based on the plurality of images acquired by the photography system.

The eighth aspect of some embodiment examples is the slit lamp microscope of any of the fourth, sixth and seventh aspects, wherein the movement mechanism includes a rotation mechanism configured to integrally rotate the illumination system and the photography system about the optical axis of the illumination system, the photography system acquires the plurality of images when the illumination system and the photography system are arranged in a first rotation position, the photography system acquires an image of the anterior segment onto which the slit light is being projected by the illumination system when the illumination system and the photography system are arranged in a second rotation position different from the first rotation position, and the three dimensional image constructing processor includes an image position determining processor configured to determine relative positions of the plurality of images based on the image acquired in the second rotation position.

The ninth aspect of some embodiment examples is the slit lamp microscope of any of the fourth, and sixth to eighth aspects, wherein the three dimensional image constructing processor includes: an image region extracting processor configured to extract an image region corresponding to a projection region of the slit light from each of the plurality of images; and an image composing processor configured to construct a three dimensional image by composing a plurality of image regions extracted respectively from the plurality of images by the image region extracting processor.

The tenth aspect of some embodiment examples is the slit lamp microscope of the ninth aspect, wherein the image region extracting processor extracts an image region corresponding to both the projection region of the slit light and a predetermined site of the anterior segment from each of the plurality of images.

The eleventh aspect of some embodiment examples is the slit lamp microscope of the tenth aspect, wherein the predetermined site is a region defined by an anterior corneal surface and a posterior crystalline lens surface.

The twelfth aspect of some embodiment examples is the slit lamp microscope of any of the fourth, sixth to eleventh aspects, further comprising a rendering processor configured to apply rendering to the three dimensional image to construct a rendered image.

The thirteenth aspect of some embodiment examples is the slit lamp microscope of the twelfth aspect, wherein when a cross section of the three dimensional image is designated, the rendering processor cuts the three dimensional image at the cross section to construct a three dimensional partial image.

The fourteenth aspect of some embodiment examples is the slit lamp microscope of the twelfth aspect, wherein when a cross section of the three dimensional image is designated, the rendering processor constructs a two dimensional partial image representing the cross section.

The fifteenth aspect of some embodiment examples is the slit lamp microscope of the twelfth aspect, wherein when a slice of the three dimensional image is designated, the rendering processor constructs a three dimensional slice image corresponding to the slice.

The sixteenth aspect of some embodiment examples is the slit lamp microscope of any of the first to fifteenth aspects, further comprising a distortion correcting processor configured to apply, to at least one of the plurality of images, processing to correct distortion caused by an optical axis angle that is an angle formed by the optical axis of the illumination system and an optical axis of the photography system.

The seventeenth aspect of some embodiment examples is the slit lamp microscope of the sixteenth aspect, wherein an optical axis of the optical system of the photography system is tilted, against the optical axis of the illumination system, in a third direction orthogonal to both a first direction along the optical axis of the illumination system and a second direction along a longitudinal direction of the slit light, and the distortion correcting processor performs processing to correct distortion in a plane spanned by both the first direction and the second direction.

The eighteenth aspect of some embodiment examples is the slit lamp microscope of the sixteenth or seventeenth aspect, wherein the distortion correcting processor stores a correction factor determined based on a predetermined reference angle and the optical axis angle in advance, and performs the processing to correct the distortion based on the correction factor.

The nineteenth aspect of some embodiment examples is the slit lamp microscope of any of the first to eighteenth aspects, further comprising a first measuring processor configured to calculate a predetermined measurement value by analyzing at least one of the plurality of images acquired by the photography system.

The twentieth aspect of some embodiment examples is the slit lamp microscope of any of the fourth, sixth to fifteenth aspects, further comprising a second measuring processor configured to calculate a predetermined measurement value by analyzing the three dimensional image constructed by the three dimensional image constructing processor.

The twenty first aspect of some embodiment examples is the slit lamp microscope of any of the first to twentieth aspects, wherein the illumination system and the photography system are configured in such a manner that at least a region defined by an anterior corneal surface and a posterior crystalline lens surface is in focus of the photography system.

The twenty second aspect of some embodiment examples is the slit lamp microscope of any of the first to twenty first aspects, wherein the illumination system projects the slit light whose longitudinal direction corresponds to a body axis direction of a subject, onto the anterior segment, and the movement mechanism moves the illumination system and the photography system in a direction orthogonal to the body axis direction.

The twenty third aspect of some embodiment examples is the slit lamp microscope of the twenty second aspect, wherein a length of the slit light is equal to or greater than a corneal diameter in the body axis direction, and a distance of the movement of the illumination system and the photography system performed by the movement mechanism is equal to or greater than a corneal diameter in the direction orthogonal to the body axis direction.

The twenty fourth aspect of some embodiment examples is the slit lamp microscope of any of the first to twenty third aspects, wherein the optical system of the photography system includes: a reflector configured to reflect the light coming from the anterior segment onto which the slit light is being projected and traveling in a direction away from the optical axis of the illumination system, toward a direction approaching the optical axis of the illumination system; and at least one lens configured to form an image of the light reflected by the reflector on the light detecting plane.

The twenty fifth aspect of some embodiment examples is the slit lamp microscope of any of the first to twenty fourth aspects, further comprising a moving image photography system configured to acquire a moving image of the anterior segment from a fixed position in parallel with acquisition of the plurality of images by the photography system.

The twenty sixth aspect of some embodiment examples is the slit lamp microscope of the twenty fifth aspect, further comprising a motion detecting processor configured to detect motion of the eye by analyzing the moving image acquired by the moving image photography system.

The twenty seventh aspect of some embodiment examples is the slit lamp microscope of the twenty sixth aspect, further comprising a movement controller configured to control the movement mechanism based on an output from the motion detecting processor.

The twenty eighth aspect of some embodiment examples is the slit lamp microscope of any of the first to twenty seventh aspects, further comprising a communication device configured to transmit an acquired image of the anterior segment to an information processing apparatus.

The twenty ninth aspect of some embodiment examples is an ophthalmic system comprising a slit lamp microscope, and an information processing apparatus that is connected to the slit lamp microscope via a communication channel and processes an image of an anterior segment of an eye acquired by the slit lamp microscope, wherein the slit lamp microscope includes an illumination system configured to project slit light onto the anterior segment of the eye; a photography system including an optical system and an image sensor, the optical system being configured to direct light coming from the anterior segment onto which the slit light is being projected, and the image sensor including a light detecting plane that receives the light directed by the optical system; and a movement mechanism configured to move the illumination system and the photography system, wherein a subject plane along an optical axis of the illumination system, the optical system, and the light detecting plane satisfy a Scheimpflug condition, and the photography system acquires a plurality of images of the anterior segment by performing repetitive photography in parallel with movement of the illumination system and the photography system performed by the movement mechanism.

The thirtieth aspect of some embodiment examples is the ophthalmic system of the twenty ninth aspect, wherein the photography system of the slit lamp microscope includes a first photography system and a second photography system, wherein the first photography system includes a first optical system and a first image sensor, the first optical system being configured to direct the light coming from the anterior segment onto which the slit light is being projected, and the first image sensor including a first light detecting plane that receives the light directed by the first optical system, wherein the first photography system acquires a first image group by performing repetitive photography in parallel with the movement, and the second photography system includes a second optical system and a second image sensor, the second optical system being configured to direct the light coming from the anterior segment onto which the slit light is being projected, and the second image sensor including a second light detecting plane that receives the light directed by the second optical system, wherein the second photography system acquires a second image group by performing repetitive photography in parallel with the movement, wherein an orientation of an optical axis of the first optical system and an orientation of an optical axis of the second optical system are different from each other, and the subject plane, the first optical system, and the first light detecting plane satisfy the Scheimpflug condition, and the subject plane, the second optical system, and the second light detecting plane satisfy the Scheimpflug condition.

The thirty first aspect of some embodiment examples is the ophthalmic system of the thirtieth aspect, wherein the optical axis of the first optical system and the optical axis of the second optical system are tilted in mutually opposite directions with respect to the optical axis of the illumination system, and the information processing apparatus includes an image selecting processor configured to judge whether at least one of two images substantially simultaneously acquired by the first photography system and the second photography system contains an artifact, and select a first image of the two images if a second image of the two images is judged to contain the artifact.

The thirty second aspect of some embodiment examples is the ophthalmic system of the thirty first aspect, wherein the information processing apparatus includes a three dimensional image constructing processor configured to construct a three dimensional image based on an image group including images selected from the first image group and the second image group by the image selecting processor.

The thirty third aspect of some embodiment examples is the ophthalmic system of the thirtieth aspect, wherein the information processing apparatus includes an artifact eliminating processor configured to judge whether at least one of two images substantially simultaneously acquired by the first photography system and the second photography system contains an artifact by comparing the two images, and eliminate the artifact if the at least one of the two images is judged to contain the artifact.

The thirty fourth aspect of some embodiment examples is the ophthalmic system of the thirty third aspect, wherein the information processing apparatus includes a three dimensional image constructing processor configured to construct a three dimensional image based on an image group including an image from which the artifact is eliminated by the artifact eliminating processor.

The thirty fifth aspect of some embodiment examples is the ophthalmic system of the twenty ninth aspect, wherein the information processing apparatus includes a three dimensional image constructing processor configured to construct a three dimensional image based on the plurality of images acquired by the photography system.

The thirty sixth aspect of some embodiment examples is the ophthalmic system of the thirty second, thirty fourth, and thirty fifth aspects, wherein the movement mechanism includes a rotation mechanism configured to integrally rotate the illumination system and the photography system about the optical axis of the illumination system, the photography system acquires the plurality of images when the illumination system and the photography system are arranged in a first rotation position, the photography system acquires an image of the anterior segment onto which the slit light is being projected by the illumination system when the illumination system and the photography system are arranged in a second rotation position different from the first rotation position, and the three dimensional image constructing processor includes an image position determining processor configured to determine relative positions of the plurality of images based on the image acquired in the second rotation position.

The thirty seventh aspect of some embodiment examples is the ophthalmic system of the thirty second, thirty fourth to thirty sixth aspects, wherein the three dimensional image constructing processor includes: an image region extracting processor configured to extract an image region corresponding to a projection region of the slit light from each of the plurality of images; and an image composing processor configured to construct a three dimensional image by composing a plurality of image regions extracted respectively from the plurality of images by the image region extracting processor.

The thirty eighth aspect of some embodiment examples is the ophthalmic system of the thirty seventh aspect, wherein the image region extracting processor extracts an image region corresponding to both the projection region of the slit light and a predetermined site of the anterior segment from each of the plurality of images.

The thirty ninth aspect of some embodiment examples is the ophthalmic system of the thirty eighth aspect, wherein the predetermined site is a region defined by an anterior corneal surface and a posterior crystalline lens surface.

The fortieth aspect of some embodiment examples is the ophthalmic system of any of the thirty second, thirty fourth to thirty ninth aspects, wherein the information processing apparatus includes a rendering processor configured to apply rendering to the three dimensional image to construct a rendered image.

The forty first aspect of some embodiment examples is the ophthalmic system of the fortieth aspect, wherein when a cross section of the three dimensional image is designated, the rendering processor cuts the three dimensional image at the cross section to construct a three dimensional partial image.

The forty second aspect of some embodiment examples is the ophthalmic system of the fortieth aspect, wherein when a cross section of the three dimensional image is designated, the rendering processor constructs a two dimensional partial image representing the cross section.

The forty third aspect of some embodiment examples is the ophthalmic system of the fortieth aspect, wherein when a slice of the three dimensional image is designated, the rendering processor constructs a three dimensional slice image corresponding to the slice.

The forty fourth aspect of some embodiment examples is the ophthalmic system of any of the twenty ninth to forty third aspects, wherein the information processing apparatus includes a distortion correcting processor configured to apply, to at least one of the plurality of images, processing to correct distortion caused by an optical axis angle that is an angle formed by the optical axis of the illumination system and an optical axis of the photography system.

The forty fifth aspect of some embodiment examples is the ophthalmic system of the forty fourth aspect, wherein an optical axis of the optical system of the photography system is tilted, against the optical axis of the illumination system, in a third direction orthogonal to both a first direction along the optical axis of the illumination system and a second direction along a longitudinal direction of the slit light, and the distortion correcting processor performs processing to correct distortion in a plane spanned by both the first direction and the second direction.

The forty sixth aspect of some embodiment examples is the ophthalmic system of the forty fourth or forty fifth aspect, wherein the distortion correcting processor stores a correction factor determined based on a predetermined reference angle and the optical axis angle in advance, and performs the processing to correct the distortion based on the correction factor.

The forty seventh aspect of some embodiment examples is the ophthalmic system of any of the twenty ninth to forty sixth aspects, wherein the information processing apparatus includes a first measuring processor configured to calculate a predetermined measurement value by analyzing at least one of the plurality of images acquired by the photography system.

The forty eighth aspect of some embodiment examples is the ophthalmic system of any of the thirty second, thirty fourth to forty third aspects, wherein the information processing apparatus includes a second measuring processor configured to calculate a predetermined measurement value by analyzing the three dimensional image constructed by the three dimensional image constructing processor.

The forty ninth aspect of some embodiment examples is the ophthalmic system of any of the twenty ninth to forty eighth aspects, wherein the illumination system and the photography system are configured in such a manner that at least a region defined by an anterior corneal surface and a posterior crystalline lens surface is in focus of the photography system.

The fiftieth aspect of some embodiment examples is the ophthalmic system of any of the twenty ninth to forty ninth aspects, wherein the illumination system projects the slit light whose longitudinal direction corresponds to a body axis direction of a subject, onto the anterior segment, and the movement mechanism moves the illumination system and the photography system in a direction orthogonal to the body axis direction.

The fifty first aspect of some embodiment examples is the ophthalmic system of the fiftieth aspect, wherein a length of the slit light is equal to or greater than a corneal diameter in the body axis direction, and a distance of the movement of the illumination system and the photography system performed by the movement mechanism is equal to or greater than a corneal diameter in the direction orthogonal to the body axis direction.

The fifty second aspect of some embodiment examples is the ophthalmic system of any of the twenty ninth to fifty first aspects, wherein the optical system of the photography system includes: a reflector configured to reflect the light coming from the anterior segment onto which the slit light is being projected and traveling in a direction away from the optical axis of the illumination system, toward a direction approaching the optical axis of the illumination system; and at least one lens configured to form an image of the light reflected by the reflector on the light detecting plane.

The fifty third aspect of some embodiment examples is the ophthalmic system of any of the twenty ninth to fifty second aspects, wherein the slit lamp microscope further includes a moving image photography system configured to acquire a moving image of the anterior segment from a fixed position in parallel with acquisition of the plurality of images by the photography system.

The fifty fourth aspect of some embodiment examples is the ophthalmic system of the fifty third aspect, wherein the slit lamp microscope further includes a motion detecting processor configured to detect motion of the eye by analyzing the moving image acquired by the moving image photography system.

The fifty fifth aspect of some embodiment examples is the ophthalmic system of the fifty fourth aspect, wherein the slit lamp microscope further includes a movement controller configured to control the movement mechanism based on an output from the motion detecting processor.

According to some embodiment examples, a high quality slit lamp microscope examination can be widely provided.

DETAILED DESCRIPTION

Figure 1:
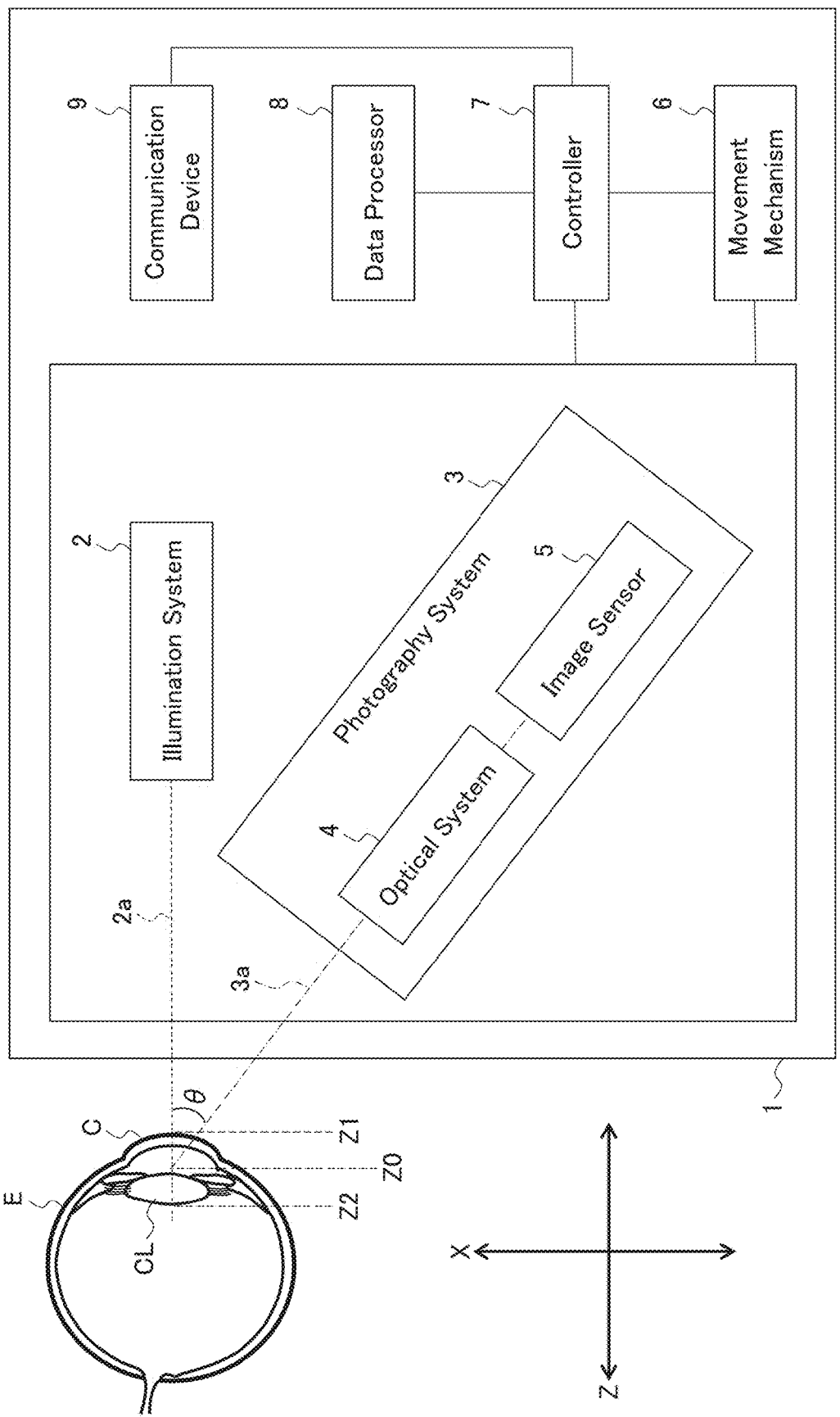
FIG. 1 is a schematic diagram illustrating the configuration of the slit lamp microscope according to the embodiment example.

Some embodiment examples will be described in detail with referring to the drawings. It should be noted that any known techniques or technologies such as any of the matters or items disclosed in the documents cited herein may be combined with the embodiment examples.

The slit lamp microscope according to some embodiment examples may be installed in a place such as an optician's store or a medical facility, or may be portable. The slit lamp microscope according to some embodiment examples is typically used in situations and/or environments where no technical experts relating to the apparatus is present nearby. Note that the slit lamp microscope according to some embodiment examples may be used in situations and/or environments where a technical expert is present, or in situations and/or environments where a technical expert can provide monitoring, give instructions, and/or conduct an apparatus operation, from a remote place.

The ophthalmic system according to some embodiment examples includes one or more slit lamp microscopes and one or more information processing apparatuses, and may be used for telemedicine, for example. The information processing apparatus is configured to receive and process an image acquired by the slit lamp microscope. The information processing apparatus may be capable of transmitting data to the slit lamp microscope and/or another information processing apparatus. The information processing apparatus may be utilized for, for example, image analysis, image processing, image interpretation, and the like.

In the case where the ophthalmic system of some embodiment examples is used for telemedicine, the interpretation of an image acquired by the slit lamp microscope is conducted by a person at a location distant from the facility where the slit lamp microscope is installed. The person who conducts the image interpretation is typically a doctor and is a technical expert relating to slit lamp microscopes. It is also possible to employ computer-based image interpretation support using information processing technology such as artificial intelligence, image analysis, or image processing.

Examples of the facility in which the slit lamp microscope is installed include an optician's store, an optometrist's office, a health facility, a medical institution, a health check and screening venue, a patient's home, a welfare facility, a public facility, a medical examination vehicle, and the like.

The slit lamp microscope according to some embodiment examples is an ophthalmic imaging apparatus having at least the function of a slit lamp microscope, and may be further provided with any other photographing or imaging functions performed by other modality apparatuses. Examples of such other modality apparatuses include a fundus camera, an SLO, an OCT apparatus, and the like. The slit lamp microscope according to some embodiment examples may further have any of the functions of measuring characteristics of eyes. Examples of such measurement functions include visual acuity measurement, refraction measurement, intraocular pressure measurement, corneal endothelial cell measurement, aberration measurement, visual field measurement, and the like. The slit lamp microscope according to some embodiment examples may further include application software for analyzing photographed images, measurement data, or the like. The slit lamp microscope according to some embodiment examples may further include any of the functions for treatment or surgery. Examples of such treatment or surgery includes photocoagulation treatment and photodynamic therapy.

Hereinafter, various embodiment examples will be described. Any two or more of these embodiment examples may be combined. Further, any modifications, such as addition or replacement, on the basis of any known technique or technology may be applied to any one of the embodiment examples or to any combination of two or more of the embodiment examples.

The "processor" as used in the embodiment examples described below is a circuit such as a central processing unit (CPU), a graphics processing unit (GPU), an application specific integrated circuit (ASIC), or a programmable logic device (PLD). Examples of the PLD include a simple programmable logic device (SPLD), a complex programmable logic device (CPLD), and a field programmable gate array (FPGA). For example, the processor loads and executes a program or data stored in a memory circuit or a storage for implementing the functions according to the corresponding embodiment example.

First Embodiment Example

FIG. 1 shows an example of the slit lamp microscope according to the first embodiment example.

The slit lamp microscope 1 may be used for photographing the anterior segment of the subject's eye E, and includes the illumination system 2, the photography system 3, the movement mechanism 6, the controller 7, the data processor 8, and the communication device 9. The cornea of the subject's eye E is denoted by the reference character C, and the crystalline lens is denoted by the reference character CL.

The slit lamp microscope 1 may be a single apparatus, or may also be a system that includes two or more apparatuses. In the case where the slit lamp microscope 1 is configured as a system, the slit lamp microscope 1 may include a main apparatus, a computer, and a communication device. Here, the main apparatus may include the illumination system 2, the photography system 3, and the movement mechanism 6, the computer may include the controller 7, the data processor 8, and the communication device 9, and the communication device may perform communication between the main apparatus and the computer. The computer may be installed together with the main apparatus, for example, or may also be installed on a network.

[Illumination System 2]

The illumination system 2 projects slit light onto the anterior segment of the subject's eye E. The reference character 2a denotes the optical axis of the illumination system 2 that is referred to as the illumination optical axis. The illumination system 2 may have the same or similar configuration as or to the illumination system of a conventional slit lamp microscope. For example, the illumination system 2 includes an illumination light source, a positive lens, a slit forming member, and an objective lens in the order from the side far from the subject's eye E (not shown in the drawings).

The illumination light source outputs (emits) illumination light. The illumination system 2 may include a plurality of illumination light sources. For example, the illumination system 2 may include both an illumination light source that outputs continuous light or steady light, and an illumination light source that outputs flash light. Further, the illumination system 2 may include both an illumination light source for anterior segment illumination and an illumination light source for posterior segment illumination. Furthermore, the illumination system 2 may include two or more illumination light sources with mutually different output wavelengths. A typical example of the illumination system 2 includes a visible light source as an illumination light source. The illumination system 2 may also include an infrared light source. The illumination light output from the illumination light source passes through the positive lens and is projected onto the slit forming member.

The slit forming member passes a part of the illumination light to generate slit light. A typical example of the slit forming member has a pair of slit blades. The width of the region through which the illumination light passes is changed by changing the interval between the slit blades, and the width of the slit light is changed accordingly. The region through which the illumination light passes is referred to as a slit, and the interval between the slit blades is referred to as a slit width. Further, the slit forming member may be configured to be capable of changing the length of the slit light. The length of the slit light is a size of a cross section of the slit light along the direction orthogonal to the cross sectional width direction of the slit light. Here, the cross sectional width direction corresponds to the slit width. The width of the slit light and the length of the slit light are typically represented as the size of a projected image on the anterior segment formed by the slit light.

The slit light generated by the slit forming member is refracted by the objective lens and is projected onto the anterior segment of the subject's eye E.

The illumination system 2 may further include a focus mechanism configured for changing the focal position of the slit light. The focus mechanism may be configured to move the objective lens along the illumination optical axis 2a, for example. The movement of the objective lens may be carried out automatically and/or manually. Another focus mechanism may be configured to change the focal position of the slit light by: preparing and disposing a focusing lens at a position in the illumination optical axis 2a between the objective lens and the slit forming member; and moving the focusing lens along the illumination optical axis 2a.

Note that FIG. 1 is a top view. As shown in FIG. 1, the direction along the axis of the subject's eye E is defined as the Z direction in the present embodiment example. Of the directions orthogonal to the Z direction, the left-right direction (or, the lateral direction) for the subject is defined as the X direction. The direction orthogonal to both the X direction and the Z direction is defined as the Y direction. Typically, the X direction is the direction from one of the left eye and the right eye toward the other, and the Y direction is the direction parallel to the body axis of the subject (body axis direction). Further, the slit lamp microscope 1 according to the present embodiment example may perform alignment in such a manner that the illumination optical axis 2a coincides with the axis of the subject's eye E. In a broader sense, the alignment is carried out in such a manner that the illumination optical axis 2a is arranged in parallel with the axis of the subject's eye E. A description of the alignment will be given later.

[Photography System 3]

The photography system 3 is configured to perform photography of the anterior segment while the slit light from the illumination system 2 is being projected onto the anterior segment. The reference character 3a denotes the optical axis of the photography system 3 that is referred to as the photography optical axis. The photography system 3 of the present embodiment example includes the optical system 4 and the image sensor 5.

The optical system 4 is configured to direct light coming from the anterior segment of the subject's eye E onto which the slit light is being projected, to the image sensor 5. The image sensor 5 includes a light detecting plane that receives the light directed by the optical system 4.

The light directed by the optical system 4, that is, the light coming from the anterior segment of the subject's eye E, contains return light of the slit light being projected onto the anterior segment, and may further contain other kinds of light. Examples of the return light include reflected light of the slit light, scattered light of the slit light, and fluorescence induced by the slit light. Examples of the other kinds of light include light from the environment in which the slit lamp microscope 1 is installed, such as indoor light (room light) and sunlight. In the case where another illumination system different from the illumination system 2 is provided as an anterior segment illumination system for illuminating the entire anterior segment, return light of the anterior segment illumination light emitted by the anterior segment illumination system may be contained in the light directed by the optical system 4.

The image sensor 5 may be an area sensor that has a two dimensional image detecting area. The image sensor 5 may be, for example, a charge-coupled device (CCD) image sensor, a complementary metal oxide semiconductor (CMOS) image sensor, or another type of image sensor.

The optical system 4 may have, for example, the same or similar configuration as or to the photography system of a conventional slit lamp microscope. For example, the optical system 4 includes an objective lens, a variable magnification optical system, and an imaging lens in the order from the side closer to the subject's eye E. The light coming from the anterior segment of the subject's eye E onto which the slit light is being projected, passes through the objective lens and the variable magnification optical system, and then forms an image on the light detecting plane of the image sensor 5 by the imaging lens.

The photography system 3 may include the first photography system and the second photography system, for example. In a typical example, the first photography system and the second photography system have the same configuration. The case in which the photography system 3 includes the first photography system and the second photography system will be described later as another embodiment example.

The photography system 3 may further include a focus mechanism configured for changing the focal position of the photography system 3. The focus mechanism may be configured to move the objective lens along the photography optical axis 3a, for example. The movement of the objective lens may be carried out automatically and/or manually. Note that a focusing lens may be prepared and disposed at a position in the photography optical axis 3a between the objective lens and the imaging lens, and also the focus mechanism may be capable of moving the focusing lens along the photography optical axis 3a, thereby changing the focal position of the photography system 3.

The illumination system 2 and the photography system 3 function as a Scheimpflug camera. More specifically, the illumination system 2 and the photography system 3 are configured in such a manner that the subject plane along the illumination optical axis 2a, the optical system 4, and the light detecting plane of the image sensor 5 satisfy what is commonly referred to as the Scheimpflug condition. More specifically, the YZ plane passing through the illumination optical axis 2a (the YZ plane contains the subject plane), the principal plane of the optical system 4, and the light detecting plane of the image sensor 5 intersect on the same straight line. As a result of this, photographing can be performed with all positions in the subject plane in focus. In other words, photographing can be performed with all positions in the direction along the illumination optical axis 2a in focus.

The illumination system 2 and the photography system 3 of the present embodiment example are configured in such a manner that at least a site defined by the anterior surface of the cornea C and the posterior surface of the crystalline lens CL is in focus of the photography system 3. In other words, photography may be performed in a state in which the focus of the photography system 3 is on the entire area from the apex of the anterior surface of the cornea C (Z=Z1) to the apex of the posterior surface of the crystalline lens CL (Z=Z2) shown in FIG. 1. Note that the location Z=Z0 corresponds to the Z coordinate of the intersection of the illumination optical axis 2a and the photography optical axis 3a.

The condition described above is typically realized by the configuration and arrangement of the elements included in the illumination system 2, the configuration and arrangement of the elements included in the photography system 3, and the relative positions between the illumination system 2 and the photography system 3. A parameter indicating the relative positions of the illumination system 2 and the photography system 3 may include the angle θ formed by the illumination optical axis 2a and the photography optical axis 3a, for example. The value of the angle θ may be set to 17.5 degrees, 30 degrees, or 45 degrees, for example. The angle θ may be variable.

[Movement Mechanism 6]

The movement mechanism 6 is configured to move the illumination system 2 and the photography system 3. The movement mechanism 6 of the present embodiment example is configured to move the illumination system 2 and the photography system 3 together with each other in the X direction.

For example, the movement mechanism 6 includes a movable stage, an actuator, and a mechanism. The illumination system 2 and the photography system 3 are placed on the movable stage. The actuator is configured to operate according to a control signal input from the controller 7. The mechanism is configured to receive driving force generated by the actuator and move the movable stage. In another example, the movement mechanism 6 may include a movable stage on which the illumination system 2 and the photography system 3 are placed, and a mechanism configured to receive force applied to an operation device (not shown in the drawings) and move the movable stage. The operation device is a lever, for example. The movable stage may be movable at least in the X direction and may be further movable in at least one of the Y direction and the Z direction.

[Controller 7]

The controller 7 is configured to control each part of the slit lamp microscope 1. For example, the controller 7 controls elements of the illumination system 2 (e.g., illumination light source, slit forming member, focus mechanism, etc.), elements of the photography system 3 (e.g., focus mechanism, image sensor, etc.), the movement mechanism 6, the data processor 8, and the communication device 9, and the like. Further, the controller 7 may be capable of executing control for changing the relative positions of the illumination system 2 and the photography system 3.

The controller 7 includes a processor, a primary storage, a secondary storage, and the like. The secondary storage stores a control program and the like. The control program and the like may be stored in a computer or a storage accessible by the slit lamp microscope 1. The function of the controller 7 is realized by cooperation of software such as the control program and hardware such as the processor.

The controller 7 may be capable of applying the following controls to the illumination system 2, the photography system 3 and the movement mechanism 6 in order to scan a three dimensional region of the anterior segment of the subject's eye E with the slit light.

Figure 2A:
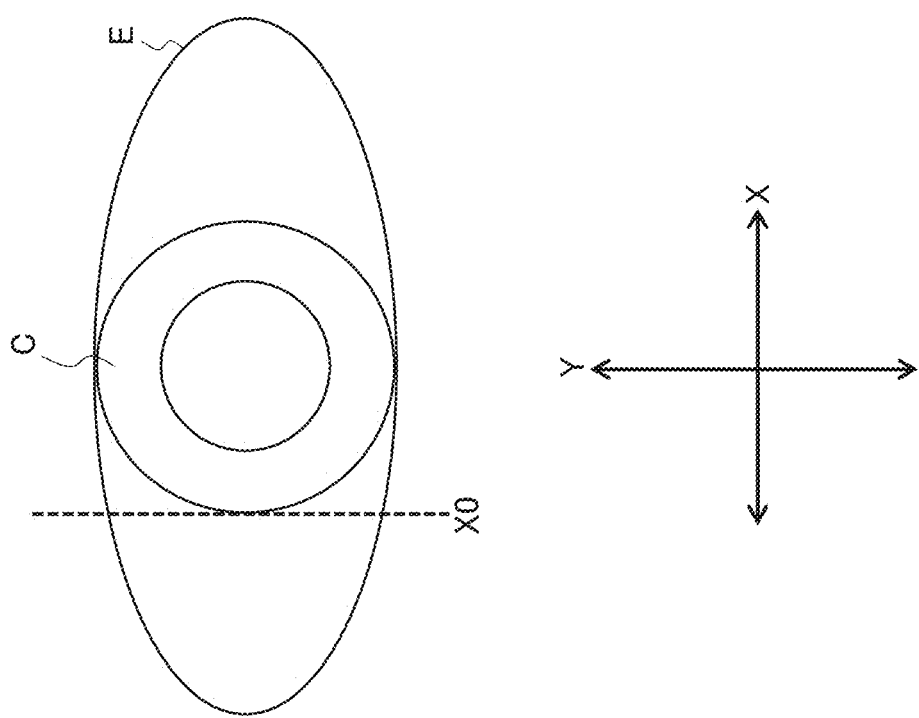
FIG. 2A is a schematic diagram for describing the operation of the slit lamp microscope according to the embodiment example.
Figure 2B:
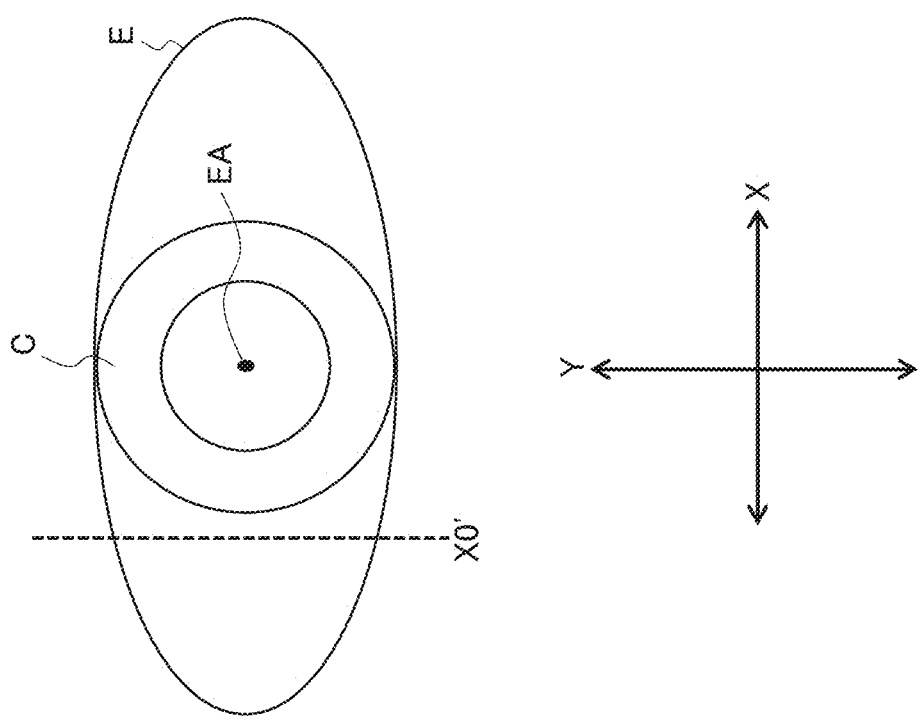
FIG. 2B is a schematic diagram for describing the operation of the slit lamp microscope according to the embodiment example.

First, the controller 7 controls the movement mechanism 6 to place the illumination system 2 and the photography system 3 at a predetermined scan start position. This control is referred to as alignment control. The scan start position is, for example, a position corresponding to the edge position (first edge position) of the cornea C in the X direction, or a position further away from the axis of the subject's eye E than the first edge position. The reference character XO shown in FIG. 2A denotes a scan start position corresponding to the first edge position of the cornea C in the X direction. Further, the reference character XO' shown in FIG. 2B denotes a scan start position further away from the axis EA of the subject's eye E than the position corresponding to the first edge position of the cornea C in the X direction.

The controller 7 controls the illumination system 2 to start the projection of the slit light onto the anterior segment of subject's eye E. This control is referred to as slit light projection control. The slit light projection control may be performed before the execution of the alignment control or during the execution of the alignment control. The illumination system 2 is typically configured to project continuous light or steady light as the slit light; however, the illumination system 2 may be configured to project intermittent light (pulse light) as the slit light. Further, the illumination system 2 is typically configured to project visible light as the slit light; however, the illumination system 2 may be configured to project infrared light as the slit light.

The controller 7 controls the photography system 3 to start moving image photography (moving image acquisition) of the anterior segment of the subject's eye E. This control is referred to as photography control. The photography control may be performed before the execution of the alignment control or during the execution of the alignment control. Typically, the photography control is executed simultaneously with the slit light projection control or after the slit light projection control.

After having executed the alignment control, the slit light projection control, and the photography control, the controller 7 performs control of the movement mechanism 6 to start the movement of the illumination system 2 and the photography system 3. This control is referred to as movement control. The illumination system 2 and the photography system 3 are moved together by the movement control. In other words, the movement mechanism 6 moves the illumination system 2 and the photography system 3 while maintaining the relative positions (e.g., the angle θ) between the illumination system 2 and the photography system 3. The movement of the illumination system 2 and the photography system 3 is performed from the aforementioned scan start position to a predetermined scan end position. The scan end position is, for example, a position corresponding to the edge position (second edge position) of the cornea C on the opposite side of the first edge position in the X direction, or a position further away from the axis of the subject's eye E than the second edge position, as in the scan start position. In such a case, the area from the scan start position to the scan end position becomes a scan area.

Typically, the photography system 3 carries out the moving image photography in parallel with the projection of the slit light onto the anterior segment and the movement of the illumination system 2 and the photography system 3 in the X direction. Here, the width direction of the slit light corresponds to the X direction and the longitudinal direction of the slit light corresponds to the Y direction.

Here, the length of the slit light (that is, the size of the slit light in the Y direction) is set to be, for example, equal to or greater than the diameter of the cornea C on the surface of the subject's eye E. In other words, the length of the slit light is set to be equal to or greater than the corneal diameter in the Y direction. Further, the distance of the movement of the illumination system 2 and the photography system 3 carried out by the movement mechanism 6 (that is, scan area) is set to be equal to or greater than the corneal diameter in the X direction, as described above. As a result of setting the slit light length and the movement distance in these manners, an area including the entire cornea C can be scanned with the slit light.

Figure 3:
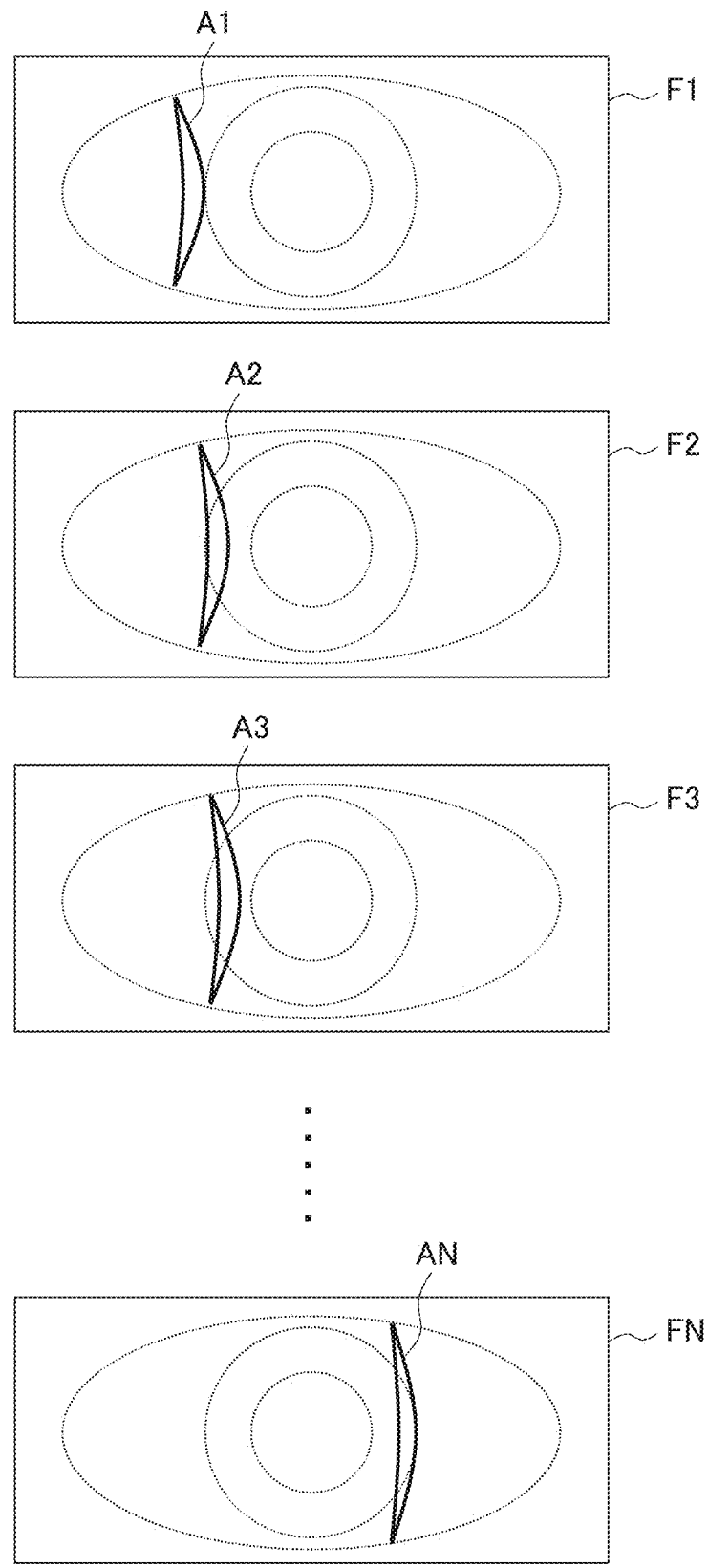
FIG. 3 is a schematic diagram for describing the operation of the slit lamp microscope according to the embodiment example.

With such a scan, a plurality of anterior segment images corresponding to mutually different slit light projection positions is acquired. In other words, a moving image is obtained in which the state (aspect) of the movement of the slit light projection position in the X direction. FIG. 3 shows an example of such a plurality of anterior segment images, that is, an example of such a group of frames (a frame group) composing a moving image.

FIG. 3 shows the plurality of anterior segment images (the frame group) F1, F2, F3, . . . , and FN. The subscripts "n" of the anterior segment images Fn (n=1, 2, . . . , N) represent a time series order. In other words, the n-th anterior segment image acquired is represented by the reference character "Fn". The anterior segment image Fn includes the region onto which the slit light is being projected (slit light projected region) An. As shown in FIG. 3, the positions of the slit light projected regions A1, A2, A3, . . . , and AN shift to the right in time series order. The scan start position and the scan end position in the example shown in FIG. 3 correspond to both edge positions of the cornea C in the X direction. The scan start position and/or the scan end position are/is not limited to the present example. The scan start position and/or the scan end position may be a position(s) further away from the axis of the subject's eye E than the edge position(s) of the cornea, for example. In addition, the direction and number of scans may be set accordingly.

[Data Processor 8]

The data processor 8 executes various kinds of data processing. Data to be processed may be either any data acquired by the slit lamp microscope 1 or any data input from the outside. For example, the data processor 8 can process images acquired by using the illumination system 2 and the photography system 3. Note that the configuration examples and the function examples of the data processor 8 will be described in other embodiment examples.

The data processor 8 includes a processor, a primary storage, a secondary storage, and the like. The secondary storage stores a data processing program and the like. The data processing program and the like may be stored in a computer or a storage accessible by the slit lamp microscope 1. The function of the data processor 8 is realized by cooperation of software such as the data processing program and hardware such as the processor.

[Communication Device 9]

The communication device 9 performs data communication between the slit lamp microscope 1 and another apparatus. In other words, the communication device 9 performs transmission of data to another apparatus and reception of data transmitted from another apparatus.

The system or method of the data communication executed by the communication device 9 may be selected accordingly. For example, the communication device 9 may include any one or more of various kinds of communication interfaces such as a communication interface conforming to the Internet, a communication interface conforming to a dedicated line, a communication interface conforming to a local area network (LAN), and a communication interface conforming to near field communication. The data communication may include any one or both of wireless communication and wired communication.

Data sent and received by the communication device 9 may be encrypted. If this is the case, for example, any one or both of the controller 7 and the data processor 8 include(s) at least one of an encryptor and a decryptor. The encryptor is configured to encrypt data to be sent by the communication device 9. The decryptor is configured to decrypt data having been received by the communication device 9.

[Other Elements]

In addition to the elements shown in FIG. 1, the slit lamp microscope 1 may further include a display device and an operation device. In other aspects, a display device and an operation device may be peripheral devices of the slit lamp microscope 1.

The display device is configured to display various kinds of information under the control of controller 7. The display device may include a flat panel display such as a liquid crystal display (LCD).

The operation device includes a device for operating the slit lamp microscope 1 and/or a device for inputting information. The operation device includes, for example, a button, a switch, a lever, a dial, a handle, a knob, a mouse, a keyboard, a trackball, an operation panel, or the like.

A device such as a touch screen may be employed in which a display device and an operation device are integrated.

The subject (patient) or an assistant may operate the slit lamp microscope 1 by using the display device and the operation device.

[Alignment]

A description will be given of the alignment of the slit lamp microscope 1 with respect to the subject's eye E. Alignment, in general, is an operation to place an optical system of an apparatus at an appropriate position for photography or measurement of the subject's eye E. The alignment of the present embodiment example is an operation to place the illumination system 2 and the photography system 3 at appropriate positions for acquisition of a moving image as shown in FIG. 3.

There are various kinds of methods and techniques for alignment of an ophthalmic apparatus. While some alignment methods and techniques will be described below, alignment methods and techniques applicable to the present embodiment example are not limited to them.

One of the alignment methods and techniques applicable to the present embodiment example is stereo alignment. Stereo alignment may be applicable to an ophthalmic apparatus capable of photographing an anterior segment from two or more mutually different directions (two or more mutually different viewpoints). A specific method of stereo alignment is disclosed by the present applicant in Japanese Unexamined Patent Application Publication No. 2013-248376. Stereo alignment includes, for example, the following steps: a step of photographing the anterior segment from different directions by two or more anterior segment cameras to acquire two or more photographed images; a step of analyzing the photographed images by a processor to determine a three dimensional position of the subject's eye; and a step of performing movement control of an optical system by a processor based on the three dimensional position determined. With such an alignment operation, the optical system (the illumination system 2 and the photography system 3 in the present example) is brought to and placed at an appropriate alignment position with respect to the subject's eye. The position of the pupil (e.g., the center of the pupil or the center of gravity of the pupil) of the subject's eye is used as a reference (or an indicator) in a typical stereo alignment.

In addition to the stereo alignment described hereinbefore, any known alignment methods and techniques may be employed, such as an alignment method or technique using a Purkinje image formed by alignment light, or an alignment method or technique using an optical lever. The position of the corneal apex of the subject's eye is used as a reference (indicator) in the alignment method or technique using a Purkinje image and the alignment method or technique using an optical lever.

Conventional typical alignment methods and techniques including the above examples are performed for the purpose of matching the optical axis of an optical system with the axis of a subject's eye. On the other hand, the present embodiment example may perform alignment so as to place the illumination system 2 and the photography system 3 at a position corresponding to the scan start position.

The first example of the alignment of the present embodiment example may be carried out in the following manner. First, alignment with reference to the pupil or corneal apex of the subject's eye E may be performed by applying any of the alignment methods and techniques described above. Then, the illumination system 2 and the photography system 3 may be moved (in the X direction) by a distance corresponding to a standard value of the corneal radius set in advance. Note that a measurement value of the corneal radius of the subject's eye E may be used instead of the standard value.

The second example of the alignment of the present embodiment example may be carried out in the following manner. First, alignment with reference to the pupil or corneal apex of the subject's eye E may be performed by applying any of the alignment methods and techniques described above. Second, the corneal radius of the subject's eye E may be measured by analyzing an image of anterior segment. Third, the illumination system 2 and the photography system 3 may be moved (in the X direction) by a distance corresponding to the measurement value of the corneal radius of the subject's eye E. The image of the anterior segment analyzed in the present example is an anterior segment image obtained by the photography system 3 or another image, for example. The another image here may be an image of any kind, such as an image obtained by an anterior segment camera, an image obtained by an anterior segment OCT, or the like.

The third example of the alignment of the present embodiment example may be carried out in the following manner. First, the first edge position of the cornea may be determined by analyzing an image of the anterior segment acquired by the anterior segment camera for stereo alignment or by the photography system 3. Then, the illumination system 2 and the photography system 3 may be moved to a position corresponding to the first edge position by applying stereo alignment.

It should be noted that alignment may be performed with reference to the pupil or corneal apex of the subject's eye E by applying any of the alignment methods and techniques described above, and then the anterior segment scan with slit light may be started from the position determined by the alignment. In such a case as well, a scan sequence may be set to scan the entire cornea C. For example, the scan sequence may be set such that the scan is performed to the left from the position determined by the alignment and then to the right.

[Some Additional Matters and Items]

The slit lamp microscope 1 may be provided with a fixation system configured to output light for fixation of the subject's eye E (referred to as fixation light). The fixation system typically includes at least one visible light source (referred to as a fixation light source(s)) or a display device configured to display an image such as a landscape chart or a fixation target. The fixation system of some example aspects is arranged coaxially or non-coaxially with the illumination system 2 or the photography system 3.

The types (kinds) of images that may be acquired by the slit lamp microscope 1 are not limited to the moving image of the anterior segment (i.e., the plurality of anterior segment images) described above. For example, the slit lamp microscope 1 may acquire any of the following types of images: a three dimensional image constructed based on the moving image; a rendered image constructed based on the three dimensional image; a transillumination image (red reflex image); a moving image representing movement of a contact lens applied to the subject's eye; and an image representing a gap between a contact lens and the corneal surface by fluorescent agent administration. A rendered image will be described in another embodiment example. A transillumination image is an image obtained by a red reflex technique for depicting opacity and foreign bodies in the eye by using the retinal reflection of illumination light. Note that the slit lamp microscope 1 may be capable of carrying out fundus photography, corneal endothelial cell photography, Meibomian gland photography, and the like.

[Usage Mode]

Figure 4:
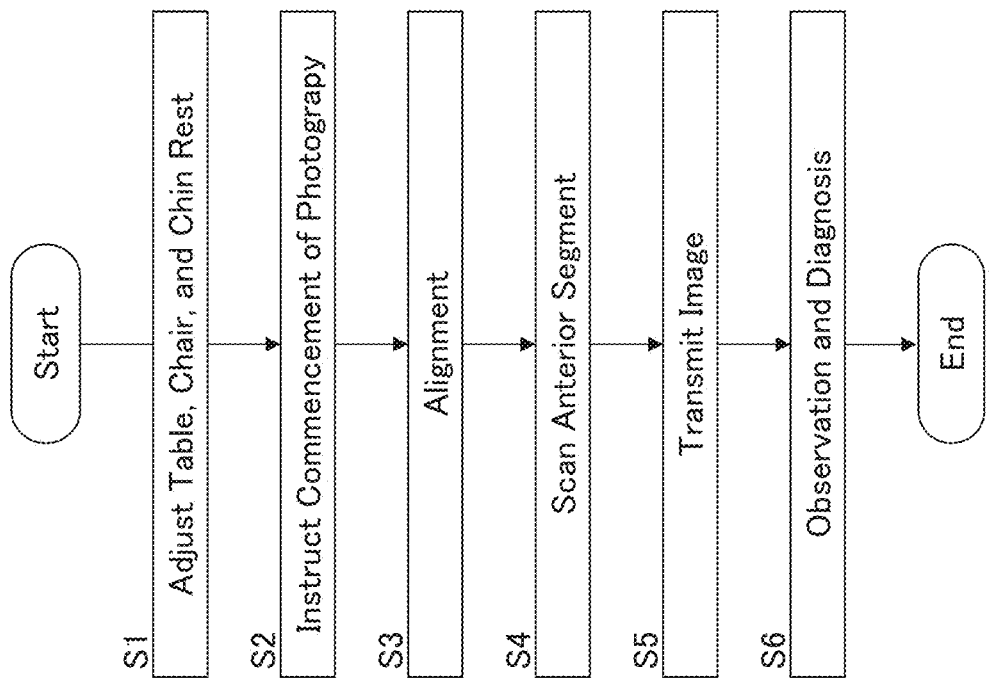
FIG. 4 is a flowchart illustrating the usage mode of the slit lamp microscope according to the embodiment example.

A description will be given of a usage mode of the slit lamp microscope 1 (a system that includes the slit lamp microscope 1). FIG. 4 shows an example of the usage mode.

While not shown in the drawings, the subject or an assistant inputs subject information into the slit lamp microscope 1 at any stage. The subject information input is stored in the controller 7. The subject information typically includes identification information of the subject (referred to as subject ID).

Furthermore, background information may also be input. The background information is any kind of information related to the subject, and examples thereof include information acquired by a medical interview of the subject, information on a sheet filled in by the subject, information recorded in the electronic medical record of the subject, and the like. Typically, the background information includes the subject's data on items such as gender, age, height, weight, disease name, possible disease name, examination result (e.g., visual acuity value, eye refractive power value, intraocular pressure value), history of a wearing device for refractive correction (e.g., history of wearing glasses, contact lenses) and the power of the device, examination history, and treatment history. These are examples only, and items of the background information are not limited to them.

(S1: Adjust Table, Chair, and Chin Rest)

First, the table on which the slit lamp microscope 1 is installed, the chair on which the subject sits, and the chin rest of the slit lamp microscope 1 are adjusted (all not shown in the drawings). For example, the heights of the table, chair and chin rest are adjusted. These adjustments are performed, for example, by the subject. Alternatively, the assistant may conduct any of these adjustments. The chin rest is provided with a chin rest member and a forehead rest member for stably positioning the face of the subject.

(S2: Instruct Commencement of Photography)

After the completion of the adjustments in the step S1, the subject sits on the chair, puts his/her chin on the chin rest member, and puts his/her forehead on the forehead rest member. Before or after these actions, the subject or the assistant performs an operation of issuing an instruction to start photography of the subject's eye. This operation is conducted, for example, by pressing a photography start trigger button (not shown in the drawings).

(S3: Alignment)

In response to the instruction issued in the step S2, the slit lamp microscope 1 performs alignment with respect to subject's eye E as described above. Focus adjustment may be carried out after the completion of the alignment.

(S4: Scan Anterior Segment)

The slit lamp microscope 1 scans the anterior segment of the subject's eye E by combining the projection of the slit light performed by the illumination system 2, the moving image photography performed by the photography system 3, and the movement of the illumination system 2 and the photography system 3 performed by the movement mechanism 6 as described above. As a result the combinational operations, a plurality of anterior segment images, such as the anterior segment images F1 to FN shown in FIG. 3, may be obtained.

The data processor 8 may process at least one of the anterior segment images F1 to FN. For example, as described in another embodiment example, the data processor 8 is capable of constructing a three dimensional image based on the anterior segment images F1 to FN. Further, the data processor 8 may be configured to perform predetermined image processing and/or predetermined image analysis.

(S5: Transmit Image)

The controller 7 controls the communication device 9 to transmit, to another apparatus, images of the anterior segment acquired by the slit lamp microscope 1. Examples of the images of the anterior segment transmitted include the anterior segment images F1 to FN, part of the anterior segment images F1 to FN, and a three dimensional image constructed based on the anterior segment images F1 to FN.

Examples of the another apparatus to which the images of the anterior segment are transmitted include an information processing apparatus and a storage. The information processing apparatus is, for example, a server on a wide area network, a server on a LAN, a computer terminal, or the like. The storage is a storage provided on a wide area network, a storage provided on a LAN, or the like.

The background information may be transmitted along with the images of the anterior segment. In addition, identification information of the subject is transmitted together with the images of the anterior segment. The identification information may be the subject ID input to the slit lamp microscope 1 (described above), or identification information generated based on the subject ID. As an example of the identification information generated based on the subject ID, the subject ID used for personal identification in the facility where the slit lamp microscope 1 is installed (referred to as internal identification information) may be converted into external identification information used outside the facility.

Such identification information conversion makes it possible to improve the information security of personal information such as anterior segment images and background information.

(S6: Observation and Diagnosis)

The images of the anterior segment of the subject's eye E (and the identification information of the subject, the background information of the subject, and the like) transmitted from the slit lamp microscope 1 in the step S5 are sent directly or indirectly to an information processing apparatus used by a doctor (or an optometrist), for example.

The doctor (or the optometrist) can conduct observation of the images of the anterior segment of the subject's eye E. During the observation, the information processing apparatus may execute any of the followings, for example: displaying a predetermined number of images among the anterior segment images F1 to FN at a time; tiling and displaying the anterior segment images F1 to FN; displaying the anterior segment images F1 to FN as a slide show; constructing a three dimensional image from the anterior segment images F1 to FN; and displaying a rendered image of the three dimensional image.

The doctor (or the optometrist) can conduct diagnostic imaging (image diagnosis, image interpretation) by observing the images of the anterior segment of subject's eye E. The doctor (or the optometrist) can create a report in which information obtained from the interpretation is recorded. The report is transmitted, for example, to the facility where the slit lamp microscope 1 is installed. In some examples, the report may be sent to the address information (e.g., email address, address, etc.) registered by the subject. This is the end of the description of the processes according to the present example.

Technical Effects

Some advantageous technical effects achieved by the present embodiment example will be described.

The slit lamp microscope 1 includes the illumination system 2, the photography system 3, and the movement mechanism 6. The illumination system 2 is configured to project slit light onto the anterior segment of the subject's eye E. The photography system 3 includes the optical system 4 and the image sensor 5. The optical system 4 is configured to direct light coming from the anterior segment onto which the slit light is being projected. The image sensor 5 includes the light detecting plane that receives the light directed by the optical system 4. The movement mechanism 6 is configured to move the illumination system 2 and the photography system 3.

Further, the illumination system 2 and the photography system 3 are configured in such a manner that the subject plane along the optical axis of the illumination system 2 (illumination optical axis) 2*a*, the optical system 4, and the light detecting plane of the image sensor 5 satisfy the Scheimpflug condition.

In addition, the photography system 3 acquires a plurality of images of the anterior segment of the subject's eye E by performing repetitive photography in parallel with movement of the illumination system 2 and the photography system 3 performed by the movement mechanism 6. Typically, the repetitive photography is moving image photography. With the moving image photography, a moving image consisting of a plurality of anterior segment images is obtained.

According to the slit lamp microscope 1 configured in this way, a three dimensional region of the anterior segment of the subject's eye E can be scanned with the slit light by the movement of the illumination system 2 and the photography system 3, and therefore an image representing the three dimensional region can be acquired. As a result, a doctor or an optometrist may observe the images acquired by the slit lamp microscope 1 to grasp the state of a desired site of the anterior segment.

In addition, the images acquired by the slit lamp microscope 1 can be provided to a doctor or an optometrist in a remote place. Typically, the slit lamp microscope 1 can transmit, by using the communication device 9, the images acquired of the anterior segment of the subject's eye E to an information processing apparatus used by the doctor or the optometrist. Note that providing the communication device 9 is optional. The method of providing the images acquired by the slit lamp microscope 1 is not limited to such data communication, and may be any method such as a method of providing a recording medium or a print medium on which the images are recorded. Recording on the recording medium is realized by using a recording device (i.e., data writer) conforming to the recording medium, and recording on the print medium is realized by using a printing device (i.e., printer).

Further, since the slit lamp microscope 1 is configured such that the subject plane along the illumination optical axis 2a, the optical system 4, and the light detecting plane of the image sensor 5 satisfy the Scheimpflug condition, the slit lamp microscope 1 is capable of focusing on a large area (broad range, wide range) in the depth direction (Z direction). For example, the illumination system 2 and the photography system 3 are configured in such a manner that at least a region defined by the anterior corneal surface and the posterior crystalline lens surface is in focus of the photography system 3. Such a configuration allows the slit lamp microscope 1 to achieve imaging of the entire main site of the anterior segment being subjected to the slit lamp microscope examination with high definition. An area (range) in focus is not limited to the above region defined by the anterior corneal surface and the posterior crystalline lens surface, and may be set accordingly.

If a configuration that does not satisfy the Scheimpflug condition is employed, it is necessary to move the illumination system and the photography system along a curved path according to the shape of the anterior corneal surface while focusing on each site of the anterior segment, in order to focus on a broad range in the depth direction and photograph a three dimensional region. Such an operation and/or control are/is cumbersome and impractical.

Further, the illumination system 2 may project the slit light whose longitudinal direction corresponds to the body axis direction (Y direction) of the subject, onto the anterior segment. In addition, the movement mechanism 6 may be configured to be capable of moving the illumination system 2 and the photography system 3 in a direction (X direction) orthogonal to the body axis direction of the subject. The orientation and the movement direction of the slit light are not limited to these, and can be set accordingly. Typically, the movement direction is set to the width direction of the slit light.

In the case where the slit light whose longitudinal direction corresponds to the body axis direction is projected, and the illumination system 2 and the photography system 3 are moved in the direction orthogonal to the body axis direction, the illumination system 2 may be configured in such a manner that the length of the slit light (i.e., the size of the slit light in the body axis direction) is equal to or greater than the corneal diameter in the body axis direction. In addition, the movement mechanism 6 may be configured such that the distance of the movement of the illumination system 2 and the photography system 3 performed by the movement mechanism 6 is equal to or greater than the corneal diameter in the direction (X direction) orthogonal to the body axis direction. The corneal diameter may be the corneal diameter value of the subject's eye E or a standard value of corneal diameters. The length of the slit light and the distance of the movement are not limited to these, and can be set accordingly.

With such a configuration, an image can be acquired for the entire cornea. Furthermore, combining this configuration with the configuration that satisfies the Scheimpflug condition allows the slit lamp microscope 1 to acquire an image representing a sufficient depth range as well as the entire cornea.

As described above, according to the slit lamp microscope 1, a high quality image representing a large area (a three dimensional region) of the anterior segment can be automatically acquired without a technical expert having to perform fine, delicate, sophisticated, cumbersome, and troublesome operations. A medical image interpreter may receive the images acquired by the slit lamp microscope 1 and conduct observation and diagnosis.

Such advantages can make a contribution in solving the problem of shortage of technical experts and also make it possible to widely provide high quality examinations using slit lamp microscopes. For example, the slit lamp microscope 1 described thus far can be said to be effective in screening for anterior segment diseases and other diseases.

Below, some examples of functions and configurations that may be combined with the slit lamp microscope 1 will be described. In the following embodiment examples, the same or similar elements as or to those in the first embodiment example may be denoted by the same reference characters. Further, the same or similar elements as or to those in the first embodiment example may be omitted in the figures referred to in the following embodiment examples.

Second Embodiment Example

Figure 5:
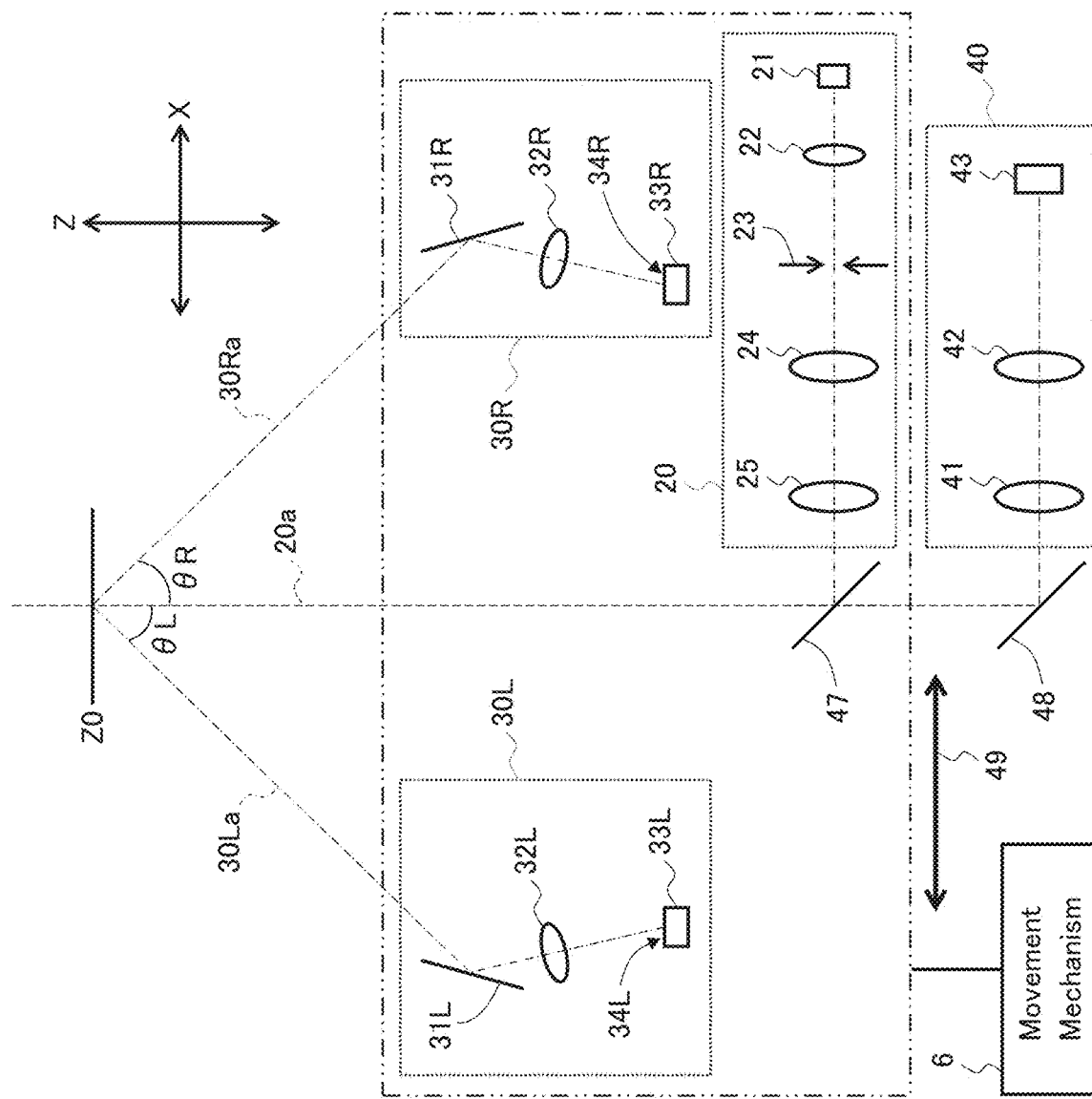
FIG. 5 is a schematic diagram illustrating the configuration of the slit lamp microscope according to the embodiment example.

The present embodiment example describes a configuration of an optical system applicable to the slit lamp microscope 1 of the first embodiment example. An example thereof is shown in FIG. 5. In addition to the elements shown in FIG. 5, the slit lamp microscope 1 of the present embodiment example may further be provided with any of the elements shown in other embodiment examples. For example, the controller 7, the data processor 8, the communication device 9, etc. of the first embodiment example may be provided.

The illumination system 20 shown in FIG. 5 is an example of the illumination system 2 of the first embodiment example, and the pair of the left photography system 30L and the right photography system 30R is an example of the photography system 3. The reference character 20a denotes the optical axis of the illumination system 20 (referred to as the illumination optical axis), the reference character 30La denotes the optical axis of the left photography system 30L (referred to as the left photography optical axis), and the reference character 30Ra denotes the optical axis of the right photography system 30R (referred to as the right photography optical axis). The orientation of the left photography optical axis 30La and the orientation of the right photography optical axis 30Ra are different from each other. The angle formed by the illumination optical axis 20a and the left photography optical axis 30La is denoted by OL, and the angle formed by the illumination optical axis 20a and the right photography optical axis 30Ra is denoted by θR. The angle θL and the angle θR may be equal to or different from each other. The illumination optical axis 20a, the left photography optical axis 30La, and the right photography optical axis 30Ra intersect at one point. As with FIG. 1, the Z coordinate of the intersection is denoted by Z0.

The movement mechanism 6 is capable of moving the illumination system 20, the left photography system 30L, and the right photography system 30R in the direction denoted by the arrow 49 (X direction). Typically, the illumination system 20, the left photography system 30L, and the right photography system 30R are mounted on a stage that is movable at least in the X direction, and the movement mechanism 6 moves the movable stage under a control signal from the controller 7.

The illumination system 20 is configured to project slit light onto the anterior segment of the subject's eye E. Similar to the illumination system of a conventional slit lamp microscope, the illumination system 20 includes the illumination light source 21, the positive lens 22, the slit forming member 23, and the group of objective lenses 24 and 25 in the order from the side far from the subject's eye E.

The illumination light output from the illumination light source 21 (typically, visible light) is refracted by the positive lens 22 and projected onto the slit forming member 23. Part of the illumination light projected onto the slit forming member 23, passes through the slit formed by the slit forming member 23 and becomes slit light. The slit light generated by the slit forming member 23 is refracted by the group of objective lenses 24 and 25, and then reflected by the beam splitter 47, and projected onto the anterior segment of the subject's eye E.

The left photography system 30L includes the reflector 31L, the imaging lens 32L, and the image sensor 33L. The reflector 31L and the imaging lens 32L direct, to the image sensor 33L, light coming from the anterior segment onto which the slit light is being projected by the illumination system 20 (i.e., light coming from the anterior segment and traveling in the direction of the left photography system 30L).

The light traveling in the direction of the left photography system 30L from the anterior segment corresponds to light that comes from the anterior segment onto which the slit light is being projected and that travels in the direction away from the illumination optical axis 20a. The reflector 31L is arranged to reflect the light toward a direction approaching the illumination optical axis 20a. The imaging lens 32L refracts the light reflected by the reflector 31L and forms an image on the light detecting plane 34L of the image sensor 33L. The image sensor 33L receives and detects the light by the light detecting plane 34L.

As in the first embodiment example, the left photography system 30L performs repetitive photography in parallel with movement of the illumination system 20, the left photography system 30L, and the right photography system 30R performed by the movement mechanism 6. This acquires a plurality of anterior segment images.

Also as in the first embodiment example, the subject plane along the illumination optical axis 20a, the optical system that includes the reflector 31L and the imaging lens 32L, and the light detecting plane 34L satisfy the Scheimpflug condition. More specifically, considering the deflection of the optical path of the photography system 30L by the reflector 31L, the YZ plane (including the subject plane) passing through the illumination optical axis 20a, the principal plane of the imaging lens 32L, and the light detecting plane 34L intersect on the same straight line. As a result, the left photography system 30L may perform photography with all positions in the subject plane (e.g., the area from the anterior corneal surface to the posterior crystalline lens surface) in focus.

The right photography system 30R includes the reflector 31R, the imaging lens 32R, and the image sensor 33R. Like the left photography system 30L, the right photography system 30R directs light coming from the anterior segment onto which the slit light is being projected by the illumination system 20 to the light detecting plane 34R of the image sensor 33R by the reflector 31R and the imaging lens 32R. Further, as with the left photography system 30L, the right photography system 30R acquires a plurality of anterior segment images by performing repetitive photography in parallel with movement of the illumination system 20, the left photography system 30L, and the right photography system 30R performed by the movement mechanism 6. As in the case of the left photography system 30L, the subject plane along the illumination optical axis 20a, the optical system that includes the reflector 31R and the imaging lens 32R, and the light detecting plane 34R satisfy the Scheimpflug condition.

The controller 7 may perform synchronization between the repetitive photography carried out by the left photography system 30L and the repetitive photography carried out by the right photography system 30R. With the synchronization, a correspondence relationship may be obtained between the plurality of anterior segment images obtained by the left photography system 30L and the plurality of anterior segment images obtained by the right photography system 30R. The correspondence relationship is a temporal correspondence relationship, and more specifically, a correspondence relationship for establishing a pair of images acquired at substantially the same time by the left photography system 30L and the right photography system 30R.

Alternatively, the controller 7 or the data processor 8 may execute a process of determining a correspondence relationship between the plurality of anterior segment images obtained by the left photography system 30L and the plurality of anterior segment images obtained by the right photography system 30R. For example, the controller 7 or the data processor 8 can determine pairs of images from the anterior segment images sequentially input from the left photography system 30L and the anterior segment images sequentially input from the right photography system 30R, according to their input timings.

The present embodiment example further includes the moving image photography system 40. The moving image photography system 40 acquires a moving image of the anterior segment of the subject's eye E from a fixed position in parallel with the photography performed by the left photography system 30L and the right photography system 30R. Here, acquisition of a moving image from a fixed position indicates that the moving image photography system 40 is not moved by the movement mechanism 6, unlike the illumination system 20, the left photography system 30L and the right photography system 30R.

While the moving image photography system 40 of the present embodiment example is arranged coaxially with the illumination system 20, the arrangement is not limited to this. For example, the moving image photography system 40 may be arranged non-coaxially with the illumination system 20. Further, an optical system may be provided which projects, onto the anterior segment, illumination light of a wavelength band(s) detectable by the moving image photography system 40.

The light transmitted through the beam splitter 47 is reflected by the reflector 48 and enters the moving image photography system 40. The light that has entered the moving image photography system 40 is refracted by the objective lens 41 and then forms an image on the light detecting plane of the image sensor 43 by the imaging lens 42. The image sensor 43 may be an area sensor.

In the case where the moving image photography system 40 is employed, movement of the subject's eye E may be monitored and tracking may be performed. Tracking is an operation for making the optical system follow the movement of the subject's eye E. Processing for tracking will be described in another embodiment example.

The beam splitter 47 may be a dichroic mirror or a half mirror, for example, depending on the output wavelength of the illumination system 20 and the detection wavelength of the moving image photography system 40.

Some advantageous technical effects achieved by the present embodiment example will be described.

The present embodiment example is an example of the photography system 3 of the first embodiment example, and includes the left photography system 30L and the right photography system 30R. The combination of the left photography system 30L and the right photography system 30R is an example of the combination of the first photography system and the second photography system.

The left photography system 30L includes the reflector 31L and the imaging lens 32L (first optical system), and the image sensor 33L (first image sensor). The first optical system is configured to direct the light coming from the anterior segment onto which the slit light is being projected. The first image sensor includes the light detecting plane 34L (first light detecting plane) that receives the light directed by the first optical system. Likewise, the right photography system 30R includes the reflector 31R and the imaging lens 32R (second optical system) and the image sensor 33R (second image sensor). The second optical system is configured to direct the light coming from the anterior segment onto which the slit light is being projected. The second image sensor includes the light detecting plane 34R (second light detecting plane) that receives the light directed by the second optical system.

The orientation of the optical axis of the left photography system 30L (the left photography optical axis 30La) and the orientation of the optical axis of the right photography system 30R (the right photography optical axis 30Ra) are different from each other. Further, the subject plane along the optical axis of the illumination system 20 (the illumination optical axis 20a), the reflector 31L and the imaging lens 32L, and the light detecting plane 34L satisfy the Scheimpflug condition. Similarly, the subject plane, the reflector 31R and the imaging lens 32R, and the light detecting plane 34R satisfy the Scheimpflug condition.

The left photography system 30L acquires the first image group by performing repetitive photography in parallel with the movement of the illumination system 20, the left photography system 30L, and the right photography system 30R performed by the movement mechanism 6. Likewise, the right photography system 30R acquires the second image group by performing repetitive photography in parallel with the movement of the illumination system 20, the left photography system 30L, and the right photography system 30R performed by the movement mechanism 6.

According to such a configuration, moving images of the anterior segment onto which the slit light is being projected can be acquired respectively from mutually different directions. There may be a case where an image (first image) acquired by one of the photography systems contains an artifact while the other image (second image) substantially simultaneously acquired with the first image by the other photography system does not contain any artifact. Further, there may be a case where a pair of images substantially simultaneously acquired by the two photography systems both contain artifacts, and the artifact in one of the images overlaps a region of interest (e.g., a region onto which slit light is being projected (slit light projected region)) while the artifact in the other image is not overlap a region of interest. Therefore, the present embodiment example can increase the possibility of being able to obtain proper and adequate images. A process example of obtaining a proper and adequate image from a pair of images acquired substantially at the same time will be described later.

Note that in addition to the first photography system and the second photography system, the photography system 3 may include a third photography system, . . . , K-th photography system (where K is an integer equal to or greater than 3) with a similar configuration.

The left photography system 30L of the present embodiment example includes the reflector 31L and the imaging lens 32L. The reflector 31L is configured to reflect the light coming from the anterior segment onto which the slit light is being projected and traveling in a direction away from the illumination optical axis 20a, toward a direction approaching the illumination optical axis 20a. Further, the imaging lens 32L is configured to form an image of the light reflected by the reflector 31L on the light detecting plane 34L. Here, the imaging lens 32L includes at least one lens.

Likewise, the right photography system 30R includes the reflector 31R and the imaging lens 32R. The reflector 31R is configured to reflect the light coming from the anterior segment onto which the slit light is being projected and traveling in a direction away from the illumination optical axis 20a, toward a direction approaching the illumination optical axis 20a. Further, the imaging lens 32R is configured to form an image of the light reflected by the reflector 31R on the light detecting plane 34R. Here, the imaging lens 32R includes at least one lens.

With such a configuration, reducing the size of the apparatus can be achieved. More specifically, taking into account the fact that the image acquired by the images sensor 33L (33R) are output through a cable extending from the surface on the opposite side of the light detecting plane 34L (34R), the present configuration allows a cable to be arranged from the back surface of the image sensor 33L (33R) located relatively close to the illumination optical axis 20a toward the direction opposite to the subject's eye E. As a result of this, cable routing can be performed in an appropriate manner, making it possible to reduce the size of the apparatus.

In addition, the present configuration allows the angle θL and the angle θR to be set as larger angles. This increases a possibility of an image acquired by one of the photography systems not containing any artifact, while a corresponding image, substantially simultaneously acquired with that image, by the other photography system contains an artifact. Furthermore, even though artifacts are contained in both of a pair of images substantially simultaneously acquired by the both photography systems and an artifact in one of the images overlaps a region of interest (e.g., a region onto which slit light is being projected (slit light projected region)), setting the angle θL and the angle θR to be larger angles can reduce the possibility of an artifact in the other image overlapping a region of interest.

The present embodiment example includes the moving image photography system 40. The left photography system 30L and the right photography system 30R repetitively photograph the anterior segment in parallel with the movement of the illumination system 20, the left photography system 30L and the right photography system 30R performed by the movement mechanism 6. In parallel with this repetitive photography, the moving image photography system 40 acquires a moving image of the anterior segment from a fixed position.

Such a configuration allows acquiring a moving image from the fixed position (e.g., from the front with respect to the subject's eye E) in parallel with the scanning of the anterior segment with slit light. This makes it possible to grasp the state of the subject's eye E during scanning as well as to perform control on the basis of the state of the subject's eye E. Some examples of such control etc. will be described in another embodiment example.

Figure 6:
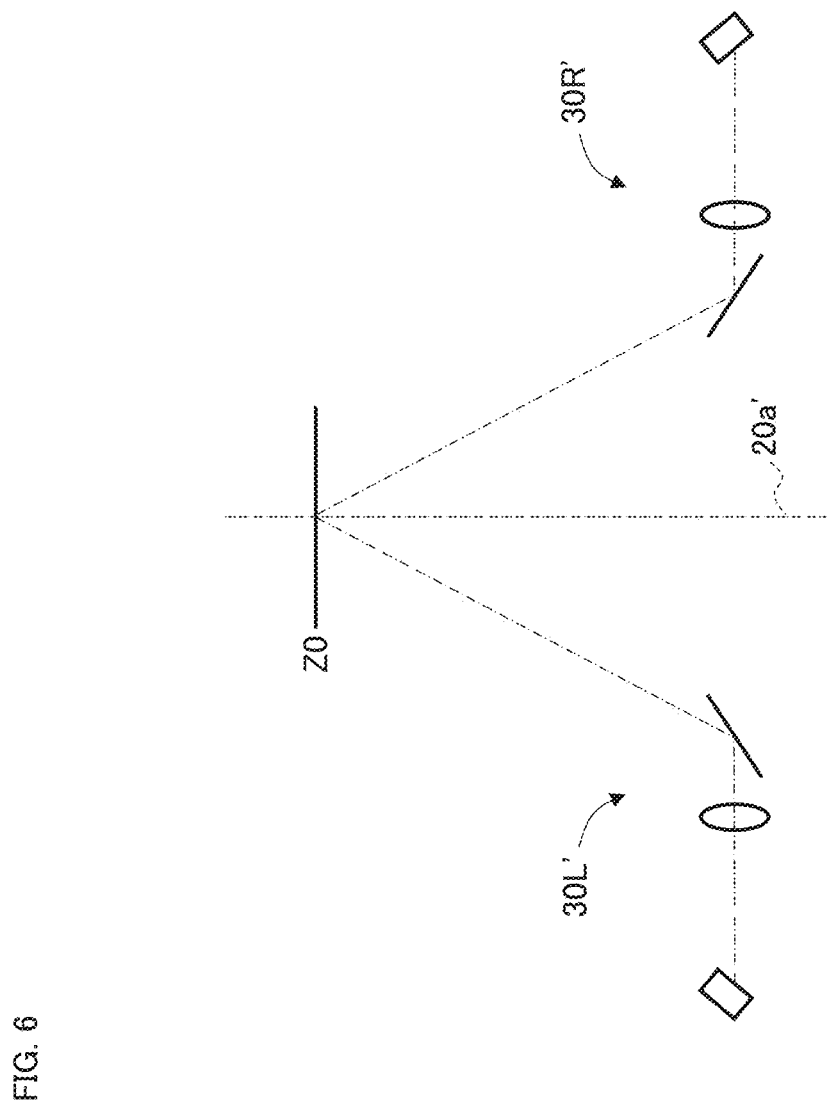
FIG. 6 is a schematic diagram illustrating a modified example of the configuration of the slit lamp microscope according to the embodiment example.

FIG. 6 shows an example of an optical system that may be employed instead of the configuration shown in FIG. 5. The reference characters for the elements shown in FIG. 6 are omitted. In the left photography system 30L' of the optical system according to the present example, the reflector reflects light coming from the anterior segment onto which the slit light is being projected and traveling in a direction away from the illumination optical axis 20a', toward a direction further away from the illumination optical axis 20a'. In addition, the imaging lens forms an image of the light reflected by the reflector on the light detecting plane of the image sensor.

While such a configuration may be employed, this configuration can cause a problem of not being able to achieve appropriate cable routing because the cable is arranged from the back surface of the image sensor, which is located relatively far from the illumination optical axis 20a', to the side (or, to a direction toward the subject's eye E).

Third Embodiment Example

The present embodiment example will describe a configuration example of the processing system applicable to the slit lamp microscope 1 of the first embodiment example. As shown in FIG. 5 described in the second embodiment example, for example, the photography system 3 of the present embodiment example may be configured in such a manner that the left photography optical axis 30La and the right photography optical axis 30Ra are tilted in mutually opposite directions with respect to the illumination optical axis 20a. The processing system of the present embodiment example is configured to execute the processing related to an artifact as described below.

Figure 7:
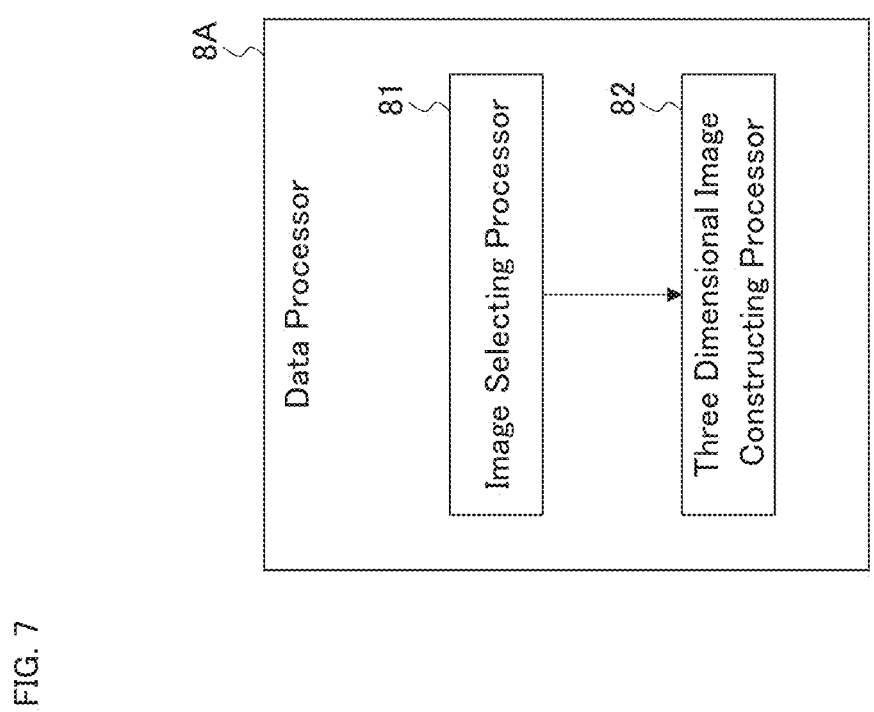
FIG. 7 is a schematic diagram illustrating the configuration of the slit lamp microscope according to the embodiment example.

The data processor 8A shown in FIG. 7 is an example of the data processor 8 of the first embodiment example. The data processor 8A includes the image selecting processor 81.

The image selecting processor 81 is configured to judge whether an artifact is contained in at least one of two images that are substantially simultaneously acquired by the left photography system 30L and the right photography system 30R respectively. The artifact judgement includes a predetermined image analysis and typically includes thresholding relating to brightness information assigned to the pixels of the images.

The thresholding may include identification of a pixel to which a brightness value exceeding a predetermined threshold value is assigned, for example. Typically, the threshold value is set higher than a brightness value of the region onto which the slit light is being projected (slit light projected region) in an image. If the threshold value is set higher than the brightness value of the slit light projected region, the image selecting processor 81 does not judge the slit light projected region as an artifact, while judging an image brighter than the slit light projected region (e.g., a front reflection image) as an artifact.

The image selecting processor 81 may execute any kind of image analysis other than thresholding, such as pattern recognition, segmentation, and edge detection, for the artifact judgement. More generally, any information processing technology and technique such as image analysis, image processing, artificial intelligence technique, and cognitive computing technique may be employed for the artifact judgement.

If a result of the artifact judgement is that only one of the two images substantially simultaneously acquired by the left photography system 30L and the right photography system 30R contains an artifact, the imaging selecting processor 81 selects the other of the two images that does not contain any artifact. In other words, in such a case, the image selecting processor 81 selects one image, from such two images, that is not judged to contain the artifact.

If both of the two images contain artifacts, the image selecting processor 81 of some example may evaluate (assess) adverse effects of the artifacts on observation and diagnosis and then select an image with a smaller adverse effect. In some examples, the evaluation may be made on the basis of the size and/or location of artifacts. Typically, an image containing a large artifact is evaluated as having a large adverse effect, and an image with an artifact located on or near a region of interest, such as a slit light projected region, is evaluated as having a large adverse effect.

If both of the two images contain artifacts, the artifact elimination described in the fourth embodiment example may be performed.

As described in the second embodiment example, the left photography system 30L acquires the first image group by performing repetitive photography in parallel with the movement of the illumination system 20, the left photography system 30L, and the right photography system 30R performed by the movement mechanism 6. Similarly, the right photography system 30R acquires the second image group by performing repetitive photography in parallel with the movement of the illumination system 20, the left photography system 30L, and the right photography system 30R performed by the movement mechanism 6. The repetitive photography is typically moving image photography, and each of the first image group and the second image group is a frame group (group of frames) constituting the corresponding moving image. Further, as described above, images substantially simultaneously acquired among the first image group and the second image group are paired with each other.

The image selecting processor 81 selects one of the two paired images (a pair or combination of an image from the first image group and an image from the second image group). With this selection, for example, one image is selected from each of the plurality of image pairs, and a plurality of images that are substantially free of artifacts are selected.

The data processor 8A further includes the three dimensional image constructing processor 82. The three dimensional image constructing processor 82 is configured to construct a three dimensional image based on an image group including the images selected from the first image group and the second image group by the image selecting processor 81. The image group may include only at least part of the plurality of images selected from the first image group and the second image group by the image selecting processor 81, or may further include one or more other images.

Note that a three dimensional image is an image (image data) in which the positions of pixels are defined by a three dimensional coordinate system. Examples of a three dimensional image include stack data and volume data. Stack data is constructed by embedding (arranging) a plurality of two dimensional images in a single three dimensional coordinate system according to their positional relationship. Volume data, which is also referred to as voxel data, is constructed by applying voxelization to stack data, for example.

An example of three dimensional image construction processing will be described. In this example, an image group to which the three dimensional image construction is applied is the plurality of anterior segment images (frame groups) F1, F2, F3, FN shown in FIG. 3. The anterior segment image Fn includes the slit light projected region An (where n=1, 2, . . . , N).

Figure 8:
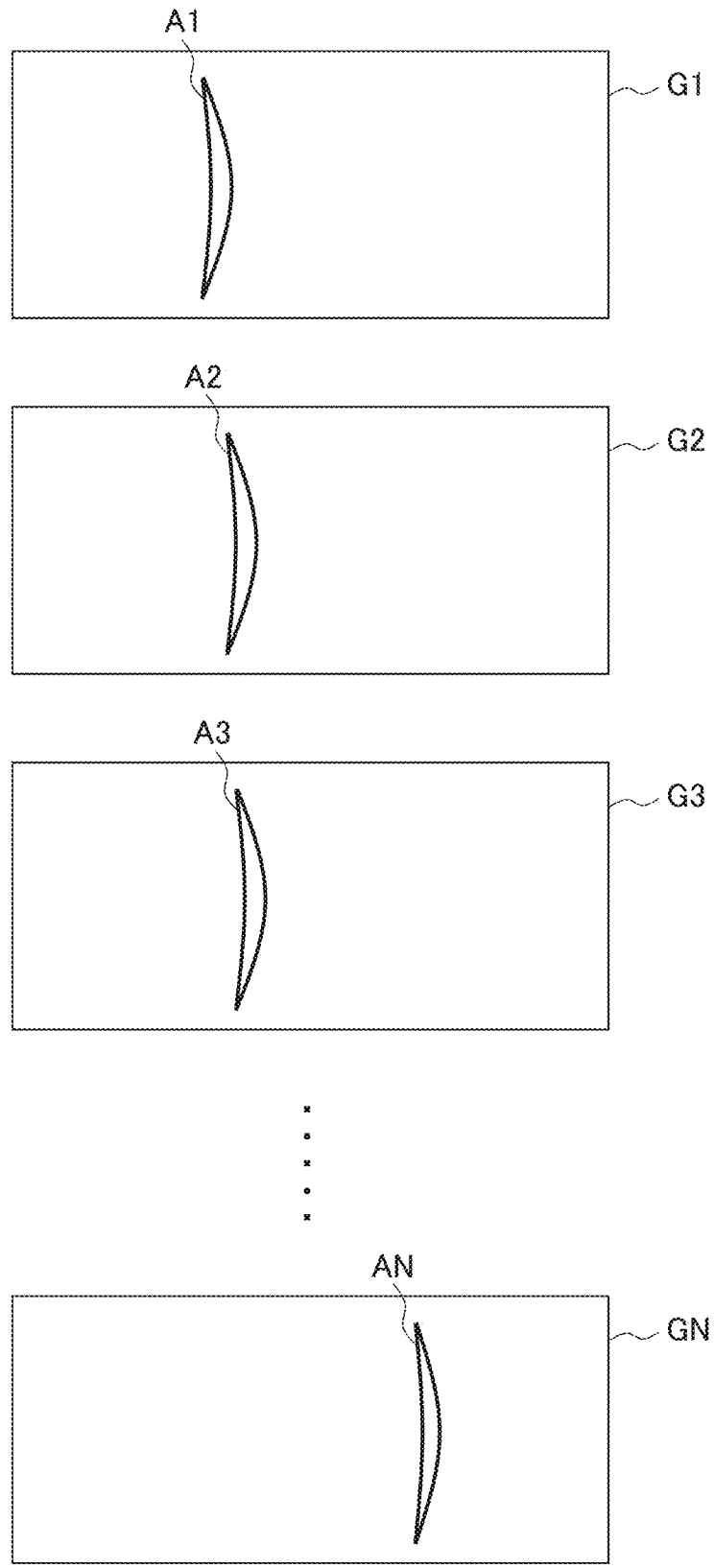
FIG. 8 is a schematic diagram for describing the operation of the slit lamp microscope according to the embodiment example.

The three dimensional image constructing processor 82 analyzes the anterior segment image Fn to extract the slit light projected region An. The extraction of the slit light projected region An is performed with reference to the brightness information assigned to the pixels, and typically includes thresholding. From the extraction processing, the slit light projected region image Gn (where n=1, 2, . . . , N) can be obtained. The slit light projected region image Gn includes (only) the slit light projected region An. FIG. 8 shows an example of the plurality of slit light projected region images G1 to GN constructed in this way respectively from the plurality of anterior segment images F1 to FN.

If the slit light projected region image Gn contains an artifact, the artifact can be eliminated from the slit light projected region image Gn by, for example, any known image processing or image processing according to another embodiment example. Further, distortion correction described in another embodiment example may be applied to the anterior segment image Fn or the slit light projected region image Gn.

The three dimensional image constructing processor 82 constructs a three dimensional image on the basis of at least part of the plurality of slit light projected region images G1 to GN. Details of the three dimensional image and the three dimensional image construction of the present embodiment example will be described in another embodiment example.

Some advantageous technical effects achieved by the present embodiment example will be described.

As shown in FIG. 5, for example, the left photography optical axis 30La and the right photography optical axis 30Ra are tilted in mutually opposite directions with respect to the illumination optical axis 20a in the present embodiment example. In addition, the data processor 8A of the present embodiment example includes the image selecting processor 81. The image selecting processor 81 judges whether at least one of two images substantially simultaneously acquired by the left photography system 30L and the right photography system 30R contains an artifact. If only one of the two images is judged to contain an artifact, the image selecting processor 81 selects the other image of the two images, that is, an image that does not contain any artifact.

Such a configuration makes it possible to select an image that does not contain any artifact (e.g., a front reflection image, etc.) that interferes with observation and diagnosis.

Further, the data processor 8A of the present embodiment example includes the three dimensional image constructing processor 82. The three dimensional image constructing processor 82 constructs a three dimensional image representing the anterior segment of the subject's eye E based on an image group including one or more of the images selected by the image selecting processor 81 from the plurality of images acquired by the left photography system 30L and the plurality of images acquired by the right photography system 30R.

With such a configuration, a three dimensional image of the anterior segment can be constructed based on an image group that does not contain any artifact which interferes with observation and diagnosis.

Fourth Embodiment Example

The present embodiment example describes a configuration example of the processing system applicable to the slit lamp microscope 1 of the first embodiment example.

In the photography system 3 of the present embodiment example, the left photography optical axis 30La and the right photography optical axis 30Ra may be tilted in mutually opposite directions with respect to the illumination optical axis 20a, as shown in FIG. 5 described in the second embodiment example. Alternatively, the two photography optical axes may be arranged (oriented) in the same direction with respect to the illumination optical axis. In the case where the two photography optical axes are arranged in the same direction, the angle formed by one of the two photography optical axes and the illumination optical axis, and the angle formed by the other photography optical axis and the illumination optical axis are different from each other. Further, in either case, the relative position of one of the photography optical axes with respect to the illumination optical axis and the relative position of the other photography optical axis with respect to the illumination optical axis are different from each other. The processing system of the present embodiment example executes the following processing related to an artifact.

Figure 9:
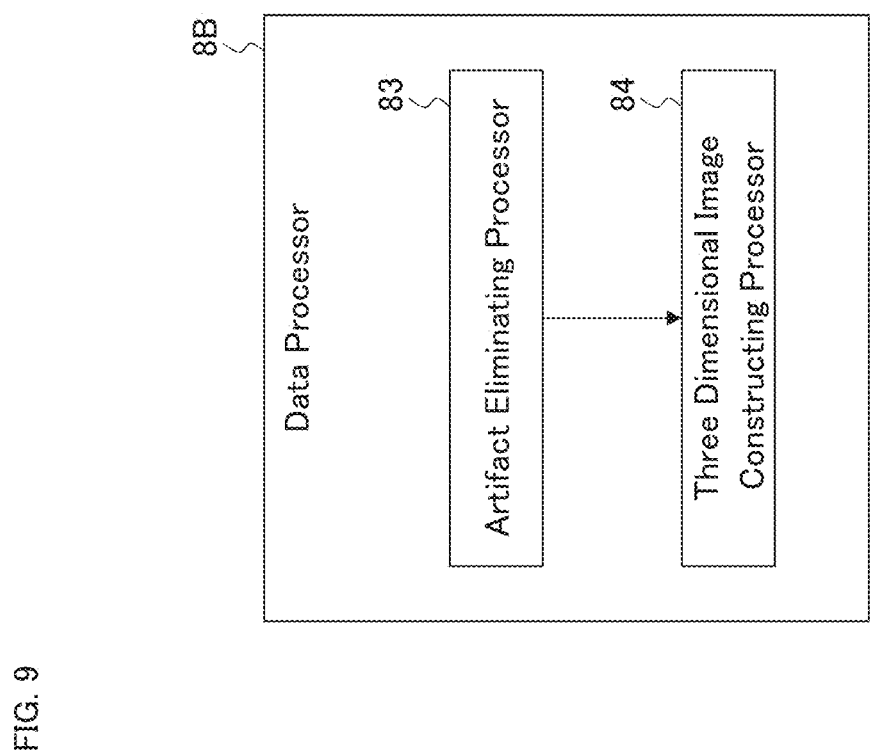
FIG. 9 is a schematic diagram illustrating the configuration of the slit lamp microscope according to the embodiment example.

The data processor 8B shown in FIG. 9 is an example of the data processor 8 of the first embodiment example. The data processor 8B includes the artifact eliminating processor 83.

The artifact eliminating processor 83 is configured to judge whether at least one of two images substantially simultaneously acquired by the left photography system 30L and the right photography system 30R contains an artifact, by comparing the two images. Here, the two images substantially simultaneously acquired by the left photography system 30L and the right photography system 30R are, for example, associated with each other by the pairing of images described above.

As described above, the position of one of the two photography optical axes with respect to the illumination optical axis and the position of the other photography optical axis with respect to the illumination optical axis are different from each other in the present embodiment example. Therefore, the position of an artifact in the image acquired by one of the photography system (e.g., the left photography system 30L) and the position of an artifact in the image acquired by the other of the photography systems (e.g., the right photography system 30R) are different from each other. Alternatively, only one of the two images being compared contains an artifact.

The artifact eliminating processor 83 analyzes each of the two images to judge if it contains an artifact. The artifact judgement is executed in the same manner as the image selecting processor 81 of the third embodiment example, for example.

If only one of the two images contains an artifact, the artifact eliminating processor 83 may either eliminate the artifact from this image, or select the other image that does not contain any artifact as in the third embodiment example. It should be noted that judging that one of the two images contains an artifact and the other does not contain any artifact corresponds to a comparison of the two images.

If both of the two images contain artifacts, the artifact eliminating processor 83 processes one or both of the two images to eliminate the artifacts.

The artifact eliminating processor 83 may be configured to paste a partial region of another image to the image region from which the artifact has been eliminated. As mentioned above, the two images being compared contain different positions of artifacts, or only one of the two images contains an artifact. Therefore, in the case where the artifact is eliminated from one of the images, a corresponding region in the other image does not contain any artifact. The artifact eliminating processor 83 extracts the corresponding region from the other image and pastes the extracted corresponding region on the image region from which the artifact has been eliminated.

Alternatively, another photography system may be provided like the moving image photography system 40 of the second embodiment example. If this is the case, the artifact eliminating processor 83 may extract a corresponding region from an image of the anterior segment acquired by the another photography system and paste the extracted corresponding region on the image region from which the artifact has been eliminated.

As described in the second embodiment example, the left photography system 30L acquires the first image group by performing repetitive photography in parallel with the movement of the illumination system 20, the left photography system 30L, and the right photography system 30R performed by the movement mechanism 6. Similarly, the right photography system 30R acquires the second image group by performing repetitive photography in parallel with the movement of the illumination system 20, the left photography system 30L, and the right photography system 30R performed by the movement mechanism 6. The repetitive photography is typically moving image photography, and each of the first image group and the second image group is a frame group constituting a moving image. Further, images acquired substantially simultaneously among the first image group and the second image group are paired with each other as described above. The artifact eliminating processor 83 applies the artifact elimination as described above to each of the plurality of image pairs.

The data processor 8B further includes the three dimensional image constructing processor 84. The three dimensional image constructing processor 84 constructs a three dimensional image based on an image group including the image from which the artifact is eliminated by the artifact eliminating processor 83. The image group may include only at least part of the plurality of images processed by the artifact eliminating processor 83, or may further include one or more other images. Details of the three dimensional image and the three dimensional image construction of the present embodiment example will be described in another embodiment example.

Some advantageous technical effects achieved by the present embodiment example will be described.

The data processor 8B of the present embodiment example includes the artifact eliminating processor 83. The artifact eliminating processor 83 judges whether at least one of two images substantially simultaneously acquired by the left photography system 30L and the right photography system 30R contains an artifact by comparing the two images. If the at least one of the two images is judged to contain an artifact, the artifact eliminating processor 83 eliminates the artifact.

Such a configuration makes it possible to construct an image that does not contain any artifact (e.g., a front reflection image, etc.) that interferes with observation and diagnosis.

Further, the data processor 8B of the present embodiment example includes the three dimensional image constructing processor 84. The three dimensional image constructing processor 84 constructs a three dimensional image representing the anterior segment of the subject's eye E based on an image group including an image from which the artifact is eliminated by the artifact eliminating processor 83.

With such a configuration, a three dimensional image of the anterior segment can be constructed based on an image group that does not contain artifacts which interfere with observation and diagnosis.

Fifth Embodiment Example

The present embodiment example describes a configuration example of the processing system applicable to the slit lamp microscope 1 of the first embodiment example. In the third and fourth embodiment examples, typically, processing related to artifacts is applied to two images substantially simultaneously acquired by the first photography system and the second photography system, and a three dimensional image is constructed based on an image group containing no artifacts. On the other hand, three dimensional image construction may be performed without the processing related to artifacts. The present embodiment example is applicable in such a case.

Figure 10:
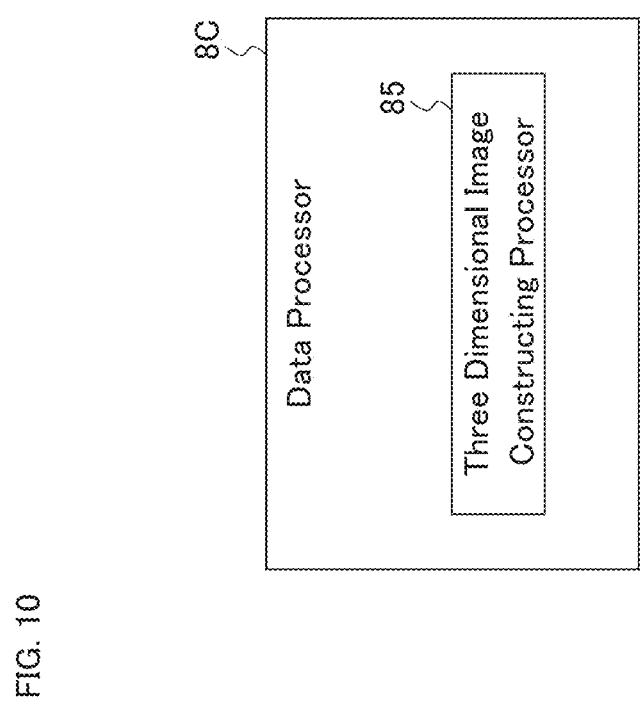
FIG. 10 is a schematic diagram illustrating the configuration of the slit lamp microscope according to the embodiment example.

The data processor 8C shown in FIG. 10 is an example of the data processor 8 of the first embodiment example. The data processor 8C includes the three dimensional image constructing processor 85.

In the first example of the present embodiment example, as described in the first embodiment example, the photography system 3 acquires a plurality of images of the anterior segment of the subject's eye E by performing repetitive photography in parallel with the movement of the illumination system 2 and the photography system 3 performed by the movement mechanism 6.

The three dimensional image constructing processor 85 may construct a three dimensional image based on the plurality of images acquired by the photography system 3. An image group used for the three dimensional image construction may include only at least part of the plurality of images acquired by the photography system 3, or may further include one or more images other than the plurality of images. Details of the three dimensional image and the three dimensional image construction of the present embodiment example will be described in another embodiment example.

The second example of the present embodiment example is described below. As described in the second embodiment example, the first image group is acquired by the left photography system 30L performing repetitive photography in parallel with the movement of the illumination system 20, the left photography system 30L, and the right photography system 30R performed by the movement mechanism 6. Similarly, the second image group is acquired by the right photography system 30R performing repetitive photography in parallel with the movement of the illumination system 20, the left photography system 30L, and the right photography system 30R performed by the movement mechanism 6. Images acquired substantially simultaneously among the first image group and the second image group are paired with each other.

The three dimensional image constructing processor 85 may construct a three dimensional image based on the first image group acquired by the left photography system 30L. The image group used for this three dimensional image construction may include only at least part of the first image group, or may further include one or more images other than the first image group. Similarly, the three dimensional image constructing processor 85 may construct a three dimensional image based on the second image group acquired by the right photography system 30R. The image group used for this three dimensional image construction may include only at least part of the second image group, or may further include one or more images other than the second image group. Details of the three dimensional image and the three dimensional image construction of the present embodiment example will be described in another embodiment example.

Some advantageous technical effects achieved by the present embodiment example will be described.

The data processor 8C of the present embodiment example includes the three dimensional image constructing processor 85. The three dimensional image constructing processor 85 constructs a three dimensional image based on a plurality of images acquired by the photography system 3. The photography system 3 may include both the left photography system 30L and the right photography system 30R, or may include only a single photography system corresponding to one of the left photography system 30L and the right photography system 30R.

According to such a configuration, a three dimensional image representing a three dimensional region in the anterior segment of the subject's eye E can be constructed. The three dimensional image thus constructed is useful for observation and diagnosis.

Sixth Embodiment Example

The present embodiment example is applicable to the cases where a three dimensional image of the anterior segment can be constructed as in the third to fifth embodiment examples.

As described above, a three dimensional image is constructed from a plurality of images sequentially obtained by scanning with slit light. Constructing a three dimensional image from a plurality of images requires arranging the plurality of images. However, it is difficult to arrange the plurality of images with high accuracy and high precision because the plurality of images are acquired at different times. The present embodiment example is devised to solve such a problem.

Figure 11:
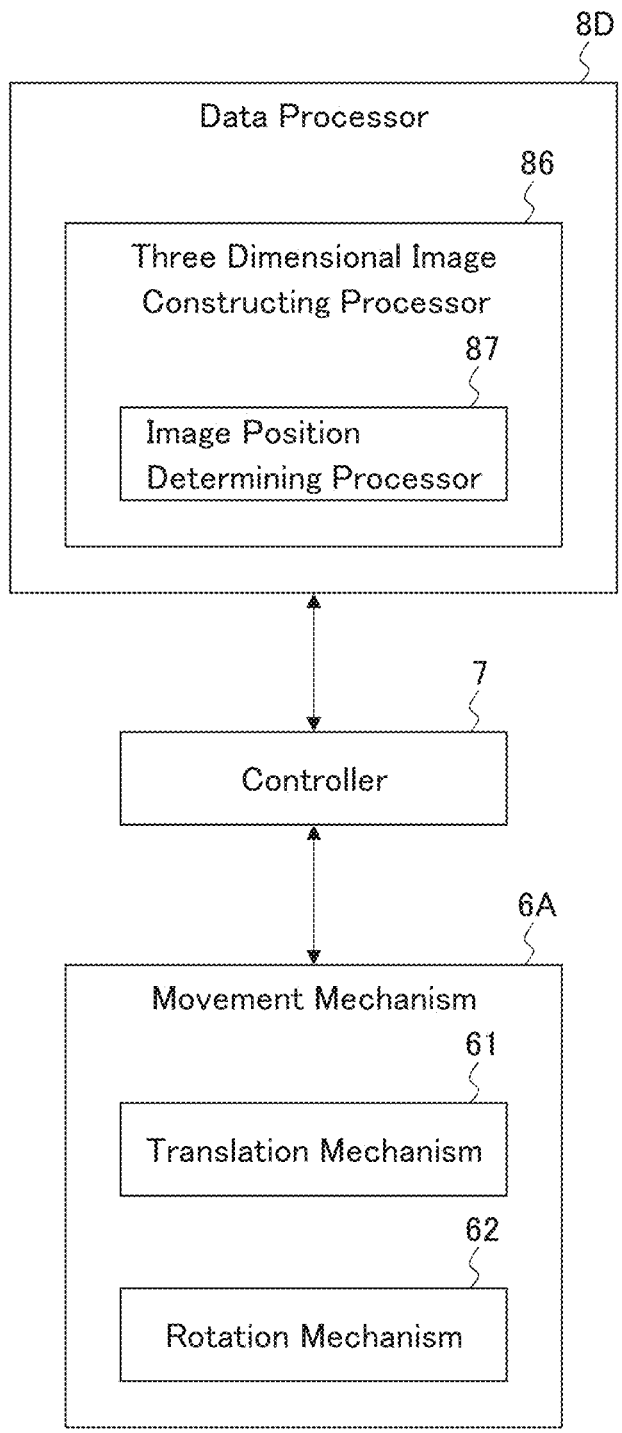
FIG. 11 is a schematic diagram illustrating the configuration of the slit lamp microscope according to the embodiment example.

The controller 7 shown in FIG. 11 may be the same as that of the first embodiment example. The movement mechanism 6A is an example of the movement mechanism 6 of the first embodiment example, and includes the translation mechanism 61 and the rotation mechanism 62. The data processor 8D includes the three dimensional image constructing processor 86. The three dimensional image constructing processor 86 is an example of the three dimensional image constructing processor 82 of the third embodiment example, an example of the three dimensional image constructing processor 84 of the fourth embodiment example, and the three dimensional image constructing processor 85 of the fifth embodiment example. The three dimensional image constructing processor 86 includes the image position determining processor 87.

In the case where the configuration shown in FIG. 1 of the first embodiment example is employed, the translation mechanism 61 integrally moves the illumination system 2 and the photography system 3 in the X direction in order to scan the anterior segment with the slit light.

In the case where the configuration shown in FIG. 5 of the second embodiment example is employed, the translation mechanism 61 integrally moves the illumination system 20, the left photography system 30L, and the right photography system 30R in the X direction in order to scan the anterior segment with the slit light.

In the case where the configuration shown in FIG. 1 of the first embodiment example is employed, the rotation mechanism 62 integrally rotates the illumination system 2 and the photography system 3 about the illumination optical axis 2a.

In the case where the configuration shown in FIG. 5 of the second embodiment example is employed, the rotation mechanism 62 integrally rotates the illumination system 20, the left photography system 30L, and the right photography system 30R about the illumination optical axis 20a.

As a result of the rotation, the orientation of the slit light being projected onto the anterior segment of the subject's eye E can be rotated, and the photographing direction can also be rotated by the same angle as the rotation angle of the orientation of the slit light.

In the case where the configuration shown in FIG. 1 of the first embodiment example is employed, an anterior segment scan with the slit light is performed and the photography system 3 acquires the plurality of images when the illumination system 2 and the photography system 3 are arranged in the first rotation position.

In the case where the configuration shown in FIG. 5 of the second embodiment example is employed, an anterior segment scan with the slit light is performed, and the left photography system 30L acquires the first image group and the right photography system 30R acquires the second image group when the illumination system 20, the left photography system 30L, and the right photography system 30R are arranged in the first rotation position.

The first rotation position may be, for example, a rotation position where the longitudinal direction of the slit light projected onto the anterior segment coincides with the body axis direction of the subject (Y direction).

In the case where the configuration shown in FIG. 1 of the first embodiment example is employed, the photography system 3 acquires an image of the anterior segment onto which the slit light is being projected by the illumination system 20 when the illumination system 2 and the photography system 3 are arranged in the second rotation position different from the first rotation position.

In the case where the configuration shown in FIG. 5 of the second embodiment example is employed, each of the photography system 30R and the right photography system 30R acquires an image of the anterior segment onto which the slit light is being projected by the illumination system 20 when the illumination system 20, the left photography system 30L, and the right photography system 30R are arranged in the second rotation position different from the first rotation position.

The second rotation position may be, for example, a rotation position where the longitudinal direction of the slit light projected onto the anterior segment coincides with the left-right direction (X direction). As a result of this, photography is performed once or more in addition to the anterior segment scan performed in the first rotation position. In this additional photography, the orientation of the slit light is different from that during the anterior segment scan. Typically, the orientation of the slit light in the additional photography may be set such that the slit light in the additional photography passes through all slit light projected regions in the anterior segment scan.

The image position determining processor 87 is configured to determine relative positions of the plurality of images of the anterior segment acquired in the first rotation position, based on the image of the anterior segment acquired in the second rotation position. The image position determination is a process of adjusting the arrangement of the plurality of images acquired in the first rotation position, with reference to the image acquired in the second rotation position.

In some examples, the image position determining processor 87 analyzes each image acquired in the first rotation position and the image acquired in the second rotation position to identify a common region (intersection) between the two images. Further, the image position determining processor 87 determines the relative position of each image acquired in the first rotation position and the image acquired in the second rotation position, with reference to the common region identified for the two images.

By applying the above processes to all the images acquired in the first rotation position, all the images acquired in the first rotation position are arranged with reference to the image acquired in the second rotation position. In other words, the relative positions of all the images acquired in the first rotation position are determined through the mediation of the image acquired in the second rotation position.

The processing executed by the image position determining processor 87 may include any kind of information processing such as image correlation processing, segmentation, pattern matching, processing using artificial intelligence, and processing using cognitive computing.

The three dimensional image constructing processor 86 arranges the plurality of images acquired in the first rotation position in a single three dimensional coordinate system based on the relative positions determined by the image position determining processor 87, and constructs a three dimensional image from the plurality of images arranged in the single three dimensional coordinate system.

Figure 12:
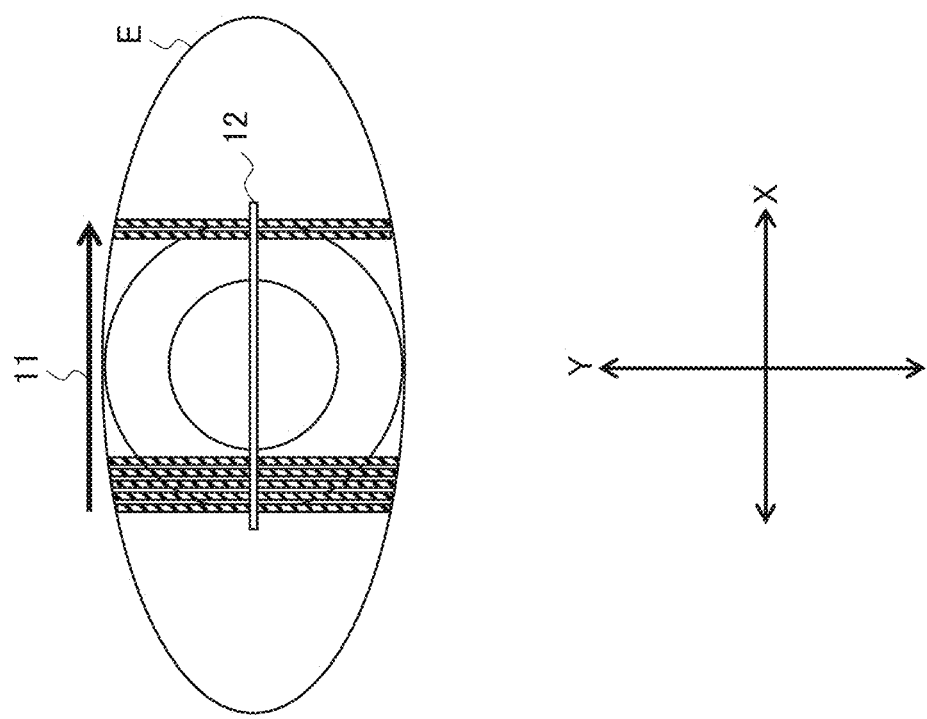
FIG. 12 is a schematic diagram for describing the operation of the slit lamp microscope according to the embodiment example.

FIG. 12 shows an example of the projection positions of the slit light in the present embodiment example. FIG. 12 represents a state in which the anterior segment is viewed from the front. When the illumination system 2 and the photography system 3 are placed in the first rotation position, the plurality of slit light projected regions in the anterior segment scan corresponds to the plurality of strip-shaped regions arranged in the X direction. Here, the longitudinal direction of each of the strip-shaped regions corresponds to the Y direction. In the anterior segment scan of the present example, the slit light is sequentially projected onto the strip-shaped regions in the order indicated by the arrow 11. Photography is performed at least once during the slit light is being projected onto each one of the strip-shaped regions.

On the other hand, the reference character 12 indicates the position of the slit light projected onto the anterior segment when the illumination system 2 and the photography system 3 are arranged in the second rotation position. The slit light projected region 12 corresponding to the second rotation position is a strip-shaped region whose longitudinal direction corresponds to the X direction. In other words, the orientation of the slit light projected onto the anterior segment in the first rotation position and the orientation of the slit light projected onto the anterior segment in the second rotation position are orthogonal to each other in the present example. Note that the relationship between the orientation of the slit light projected onto the anterior segment in the first rotation position and the orientation of the slit light projected onto the anterior segment in the second rotation position is not limited to this example. It is sufficient as long as their orientations are different from one another.

While the case described here is in which a configuration including the illumination system 2 and the photography system 3 is employed, the same applies to the case where a configuration including the illumination system 20, the left photography system 30L, and the right photography system 30R is employed.

As described above, the present example carries out both the anterior segment scan in the first rotation position and the photography in the second rotation position. Here, the timing of performing the anterior segment scan and the timing of performing the photography may be optional. Examples of the timings may include the followings: performing the anterior segment scan in the first rotation position after having performed the photography in the second rotation position; performing the photography in the second rotation position after having performed the anterior segment scan in the first rotation position; and performing the photography in the second rotation position in the middle of the anterior segment scan in the first rotation position.

Some advantageous technical effects achieved by the present embodiment example will be described.

The movement mechanism 6A of the present embodiment example includes the rotation mechanism 62 configured to integrally rotate the illumination system 2 (20) and the photography system 3 (30L, 30R) about the illumination optical axis 2a (20a). The photography system 3 (30L, 30R) acquires a plurality of images of the anterior segment onto which the slit light is being projected when the illumination system 2 (20) and the photography system 3 (30L, 30R) are placed in the first rotation position. Further, the photography system 3 (30L, 30R) acquires an image of the anterior segment onto which the slit light is being projected by the illumination system 2 (20) when the illumination system 2 (20) and the photography system 3 (30L, 30R) are placed in the second rotation position different from the first rotation position. The image position determining processor 87 is configured to determine relative positions between the plurality of images acquired in the first rotation position based on the image acquired in the second rotation position. The three dimensional image constructing processor 86 constructs a three dimensional image by performing position matching (registration) between the plurality of images based on the relative positions determined.

According to the configuration described above, registration (position matching, position adjustment) between the plurality of images acquired in the first rotation position can be executed with reference to the image acquired in the second rotation position. Such registration contributes to improving accuracy and precision in the three dimensional image construction.

Note that the determination of the relative positions of the plurality of images acquired in the first rotation position of the present embodiment example may not only mean the determination of the relative positions of the plurality of images themselves, but also mean the determination of the relative positions of the plurality of slit light projected regions extracted from the plurality of images. Therefore, the present embodiment example may include both the case of performing the extraction of the slit light projected regions after the determination of the relative positions of the plurality of images and the case of performing the determination of the relative positions of the slit light projected regions after the extraction of the slit light projected regions from the plurality of images.

Further, the present embodiment example may perform the determination of the relative positions of an image group selected from the plurality of images acquired in the first rotation position, as in the case where the third embodiment example is employed. Further, the present embodiment example may perform the determination of the relative positions of an image group obtained by processing the plurality of images acquired in the first rotation position, as in the case where the fourth embodiment example is employed. Therefore, the present embodiment example may include both the case of performing the selection or the processing of images after the determination of the relative positions of the plurality of images have been determined and the case of performing the determination of the relative positions of selected images or processed images after the selection or processing of images.

Seventh Embodiment Example

The present embodiment example gives a description of three dimensional image construction briefly described in any of the third to sixth embodiment examples or the like.

Figure 13:
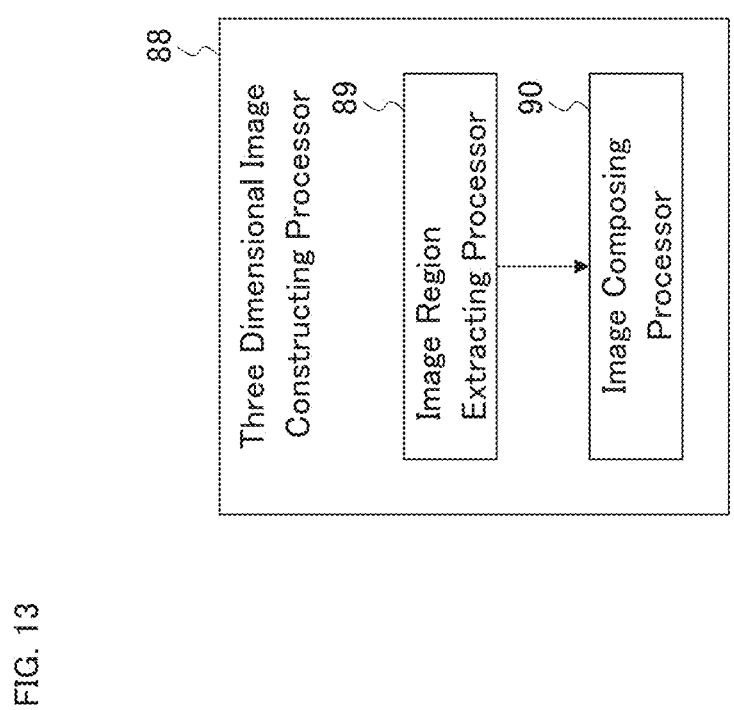
FIG. 13 is a schematic diagram illustrating the configuration of the slit lamp microscope according to the embodiment example.

The three dimensional image constructing processor 88 shown in FIG. 13 includes the image region extracting processor 89 and the image composing processor 90.

In the case where the configuration shown in FIG. 1 of the first embodiment example is employed, the image region extracting processor 89 extracts image regions corresponding to the regions onto which the slit light from the illumination system 2 is projected, respectively from the plurality of images acquired by the photography system 3 in parallel with the movement of the illumination system 2 and the photography system 3. The image region extracted is a two dimensional image region or a three dimensional image region.

In the case where the configuration shown in FIG. 5 of the second embodiment example is employed, the image region extracting processor 89 is capable of extracting image regions corresponding to the regions onto which the slit light from the illumination system 20 is projected, respectively from the plurality of images acquired by the left photography system 30L in parallel with the movement of the illumination system 20, the left photography system 30L, and the right photography system 30R. In addition, the image region extracting processor 89 is capable of extracting image regions corresponding to the regions onto which the slit light from the illumination system 20 is projected, respectively from the plurality of images acquired by the right photography system 30R in parallel with the movement of the illumination system 20, the left photography system 30L, and the right photography system 30R. The image region extracted in this example as well is a two dimensional image region or a three dimensional image region.

The processing executed by the image region extracting processor 89 is carried out, for example, in the same manner as the process of extracting the slit light projected region An from the anterior segment image Fn and the process of constructing the slit light projected region image Gn, as described with reference to FIG. 3 and FIG. 8 in the third embodiment example.

The image composing processor 90 constructs a three dimensional image by composing the plurality of image regions (the plurality of slit light projected regions) extracted respectively from the plurality of images by the image region extracting processor 89. The image composing processor 90 may include, for example, a process of embedding the plurality of slit light projected regions in a single three dimensional coordinate system, and may further include a process of processing the plurality of slit light projected regions embedded in the single three dimensional coordinate system. For example, noise elimination, noise reduction, voxelization, and the like may be performed in the processing of the plurality of slit light projected regions.

The determination of the relative positions of the plurality of slit light projected regions may be performed by executing the process according to the sixth embodiment example, before the composition of the plurality of slit light projected regions.

The image region extracting processor 89 may be configured to extract an image region corresponding to both a slit light projected region and a predetermined site of the anterior segment, from each of the plurality of images. The predetermined site of the anterior segment may be, for example, a site (region, area) defined by the anterior corneal surface and the posterior crystalline lens surface.

In some examples, the image region extracting processor 89 first performs thresholding of the brightness information to identify a slit light projected region, and also performs segmentation to identify an image region corresponding to the anterior corneal surface and an image region corresponding to the posterior crystalline lens surface.

Next, the image region extracting processor 89 identifies an image region corresponding to a site defined by the anterior corneal surface and the posterior crystalline lens surface (referred to as a target image region) based on the image region corresponding to the anterior corneal surface and the image region corresponding to the posterior crystalline lens surface.

Subsequently, the image region extracting processor 89 identifies a common region between the slit light projected region and the target image region. In other words, the image region extracting processor 89 identifies an image region included in both the slit light projected region and the target image region. With such common region identification, for example, a two dimensional image region (cross section) or a three dimensional image region (slice) in the target image can be identified which corresponds to the slit light projected regions in the area from the anterior corneal surface to the posterior crystalline lens surface.

The image composition is performed after the extraction of the slit light projected region in the present example, but conversely, the extraction of the slit light projected region may be performed after the image composition. Further, the image region to be extracted is not limited to a slit light projected region, and the above predetermined site is not limited to a site from the anterior corneal surface to the posterior crystalline lens surface.

According to the configuration of the present embodiment example, a three dimensional image of a desired site of the anterior segment can be acquired from a plurality of images obtained by an anterior segment scan using slit light. In particular, a three dimensional image can be constructed that represents the slit light projected regions, which are the main observation targets in the slit lamp microscope examination.

In addition, a three dimensional image can be constructed that represents a site from the anterior corneal surface to the posterior crystalline lens surface, which is the main observation target of the anterior segment.

Eighth Embodiment Example

The present embodiment example gives a description of rendering of an three dimensional image constructed in any of the third to seventh embodiment examples or the like.

Figure 14:
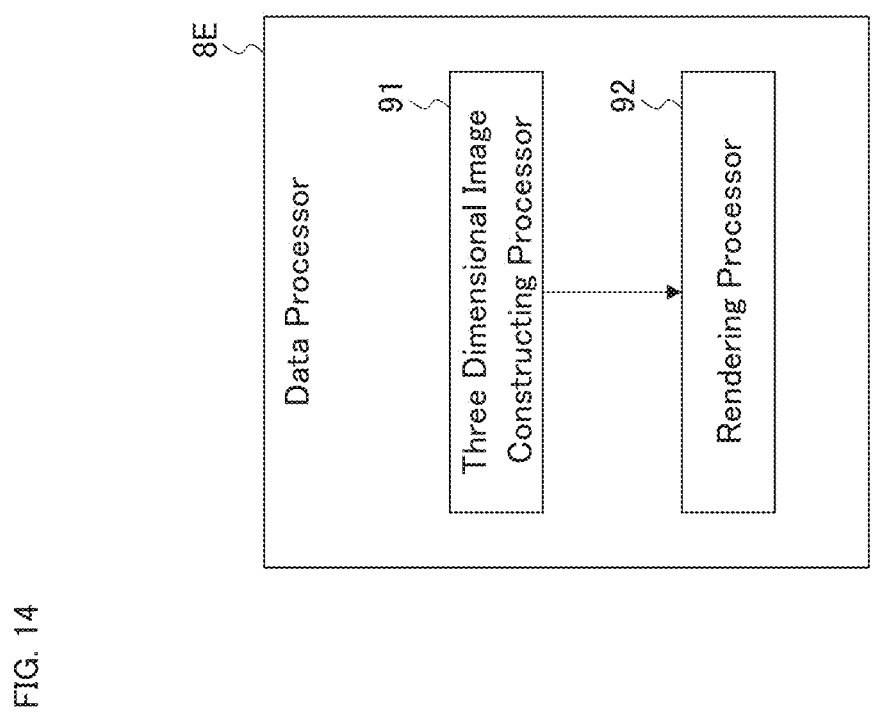
FIG. 14 is a schematic diagram illustrating the configuration of the slit lamp microscope according to the embodiment example.

The data processor 8E shown in FIG. 14 includes the three dimensional image constructing processor 91 and the rendering processor 92. The three dimensional image constructing processor 91 may be any of the followings, for example: the three dimensional image constructing processor 82 of the third embodiment example; the three dimensional image constructing processor 84 of the fourth embodiment example; the three dimensional image constructing processor 85 of the fifth embodiment example; the three dimensional image constructing processor 86 of the sixth embodiment example; and the three dimensional image constructing processor 88 of the seventh embodiment example.

The rendering processor 92 is configured to apply rendering to the three dimensional image constructed by the three dimensional image constructing processor 91 to construct a new image (referred to as a rendered image).

A method or technique of the rendering may be selected accordingly. For example, the rendering may include three dimensional computer graphics. Three dimensional computer graphics is an arithmetic processing that creates an image having a stereoscopic effect by converting a virtual three dimensional object (e.g., a three dimensional image such as stack data or volume data) in a three dimensional space defined by a three dimensional coordinate system, into two dimensional information.

Examples of the rendering include the volume rendering, the maximum intensity projection (MIP), the minimum intensity projection (MinIP), the surface rendering, the multi planar reconstruction (MPR), the projection image construction, and the shadowgram construction. Further examples of the rendering include reproduction of a cross sectional image obtained by a slit lamp microscope and construction of a Scheimpflug image. In addition, the rendering processor 92 may be capable of performing any processing that can be executed along with the rendering.

The rendering processor 92 may identify a region corresponding to a predetermined site in a three dimensional image of the anterior segment. For example, the rendering processor 92 can identify any of a region corresponding to the anterior corneal surface, a region corresponding to the posterior corneal surface, a region corresponding to the anterior crystalline lens surface, and a region corresponding to the posterior crystalline lens surface. Any known image processing, such as segmentation, edge detection, or thresholding, may be performed in such image region identification.

A three dimensional image is typically stack data or volume data. Designation of a cross section of a three dimensional image may be performed manually or automatically.

In the case where manual designation of a cross section of a three dimensional image is employed, the rendering processor 92 applies rendering to the three dimensional image to construct a display image for manual cross section designation. The display image is typically an image representing the entire site to be observed. For example, the display image represents a site between the anterior corneal surface and the posterior crystalline lens surface. The rendering for constructing the display image is typically the volume rendering or the surface rendering.

The controller 7 displays the display image constructed by the rendering processor 92 on a display device (not shown in the drawings). The user designates a desired cross section for the displayed image using an operation device such as a pointing device. The position information of the cross section designated in the display image is input to the rendering processor 92.

Since the display image is a rendered image of the three dimensional image, there is an trivial (natural) positional correspondence relationship between the display image and the three dimensional image. Based on the correspondence relationship, the rendering processor 92 identifies the position of a cross section in the three dimensional image corresponding to the position of the cross section designated in the display image. In short, the rendering processor 92 may designate a cross section for the three dimensional image.

Further, the rendering processor 92 may cut the three dimensional image at the cross section to construct a three dimensional partial image. The rendering processor 92 may apply rendering to the three dimensional partial image to construct an image for display. Some examples of such rendering, some examples of a three dimensional partial image, some examples of a display image based on the three dimensional partial image, and the like will be described later.

In the case where automatic designation of a cross section of a three dimensional image is employed, for example, the data processor 8E (for example, the rendering processor 92) may analyze the three dimensional image to identify a position or a region corresponding to a predetermined site of the anterior segment. For example, the data processor 8E is capable of identifying the anterior corneal surface, identifying the apex position of the anterior corneal surface, identifying the posterior crystalline lens surface, and identifying the apex position of the posterior crystalline lens surface.

Further, the data processor 8E (for example, the rendering processor 92) may apply segmentation to a three dimensional image to identify an image region corresponding to a predetermined site. For example, the data processor 8E may identify a two dimensional region corresponding to the anterior corneal surface, a three dimensional region corresponding to the cornea, a three dimensional region corresponding to the crystalline lens, a two dimensional region corresponding to the posterior crystalline lens surface, a three dimensional region corresponding to the anterior chamber, or the like.

The data processor 8E (for example, the rendering processor 92) may designate a cross section for the three dimensional image based on the position or the region identified in this way. For example, the data processor 8E may be configured to designate a plane passing through both the apex position of the anterior corneal surface and the apex position of the posterior crystalline lens surface as a cross section, or designate a curved surface corresponding to the anterior crystalline lens surface as a cross section.

An image constructed by the rendering processor 92 on the basis of a cross section designated for a three dimensional image is not limited to a three dimensional partial image. For example, the rendering processor 92 may be configured to construct a two dimensional cross sectional image representing a cross section designated for a three dimensional image. Some examples of such rendering, some examples of a two dimensional cross sectional image, some examples of a display image based on a two dimensional cross sectional image, and the like will be described later.

The position information that can be designated for a three dimensional image is not limited to a cross section that is a two dimensional region having a shape of a planar surface or a curved surface. Another example of position information that can be designated in a three dimensional region is a slice. A slice is a three dimensional region having a predetermined thickness, typically a thin plate having an even thickness.

When a slice is designated for a three dimensional image, the rendering processor 92 may construct a three dimensional slice image corresponding to the slice designated. The rendering processor 92 may further apply rendering to the three dimensional slice image to construct an image for display. Some examples of such rendering, some examples of a three dimensional slice image, some examples of a display image based on a three dimensional slice image, and the like will be described later.

Some advantageous technical effects achieved by the present embodiment example will be described.

The present embodiment example includes the rendering processor 92 configured to apply rendering to a three dimensional image constructed by the three dimensional image constructing processor 91, to construct a rendered image. With this, the rendered image constructed on the basis of the three dimensional image constructed by the three dimensional image constructing processor 91 can be displayed, and a user may observe a desired site of the anterior segment.

The rendering method or technique is selected accordingly. For example, in response to designation of a cross section for a three dimensional image, the rendering processor 92 may cut the three dimensional image at the designated cross section to construct a three dimensional partial image. This makes it possible for a user to observe a desired cross section of the anterior segment and grasp the three dimensional morphology of the anterior segment.

In another example, in response to designation of a cross section for a three dimensional image, the rendering processor 92 may construct a two dimensional cross sectional image representing the cross section designated. This makes it possible for a user to observe a desired cross section of the anterior segment.

In yet another example, in response to designation of a slice for a three dimensional image, the rendering processor 92 may construct a three dimensional slice image corresponding to the slice designated. This makes it possible for a user to observe a desired slice of the anterior segment.

Ninth Embodiment Example

In the slit lamp microscope according to any of the first to eighth embodiment examples, the illumination optical axis and the photography optical axis form a predetermined angle, and the illumination system and the photography system function as a Scheimpflug camera. An image obtained by such a slit lamp microscope suffers from distortion. This distortion is typically a keystone distortion (also referred to as trapezoidal distortion, trapezium distortion, or the like).

The present embodiment example describes and treats distortion correction. Typically, the distortion correction is keystone correction (also referred to as trapezoidal correction or the like). The keystone correction is a well-known technique and is disclosed, for example, in Japanese Unexamined Patent Application Publication No. 2017-163465 (US Patent Application Publication No. 2017/0262163).

As described above, in the anterior segment (i.e., in the real space), a slit light projected region is extended in the Z direction and is typically defined in the YZ plane if the slit width is ignored. On the other hand, the optical axis of the photography system is tilted in the X direction with respect to the optical axis of the illumination system that projects the slit light. Therefore, the region to be photographed in the anterior segment is depicted larger as it approaches the surface of the subject's eye and is depicted smaller as it approaches the eye fundus. Thus, keystone distortion in (at least) the Z direction occurs.

Figure 15:
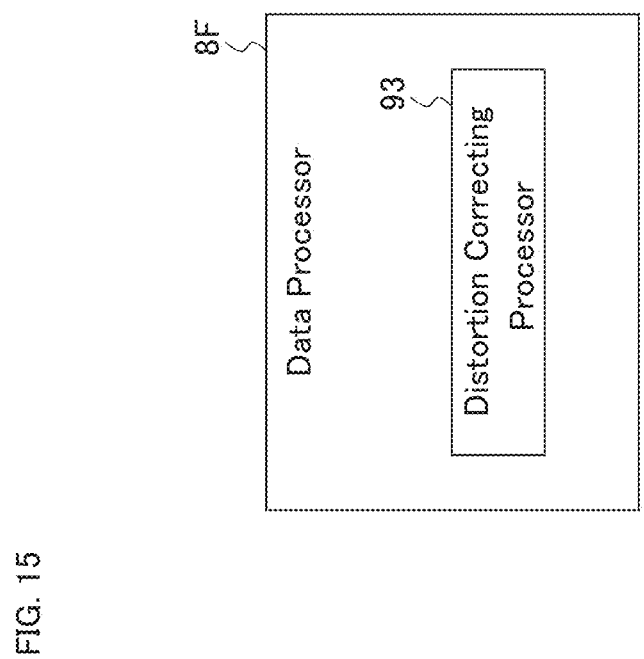
FIG. 15 is a schematic diagram illustrating the configuration of the slit lamp microscope according to the embodiment example.

The data processor 8F shown in FIG. 15 includes the distortion correcting processor 93. The distortion correcting processor 93 may be combined with any of the first to eighth embodiment examples. The distortion correcting processor 93 applies the distortion correction to an anterior segment image acquired by the photography system 3 (the left photography system 30L, the right photography system 30R).

More specifically, the distortion correcting processor 93 applies processing (keystone correction) to correct distortion caused by the optical axis angle θ (θL, θR), which is the angle formed by the illumination optical axis 2a (20a) and the photography optical axis 3a (30La, 30Ra), to at least one of a plurality of images acquired by the photography system 3 (30L, 30R) in parallel with the movement of the illumination system 2 (20) and the photography system 3 (30L, 30R).

An image to which the distortion correction is applied is not limited to an anterior segment image itself acquired by the photography system 3 (30L, 30R), and may be a slit light projected region extracted from an anterior segment image acquired by the photography system 3 (30L, 30R). Therefore, the extraction of a slit light projected region from an anterior segment image may be carried out after performing the distortion correction on the anterior segment image, or conversely, the distortion correction may be performed on a slit light projected region after performing the extraction on the slit light projected region from an anterior segment image.

Further, the distortion correction includes, as in the "image group" in the third and fourth embodiment examples, distortion correction of an anterior segment image selected from the anterior segment images acquired by the photography system 3 (30L, 30R), and distortion correction of an image obtained by processing the anterior segment image acquired by the photography system 3 (30L, 30R). Therefore, the selection or the processing of an anterior segment image may be carried out after performing the distortion correction of the anterior segment image, or conversely, the distortion correction may be performed on a selected image or a processed image may be carried out after performing the selection or the processing on an anterior segment image.

In some typical embodiment examples, the slit lamp microscope includes the optical system shown in FIG. 1 or FIG. 5, and the distortion correcting processor 93 therein corrects distortion in the YZ plane.

In the example shown in FIG. 1, the photography optical axis 3a is tilted in the third direction (X direction) with respect to the illumination optical axis 2a. The third direction (X direction) is orthogonal to both the first direction (Z direction) along the illumination optical axis 2a and the second direction (Y direction) along the longitudinal direction of the slit light. Here, the optical axis angle formed by the illumination optical axis 2*a* and the photography optical axis 3*a* is the angle θ shown in FIG. 1. The distortion correcting processor 93 may apply a process for correcting distortion in the plane (YZ plane) including (spanned by) both the first direction (Z direction) and the second direction (Y direction), to the anterior segment image acquired by the photography system 3.

In the example shown in FIG. 5, the left photography optical axis 30La is tilted, with respect to the illumination optical axis 20*a*, in the third direction (X direction) orthogonal to both the first direction (Z direction) along the illumination optical axis 20*a* and the second direction (Y direction) along the longitudinal direction of the slit light. Here, the optical axis angle formed by the illumination optical axis 20*a* and the left photography optical axis 30La is the angle θL shown in FIG. 5. The distortion correcting processor 93 may apply a process for correcting distortion in the plane (YZ plane) including (spanned by) both the first direction (Z direction) and the second direction (Y direction), to the anterior segment image acquired by the left photography optical axis 30La.

Similarly, the right photography optical axis 30Ra is tilted, with respect to the illumination optical axis 20*a*, in the third direction (X direction) orthogonal to both the first direction (Z direction) along the illumination optical axis 20*a* and the second direction (Y direction) along the longitudinal direction of the slit light. Here, the optical axis angle formed by the illumination optical axis 20*a* and the right photography optical axis 30Ra is the angle θR shown in FIG. 5. The distortion correcting processor 93 may apply a process for correcting distortion in the plane (YZ plane) including (spanned by) both the first direction (Z direction) and the second direction (Y direction) to the anterior segment image acquired by the right photography optical axis 30Ra.

A general and typical method or technique of the keystone correction is carried out in such a way that a trapezoidal shape that is a result of distortion of a rectangle is corrected to its original rectangular shape. While such a standard keystone correction technique may be employed in the present embodiment example, there are cases where employing other keystone correction techniques may be effective, as described below.

Generally, when observing an optical section of an anterior segment (i.e., a slit light projected region) using a slit lamp microscope, the optical axis of an observation system (observation optical axis) of the slit lamp microscope is tilted with respect to the optical axis of an illumination system (illumination optical axis). Therefore, the user observes the optical section extending in the Z direction from a diagonal (oblique) direction. When the optical section is being observed, the angle (observation angle) formed by the illumination optical axis and the observation optical axis is typically a default (preset) value. The default value is 17.5 degrees, 30 degrees, or 45 degrees, for example. The default value is referred to as a reference angle (α).

A correction factor for the distortion correction (keystone correction) may be set based on the reference angle α and the optical axis angle β (θ, θL, θR). A correction factor is set for at least one reference angle α and at least one optical axis angle β (θ, θL, θR). Setting a correction factor may be executed by any of the followings: setting a correction factor for each of the combinations of two or more reference angles and one optical axis angle; setting a correction factor for each of the combination of one reference angle and two or more optical axis angles; and setting a correction factor for each of the combinations of two or more reference angles and two or more optical axis angles. More generally, any discrete or continuous correction factor(s) $C(\alpha, \beta)$ with one or both of the reference angle α and the optical axis angle β as a variable(s) may be set.

The one or more correction factors $C(\alpha, \beta)$ set in this way are stored in the distortion correcting processor 93. The distortion correcting processor 93 may execute a process for correcting distortion based on the correction factor $C(\alpha, \beta)$.

When the correction factor $C(\alpha, \beta)$ provides a plurality of values (factors), the distortion correcting processor 93 or the user designates one or both of the reference angle α and the optical axis angle β. The distortion correcting processor 93 applies a correction factor according to a result of the designation of the angle(s) α and/or β. Such a configuration is employed, for example, in the case where the optical axis angle β of a slit lamp microscope is variable. In such a case, a table or a graph is prepared in which a plurality of correction factors in a variable range of the optical axis angle β is recorded.

Instead of preparing information indicating correction factors, the following configuration may be employed. That is, the distortion correcting processor of the present example stores in advance a predetermined arithmetic formula for calculating a correction factor. Further, the distortion correcting processor of the present example receives an input of the reference angle α and/or the optical axis angle β, and substitutes the input value into the arithmetic formula to calculate a correction factor. The distortion correcting processor of the present example executes distortion correction using the correction factor calculated.

Some advantageous technical effects achieved by the present embodiment example will be described.

The present embodiment example includes the distortion correcting processor 93. In the configuration shown in FIG. 1, the distortion correcting processor 93 may apply a process for correcting the distortion caused by the optical axis angle θ, which is the angle formed by the optical axis 2*a* of the illumination system 2 and the optical axis 3*a* of the photography system 3, to at least one of the plurality of images acquired by the photography system 3 performing repetitive photography in parallel with the movement of the illumination system 2 and the photography system 3 performed by the movement mechanism 6. The same applies to the case where the configuration shown in FIG. 5 or another configuration is adopted.

According to the configuration of the present embodiment example, a proper and adequate image can be provided in which the distortion caused by the optical axis angle θ is corrected.

In the configuration shown in FIG. 1, the optical axis 3*a* of the optical system 4 included in the photography system 3 is tilted, with respect to the optical axis 2*a* of the illumination system 2, in the third direction (X direction) that is orthogonal to both the first direction (Z direction) along the optical axis 2*a* of the illumination system 2 and the second direction (Y direction) along the longitudinal direction of the slit light. The distortion correcting processor 93 may execute a process for correcting the distortion in the plane (YZ plane) spanned by both the first direction and the second direction. The same applies to the case where the configuration shown in FIG. 5 or another configuration is adopted.

According to such a configuration, it is possible to correct keystone distortion occurred in the plane spanned by both the first direction and the second direction.

In the configuration shown in FIG. 1, the distortion correcting processor 93 stores in advance the correction factor C that has been set on the basis of the predetermined reference angle α and the optical axis angle θ. The distortion correcting processor 93 may apply a process for correcting the distortion caused by the optical axis angle θ to an image, based on the correction factor C. The same applies to the case where the configuration shown in FIG. 5 or another configuration is adopted.

Tenth Embodiment Example

In some slit lamp microscope examinations, the size of a tissue, the shape of a tissue, the positional relationship between tissues, and the like may be referred to. Measurement for that purpose will be described in the present embodiment example.

Figure 16:
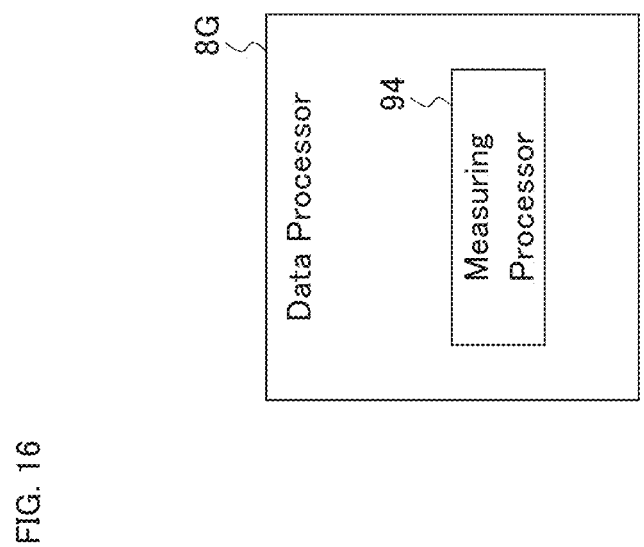
FIG. 16 is a schematic diagram illustrating the configuration of the slit lamp microscope according to the embodiment example.

The data processor 8G shown in FIG. 16 includes the measuring processor 94. The measuring processor 94 may be combined with any of the first to ninth embodiment examples.

In the case where the measuring processor 94 is combined with the slit lamp microscope according to any of the first to ninth embodiment examples, the measuring processor 94 may be configured to analyze an anterior segment image acquired by an anterior segment scan using slit light, to obtain a value of a predetermined measurement parameter (a predetermined measurement value).

In the case where the measuring processor 94 is combined with the slit lamp microscope capable of constructing a three dimensional image, the measuring processor 94 analyzes a three dimensional image constructed by the three dimensional image constructing processor 82 (84, 85, 86, 88, 91) to obtain a predetermined measurement value.

For example, the measurement is performed for obtaining a value of any parameter indicating the morphology of a tissue (e.g., thickness, diameter, area, volume, angle, shape, etc.) and a value of any parameter indicating the relationship between tissues (e.g., distance, direction, etc.). The analysis for the measurement includes segmentation for identifying a tissue or the contour of the tissue, for example.

According to the present embodiment example, measurement can be performed of a parameter that is effective for observation and diagnosis of the anterior segment.

By combining the measuring processor 94 with the ninth embodiment example that is capable of performing distortion correction, the measuring processor 94 may perform measurement based on an image to which the distortion correction has been applied. This makes it possible to improve the accuracy and precision of the measurement.

Eleventh Embodiment Example

In the case where the slit lamp microscope has the function of performing moving image photography of an anterior segment from a fixed position in parallel with an anterior segment scan using slit light, as in the moving image photography system 40 of the second embodiment example, the function according to the present embodiment example may further be combined.

Figure 17:
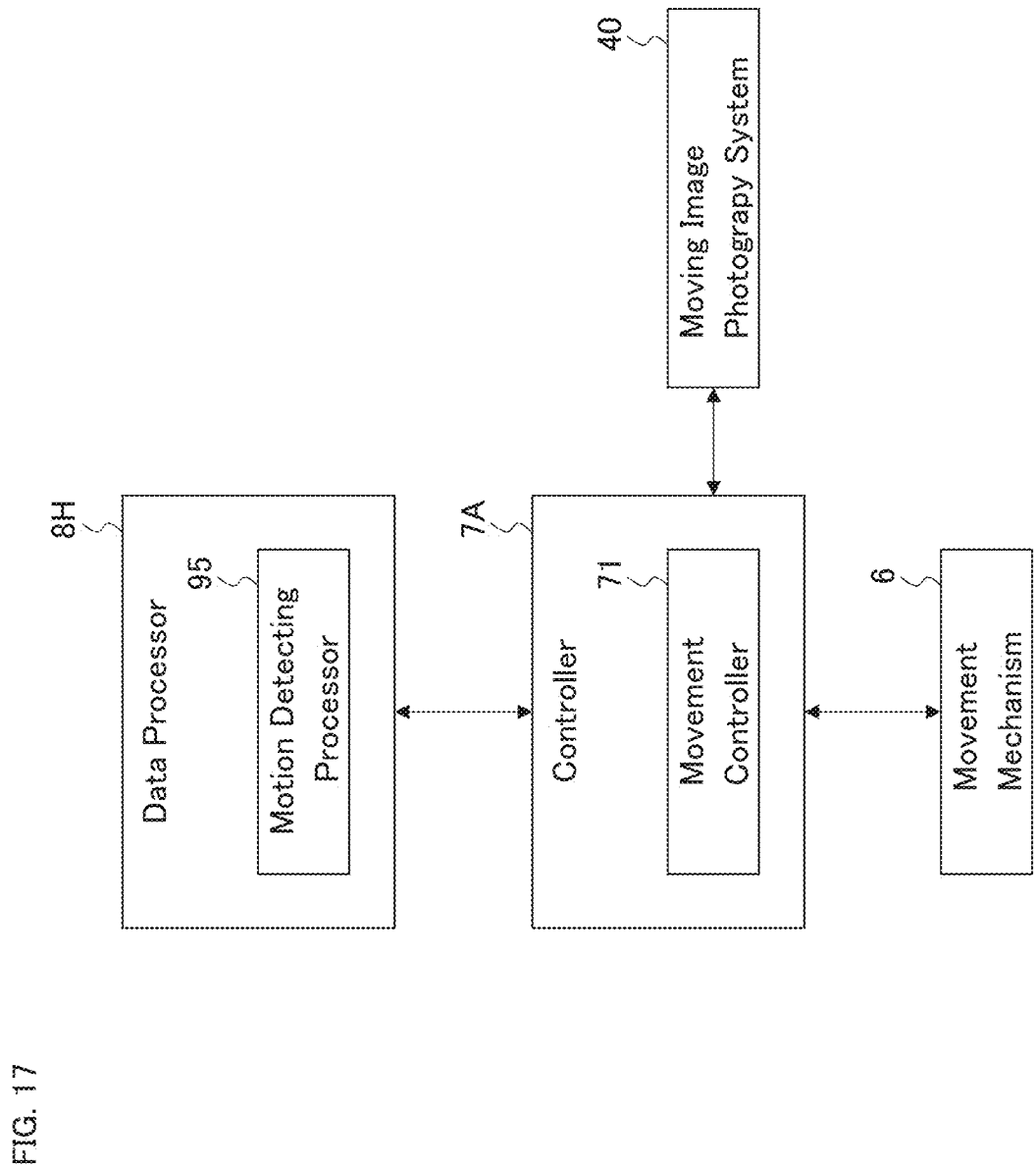
FIG. 17 is a schematic diagram illustrating the configuration of the slit lamp microscope according to the embodiment example.

As shown in FIG. 17, the controller 7A of the present embodiment example includes the movement controller 71, and the data processor 8H includes the motion detecting processor 95. The present embodiment example further includes the moving image photography system 40. The moving image photography system 40 is configured to perform moving image photography of an anterior segment from a fixed position in parallel with an anterior segment scan using slit light.

The motion detecting processor 95 is configured to analyze the moving image acquired by the moving image photography system 40 to detect the motion of the subject's eye E. The motion detection is performed in parallel with the operation of the moving image photography system 40.

For example, the motion detecting processor 95 first analyzes frames sequentially input from the moving image photography system 40, to sequentially identify image regions corresponding to a predetermined site. The predetermined site may typically be the center of the pupil, the center of gravity of the pupil, the contour of the pupil, or the like. The image region identification is performed based on brightness information assigned to pixels. The motion detecting processor 95 may identify an image region with low brightness pixel values in an image of the anterior segment as a pupil region, and then identify the center of gravity or the contour of the pupil region. Alternatively, the motion detecting processor 95 may determine an approximate circle or an approximate ellipse of the identified pupil region, and then identify the center or contour of the approximate circle or the approximate ellipse.

In this way, the motion detecting processor 95 sequentially determines a feature point in each of the frames input from the moving image photography system 40. Further, the motion detecting processor 95 obtains temporal change in the position of the feature point sequentially identified. The motion detecting processor 95 is capable of detecting the motion of the subject's eye E (in real time) by such processing since the position of the moving image photography system 40 is fixed.

The movement controller 71 may control the movement mechanism 6 based on an output from the motion detecting processor 95. More specifically, the motion detecting processor 95 sequentially inputs, to the movement controller 71, information indicating the temporal change in the position of the feature point in the frames sequentially input from the moving image photography system 40. The movement controller 71 controls the movement mechanism 6 according to the information sequentially input from the motion detecting processor 95. The movement control is executed so as to compensate for (so as to cancel, so as to eliminate) the change in the alignment state caused by the motion of the subject's eye E. Such an operation is referred to as tracking.

According to such an embodiment example, when the subject's eye E moves during the anterior segment scan using the slit light, the alignment state can automatically be corrected in response to the movement of the subject's eye E. This makes it possible to conduct an anterior segment scan using slit light without being affected by the motion of the subject's eye.

<Usage Mode>

Some examples of the usage mode of the slit lamp microscope according to the above embodiment examples will be described. Here, the optical system shown in FIG. 5 is employed. Adjustment of the table, the chair, and the chin rest, instructions to start photography, alignment, and other preparation processes are performed in the manner as described above.

To begin with, as described in the sixth embodiment example, the controller 7 controls the rotation mechanism 62 such that the longitudinal direction of the slit light projected onto the anterior segment coincides with the lateral direction (X direction). One of the left photography system 30L and the right photography system 30R photographs the anterior segment onto which the slit light whose longitudinal direction is the lateral direction (X direction) is being projected.

Figure 18:
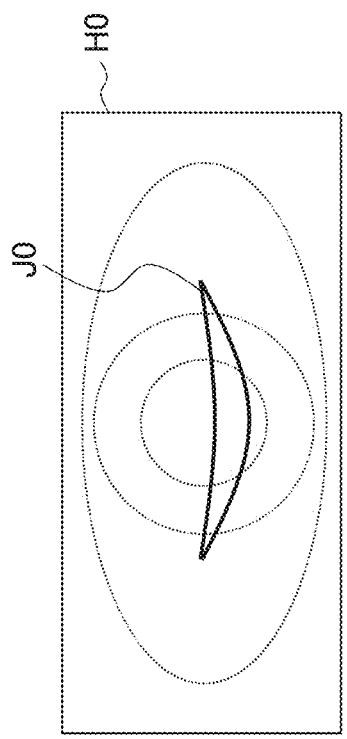
FIG. 18 is a schematic diagram for describing the usage mode of the slit lamp microscope according to the embodiment example.

As a result, the anterior segment image H0 shown in FIG. 18 is acquired. The anterior segment image H0 contains the slit light projected region J0. The slit light projected region J0 is a region of the anterior segment onto which the slit light whose longitudinal direction is the lateral direction (X direction) is projected.

Note that both the left photography system 30L and the right photography system 30R may perform photography of the anterior segment. If this is the case, an image of the slit light projected region taken from diagonally above and an image taken from diagonally below may be obtained.

Next, the controller 7 controls the rotation mechanism 62 such that the longitudinal direction of the slit light projected onto the anterior segment coincides with the vertical direction (Y direction). Then, the controller 7 controls the illumination system 20, the left photography system 30L, the right photography system 30R, and the movement mechanism 6 to perform an anterior segment scan using the slit light. More specifically, each of the left photography system 30L and the right photography system 30R photographs the anterior segment of the subject's eye E in parallel with the movement of the illumination system 20, the left photography system 30L and the right photography system 30R performed by the movement mechanism 6.

Figure 19A:
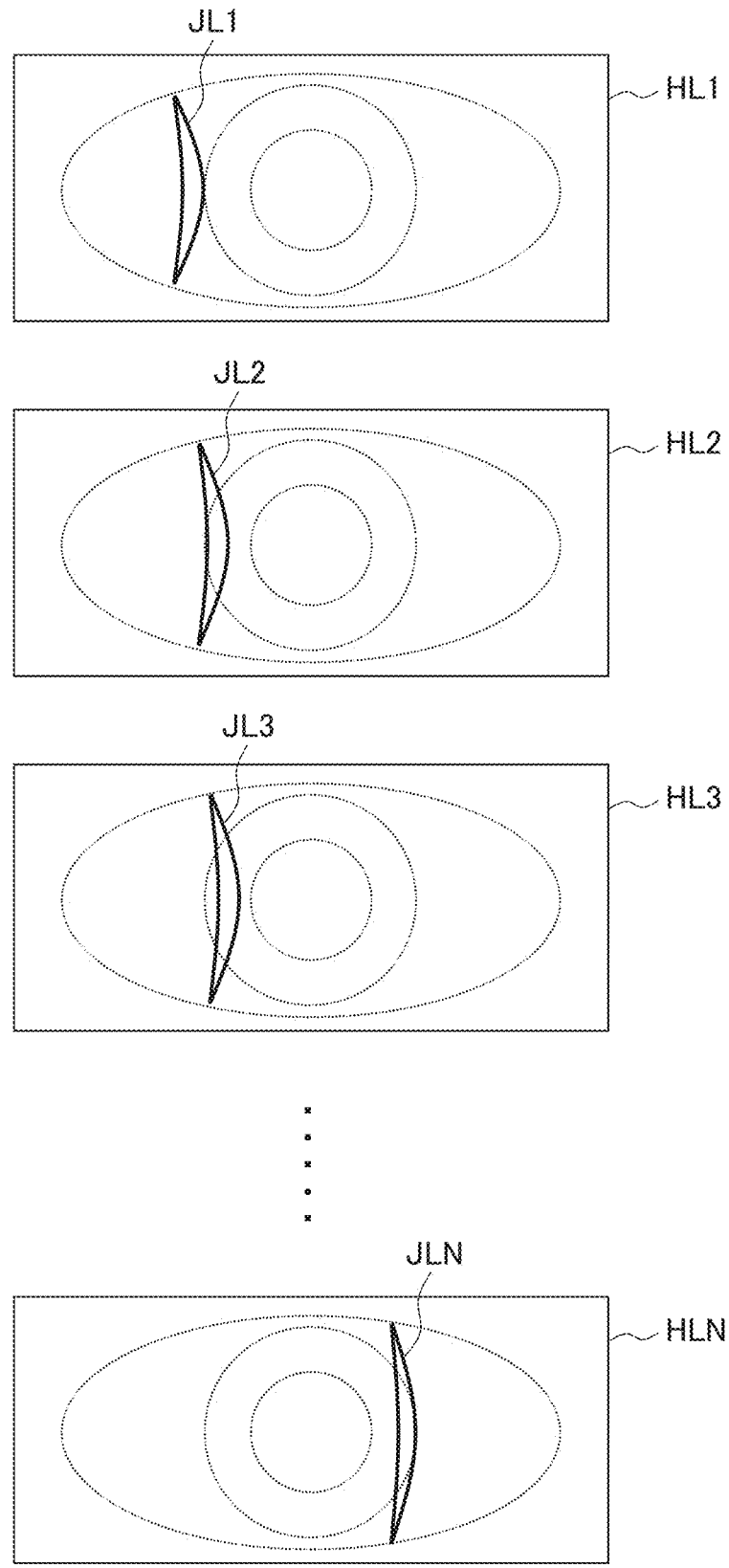
FIG. 19A is a schematic diagram for describing the usage mode of the slit lamp microscope according to the embodiment example.
Figure 19B:
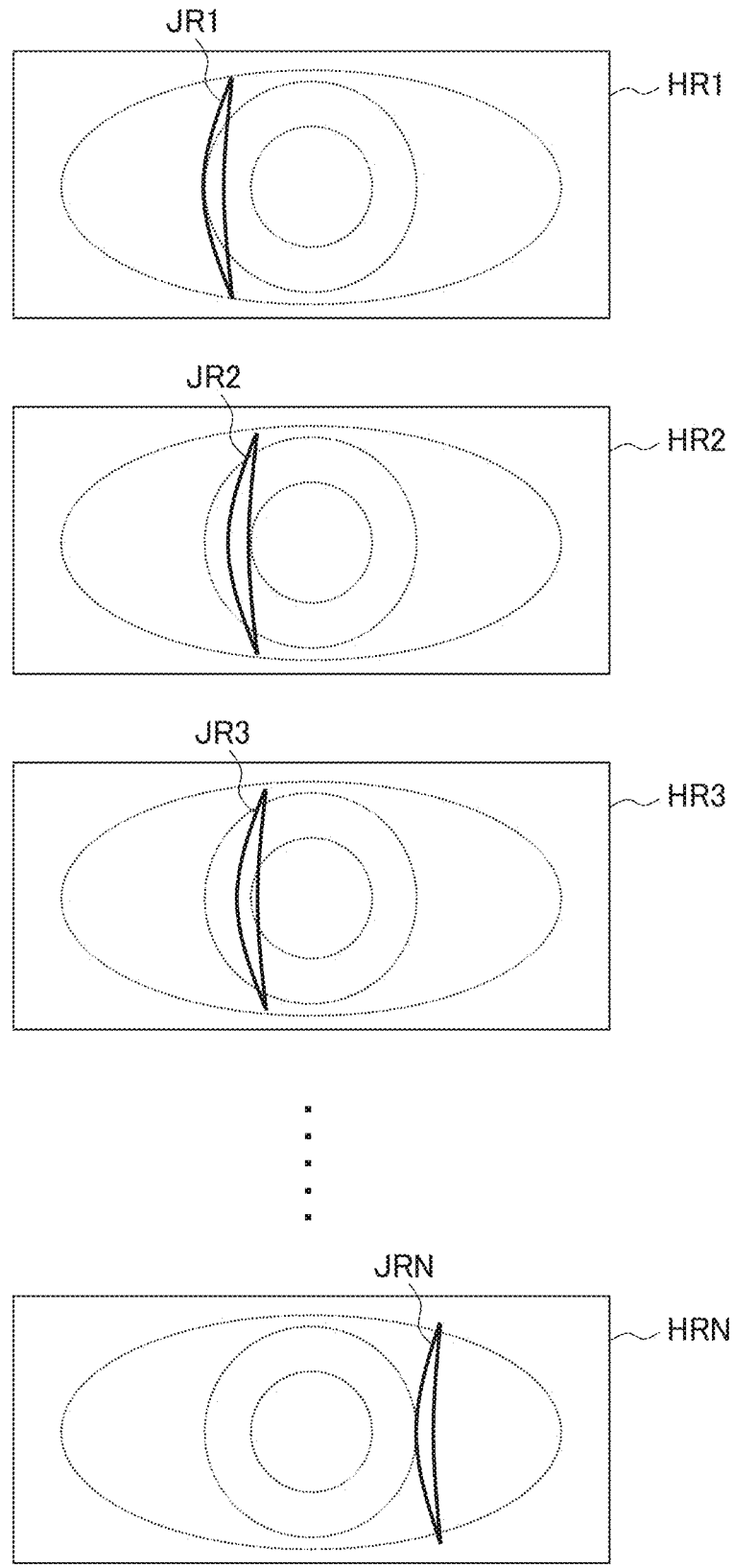
FIG. 19B is a schematic diagram for describing the usage mode of the slit lamp microscope according to the embodiment example.

With the photography in this manner, the left photography system 30L acquires the first image group including the number N of anterior segment images HL1 to HLN shown in FIG. 19A, and the right photography system 30R acquires the second image group including the number N of anterior segment images HR1 to HRN shown in FIG. 19B. The anterior segment image HLn acquired by the left photography system 30L contains the slit light projected region JLn that is photographed from a diagonally left side (where n=1, 2, . . . , N). Similarly, the anterior segment image HRn acquired by the right photography system 30R contains the slit light projected region JRn that is photographed from a diagonally right side (where n=1, 2, . . . , N).

Here, the anterior segment image HLn and the anterior segment image HRn are associated with each other by the image pairing described above (where n=1, 2, . . . , N). In the actual anterior segment scan, the number N of each of the left and right anterior segment images may be set to 200 or more in consideration of the resolution of a three dimensional image to be constructed later. Incidentally, the number N may be set accordingly.

Figure 20:
FIG. 20 is a photograph for describing the usage mode of the slit lamp microscope according to the embodiment example.
Figure 20:
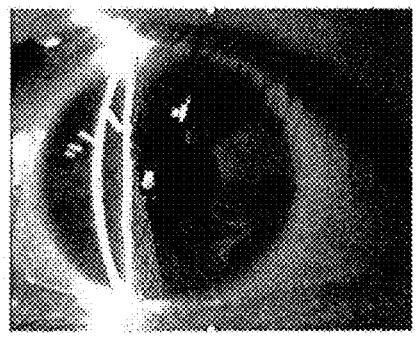
Figure 20:
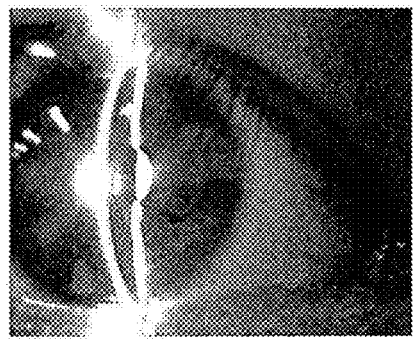
Figure 20:

FIG. 20 shows a series of anterior segment images acquired by an actual anterior segment scan. Each of the anterior segment images includes a slit light projected region that is a high-brightness region.

Figure 21A:
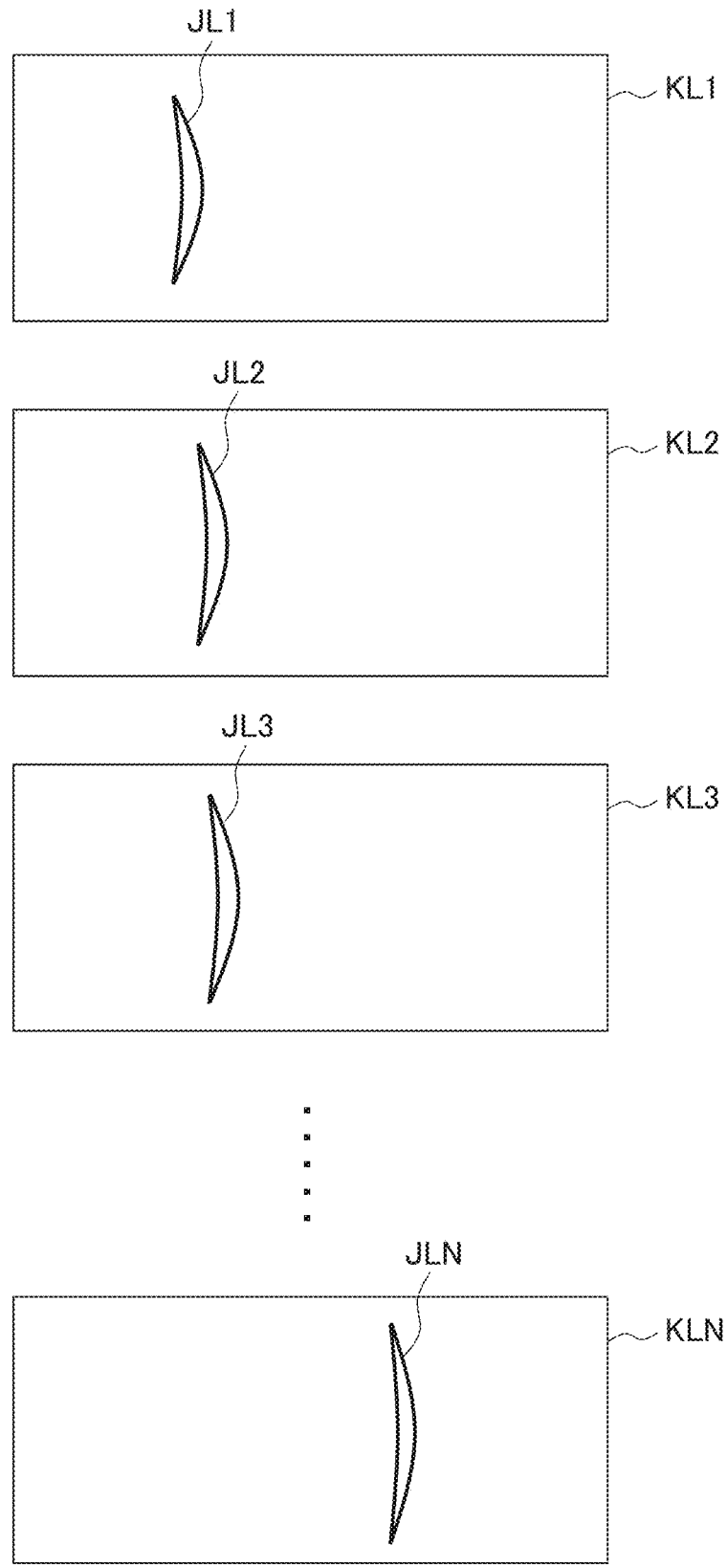
FIG. 21A is a schematic diagram for describing the usage mode of the slit lamp microscope according to the embodiment example.
Figure 21B:
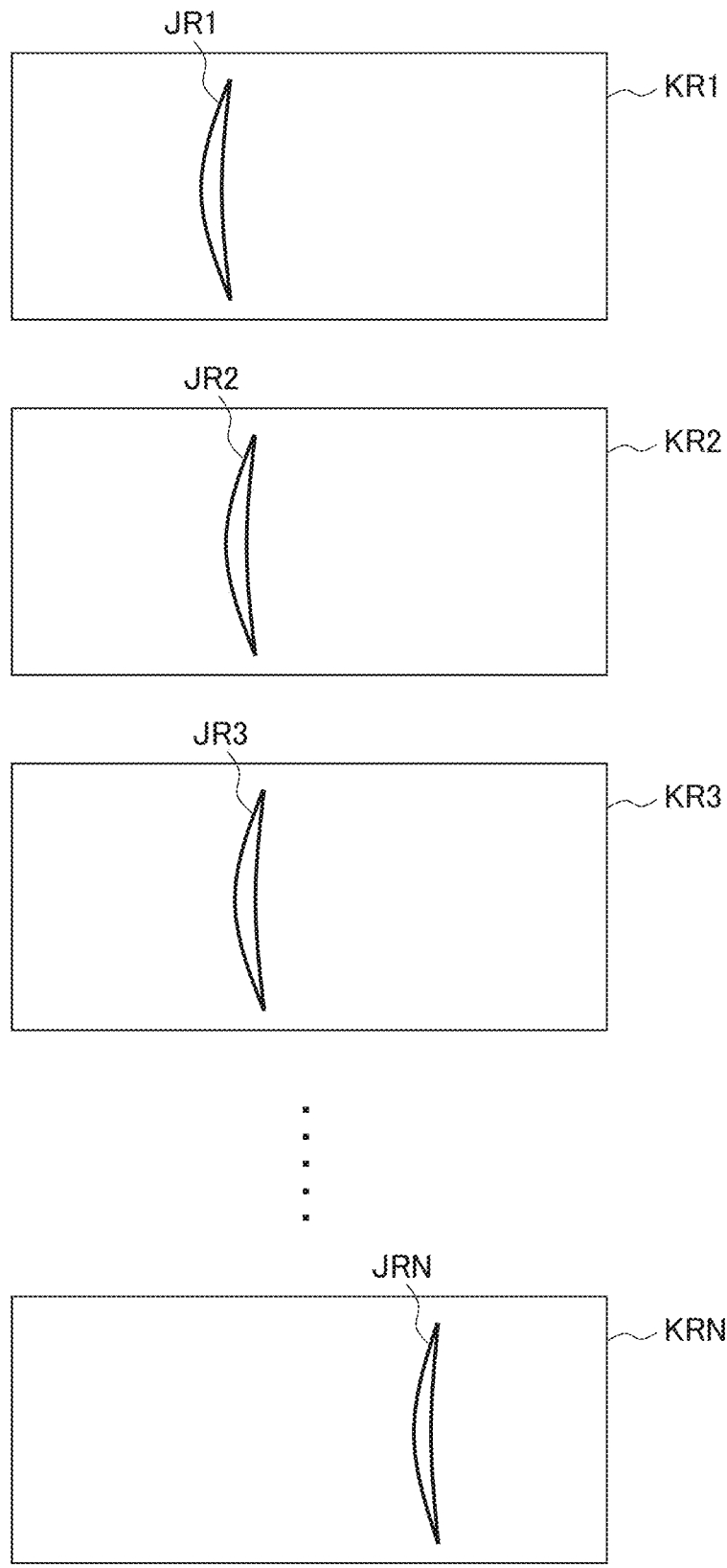
FIG. 21B is a schematic diagram for describing the usage mode of the slit lamp microscope according to the embodiment example.

Subsequently, the image region extracting processor 89 of the seventh embodiment example (FIG. 13) extracts the slit light projected region JLn from the anterior segment image HLn and extracts the slit light projected region JRn from the anterior segment image HRn. FIG. 21A shows the plurality of slit light projected region images KL1 to KLN constructed respectively from the plurality of anterior segment images HL1 to HLN. Similarly, FIG. 21B shows the plurality of slit light projected region images KR1 to KRN constructed respectively from the plurality of anterior segment images HR1 to HRN.

Figure 22:
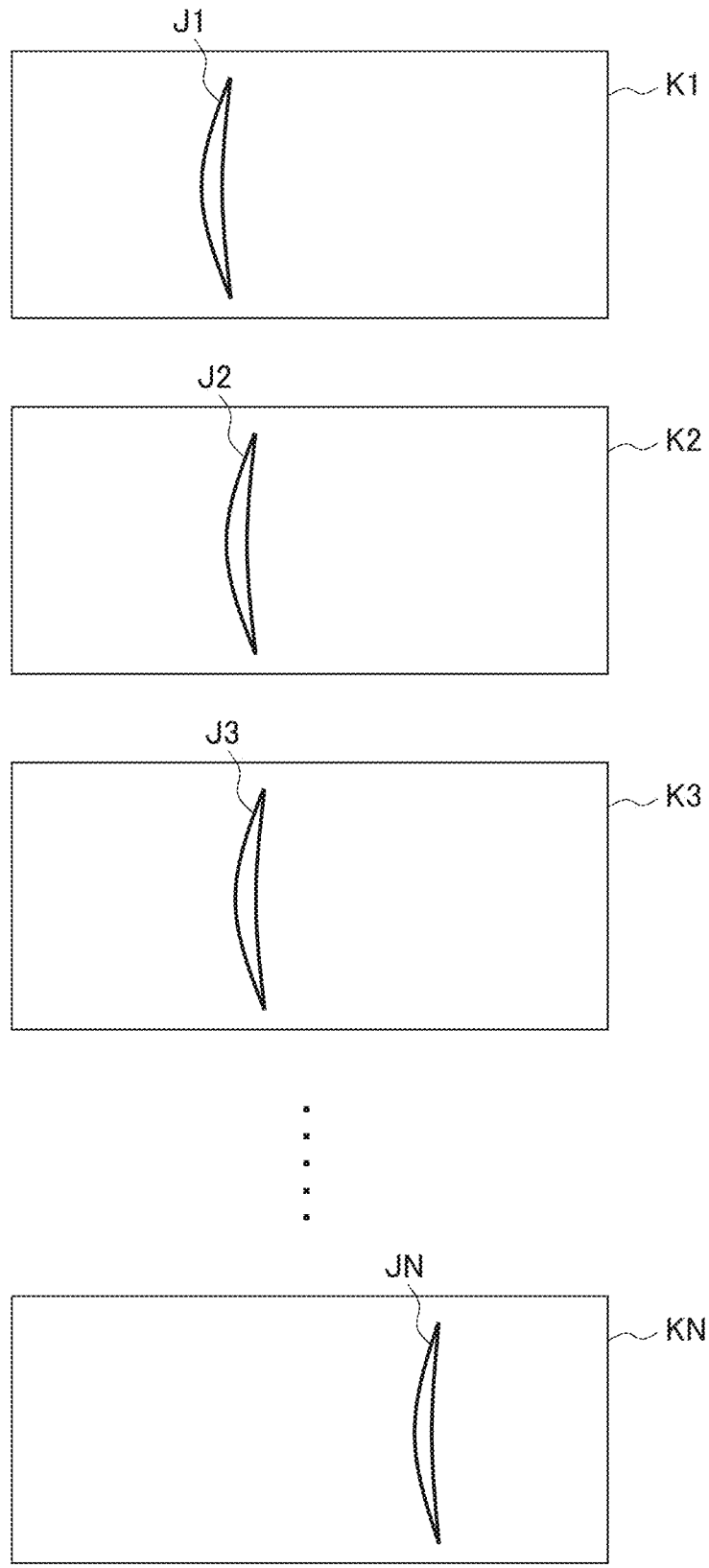
FIG. 22 is a schematic diagram for describing the usage mode of the slit lamp microscope according to the embodiment example.

Next, by applying the process according to the third embodiment example or the fourth embodiment example to the slit light projected region image KLn and the slit light projected region image KRn, a plurality of slit light projected region images containing no artifacts may be obtained. Each of the plurality of slit light projected region images K1 to KN illustrated in FIG. 22 does not suffer from an artifact. The slit light projected region images K1 to KN include the slit light projected regions J1 to JN, respectively.

Figure 23:
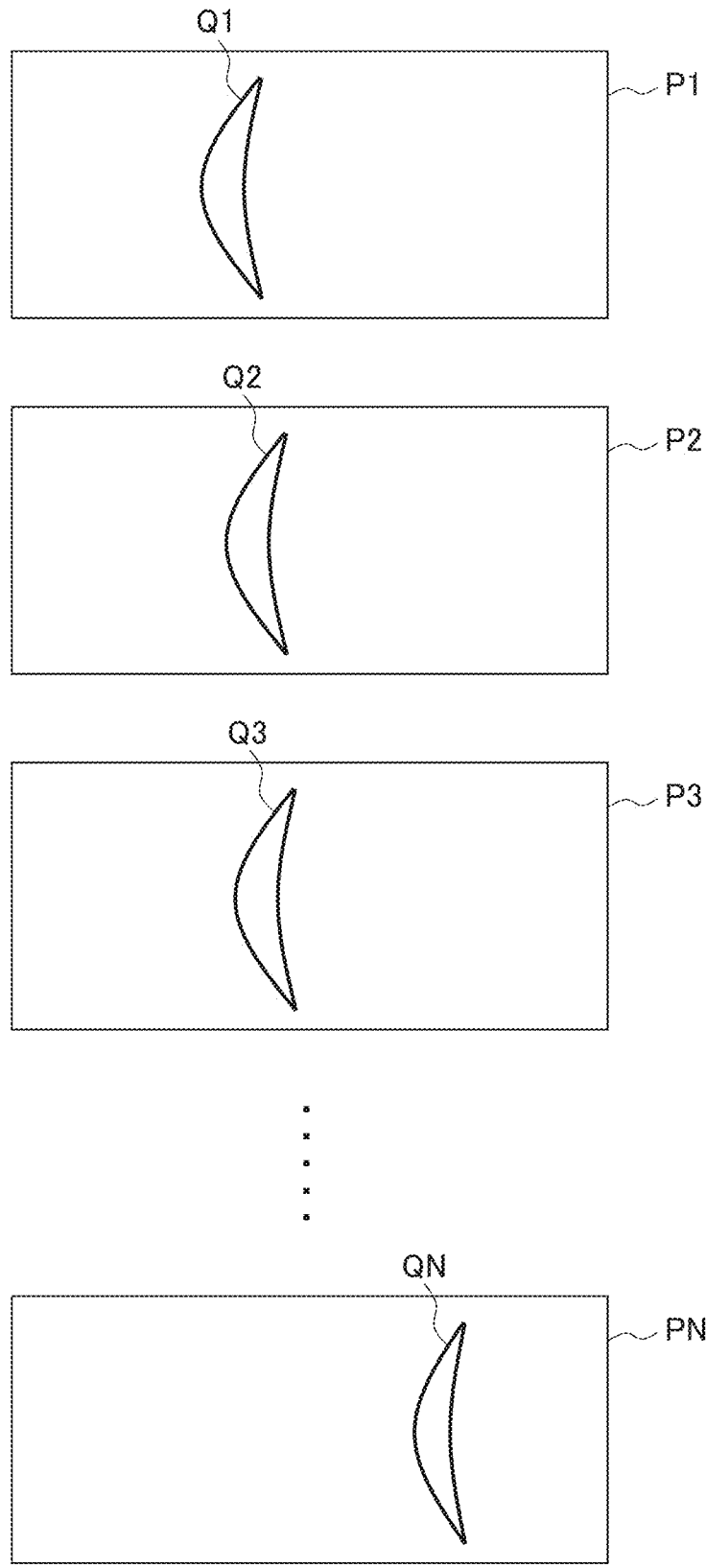
FIG. 23 is a schematic diagram for describing the usage mode of the slit lamp microscope according to the embodiment example.

Subsequently, the distortion correction (keystone correction) described in the ninth embodiment example is applied to each of the slit light projected region images K1 to KN. As a result, a plurality of slit light projected region images, each of which does not contain an artifact and each of whose distortion has been corrected, can be obtained. The plurality of slit light projected region images P1 to PN illustrated in FIG. 23 do not contain any artifacts. Further, the slit light projected region images P1 to PN contain the slit light projected regions Q1 to QN, respectively.

Next, the image position determining processor 87 of the sixth embodiment example determines the relative positions of the plurality of slit light projected region images P1 to PN, based on the anterior segment image H0 shown in FIG. 18. For example, the image position determining processor 87 arranges (determines relative arrangement between) the slit light projected region images P1 to PN, on the basis of the image region corresponding to the anterior corneal surface depicted in the anterior segment image H0, that is, on the basis of the curve having the smaller curvature radius of the two curves depicted in the slit light projected region J0. With this, the slit light projected region images P1 to PN are arranged based on (with a reference of) the curve corresponding to the anterior corneal surface.

The three dimensional image constructing processor 86 of the sixth embodiment example constructs a three dimensional image based on the plurality of slit light projected region images P1 to PN that has been arranged with a reference of the curve of the anterior corneal surface. The three dimensional image constructed does not contain any artifact and has its distortion corrected.

Subsequently, the data processor 8 corrects the aspect ratio of the dimensional image based on the length of the slit light projected onto the anterior segment during the anterior segment scan (the size in the Y direction) and the distance of the movement of the slit light performed by the movement mechanism 6 (the size in the X direction). With such aspect ratio correction, the ratio of the size in the X direction and the size in the Y direction of the three dimensional image is corrected.

Next, the measuring processor 94 of the tenth embodiment example analyzes the three dimensional image to obtain a predetermined measurement value (a value of a predetermined measurement parameter). Examples of the measurement parameter include the followings: anterior corneal surface curvature; anterior corneal surface curvature radius; posterior corneal surface curvature; posterior corneal surface curvature radius; corneal diameter; corneal thickness; corneal topography; anterior chamber depth; corner angle; anterior crystalline lens surface curvature; anterior crystalline lens surface curvature radius; posterior crystalline lens surface curvature; posterior crystalline lens surface curvature radius; and crystalline lens thickness.

Figure 24:
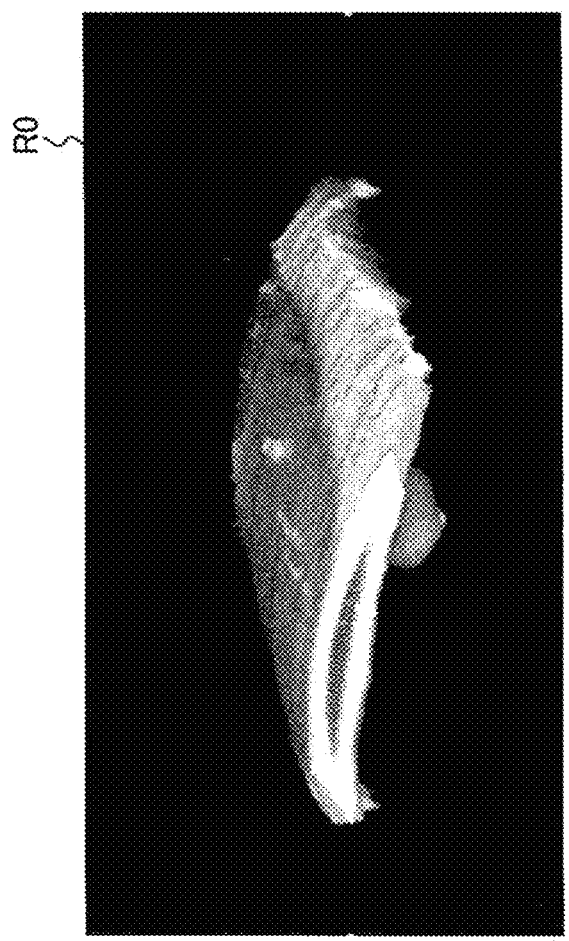
FIG. 24 is an image for describing the usage mode of the slit lamp microscope according to the embodiment example.

FIG. 24 shows the display image R0 acquired by applying volume rendering to an actually acquired three dimensional image. The rendering is performed by the rendering processor 92 of the eighth embodiment example. The controller 7 displays the display image R0 on a display device (not shown in the drawings). The display image R0 depicts a site defined by the anterior corneal surface and the posterior crystalline lens surface.

Figure 25:
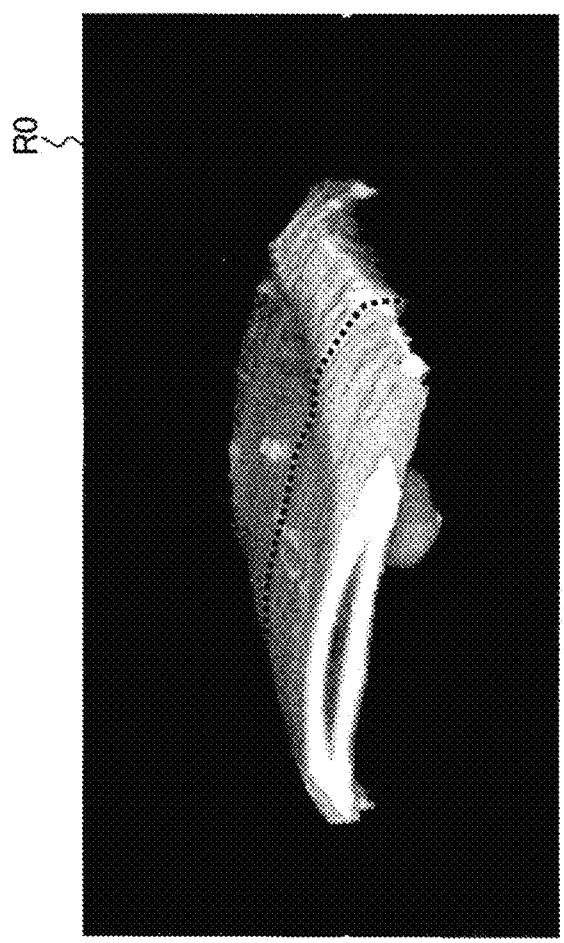
FIG. 25 is an image for describing the usage mode of the slit lamp microscope according to the embodiment example.

The user may observe the display image R0 displayed on the display device and designate a desired cross section using an operation device (not shown in the drawings). The dotted line shown in FIG. 25 indicates the position of the cross section of the display image R0 designated by the user.

Figure 26:
FIG. 26 is an image for describing the usage mode of the slit lamp microscope according to the embodiment example.

The rendering processor 92 may construct a three dimensional partial image by cutting the three dimensional image at the cross section designated by the user. The image R1 shown in FIG. 26 is a display image obtained by applying rendering to the three dimensional partial image obtained by cutting the three dimensional image at the cross section shown in FIG. 25. This display image is also referred to as the three dimensional partial image R1. The three dimensional partial image R1 is an image representing a three dimensional region of the anterior segment, a part of whose outer surface corresponds to the cross section shown in FIG. 25.

Figure 27:
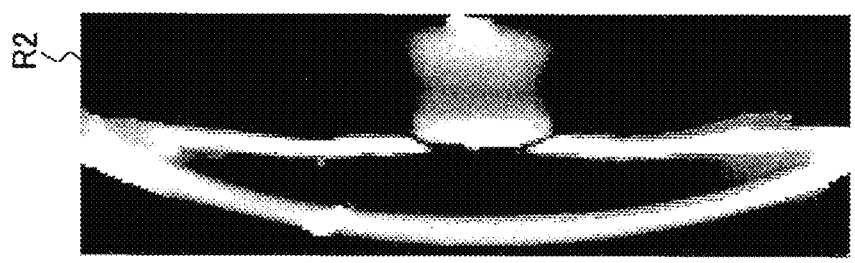
FIG. 27 is an image for describing the usage mode of the slit lamp microscope according to the embodiment example.

In addition, the rendering processor 92 may construct a two dimensional cross sectional image representing the cross section designated by the user. The image R2 shown in FIG. 27 is a two dimensional cross sectional image obtained by cutting the three dimensional image at the cross section shown in FIG. 25.

Figure 28:
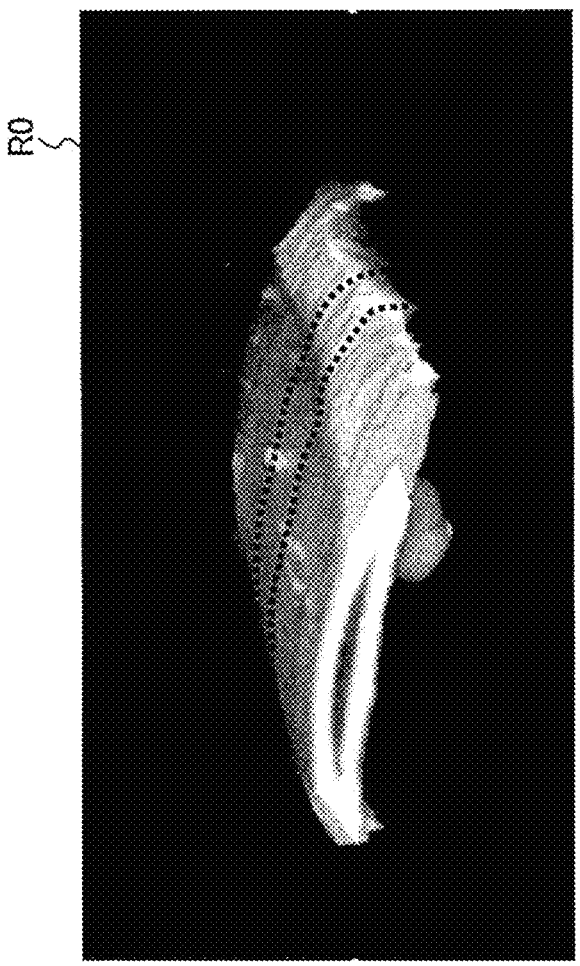
FIG. 28 is an image for describing the usage mode of the slit lamp microscope according to the embodiment example.

The user may observe the display image R0 displayed on the display device and designate a desired slice using an operation device (not shown in the drawings). The two dotted lines shown in FIG. 28 indicate the positions of the two cross sections that define the slice of the display image R0 designated by the user. In other words, the region sandwiched between these two cross sections is the slice designated by the user for the display image R0.

Figure 29:
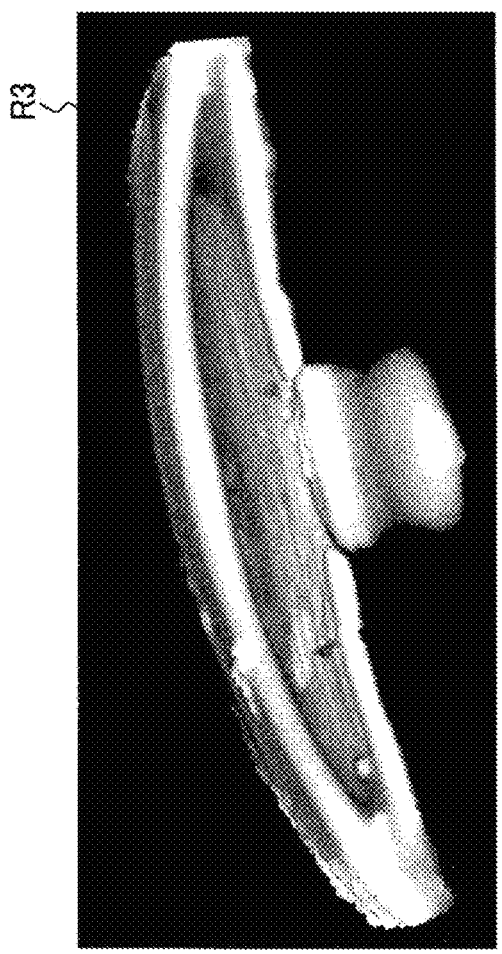
FIG. 29 is an image for describing the usage mode of the slit lamp microscope according to the embodiment example.

The rendering processor 92 may construct a three dimensional slice image corresponding to the slice designated by the user. The image R3 shown in FIG. 29 is a display image obtained by applying rendering to the three dimensional slice image constructed by cutting the three dimensional image at the cross section shown in FIG. 28. This display image is also referred to as the three dimensional slice image R3. The three dimensional slice image R3 is an image representing a three dimensional region of an anterior segment, parts of whose outer surface corresponds to the two cross sections shown in FIG. 28.

The user may grasp the state of the anterior segment by applying rendering to a three dimensional image to observe the outer surface and a desired cross section of the anterior segment, and by performing any of the measurements described in the tenth embodiment example. Then, the user may create an interpretation report.

Twelfth Embodiment Example

In the present embodiment example, an ophthalmic system including an ophthalmic imaging apparatus and an information processing apparatus will be described. The ophthalmic imaging apparatus has at least the function as a slit lamp microscope. The slit lamp microscope included in the ophthalmic imaging apparatus may be any of the first to eleventh embodiment examples. Below, the elements, the configurations, and the reference characters described in the first to eleventh embodiment examples will be referred to accordingly.

Figure 30:
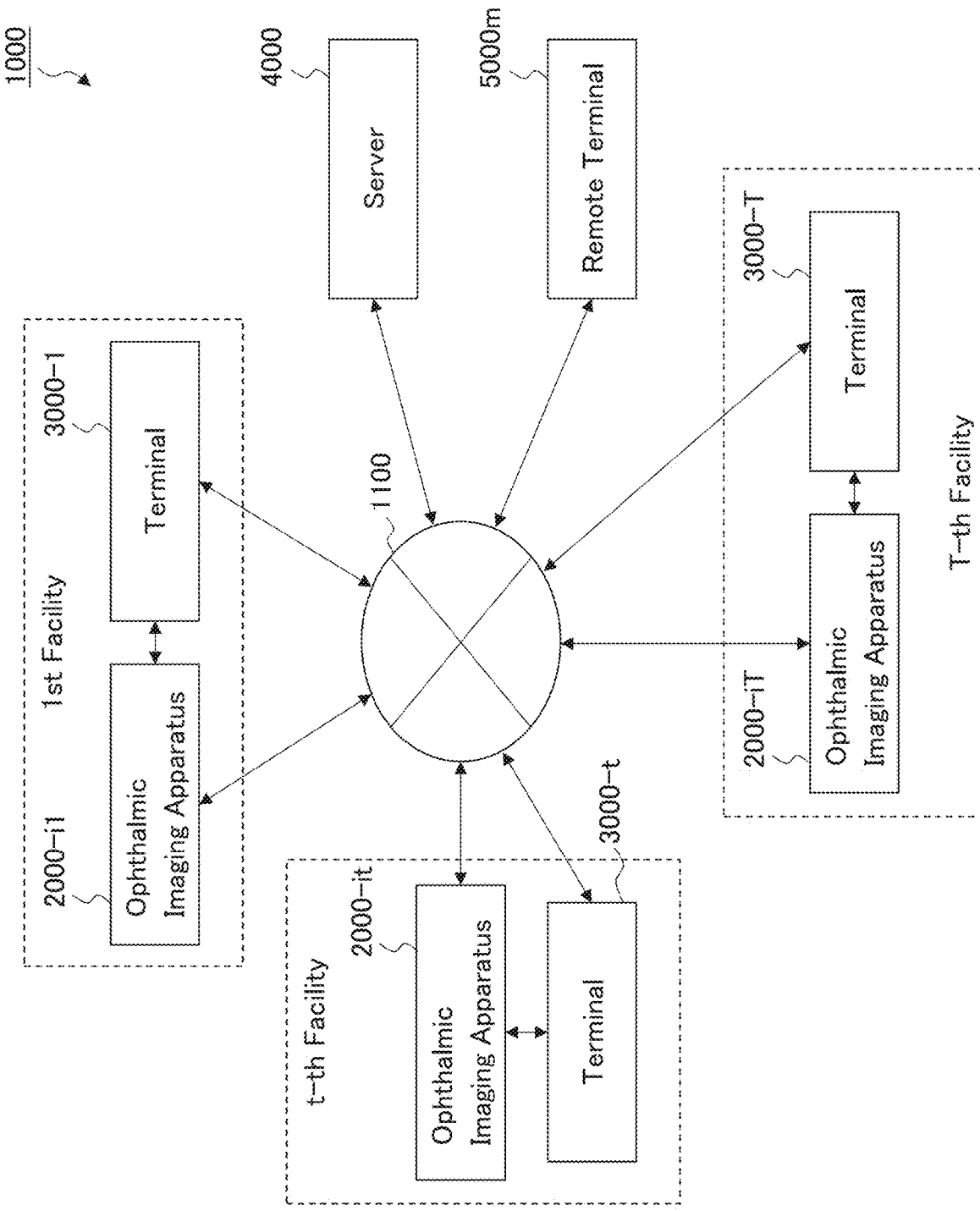
FIG. 30 is a schematic diagram illustrating the configuration of the ophthalmic system according to the embodiment example.

The ophthalmic system 1000 illustrated in FIG. 30 is configured using a communication channel 1100 that is used for establishing connections between the number T of facilities (first facility to T-th facility) where ophthalmic imaging is conducted, the server 4000, and the remote terminal 5000$m$.

Here, the ophthalmologic imaging includes at least anterior segment photography using a slit lamp microscope. The anterior segment photography includes at least the anterior segment scan using the slit light described in any of the first to eleventh embodiment examples.

Each of the facilities (t-th facility: where t=1 to T, T is any positive integer) is provided with the ophthalmic imaging apparatus 2000-$i_t$ (where $i_t$=1 to $K_t$, $K_t$ is any positive integer). In other words, one or more ophthalmic imaging apparatuses 2000-$i_t$ are installed in each of the facilities (t-th facility). The ophthalmic imaging apparatus 2000-$i_t$ constitutes a part of the ophthalmic system 1000. Incidentally, the ophthalmic system 1000 may include an examination apparatus that is capable of performing examination other than ophthalmic examination.

The ophthalmic imaging apparatus 2000-$i_t$ of the present example has the function of an "imaging apparatus" that performs imaging of eyes, and the function of a "computer" that performs various kinds of data processing and communicates with external devices. For another example, an imaging apparatus and a computer may be provided separately from each other. If this is the case, the imaging apparatus and the computer may communicate with each other. There may be any number of imaging apparatuses and any number of computers. For example, a single computer and a plurality of imaging apparatuses can be provided.

The "imaging apparatus" in the ophthalmic imaging apparatus 2000-$i_t$ includes at least a slit lamp microscope. The slit lamp microscope may be any of the slit lamp microscopes according to the first to eleventh embodiment examples, and may include at least the configuration of the first embodiment example (FIG. 1) or the configuration of the second embodiment example (FIG. 5).

Each of the facilities (t-th facility) is provided with an information processing apparatus that can be used by an assistant or a subject (i.e., the terminal 3000-$t$). The terminal 3000-$t$ is a computer for use in the corresponding facility. The terminal 3000-$t$ may be, for example, a mobile terminal such as a tablet terminal or a smartphone, or a server installed in the corresponding facility. The terminal 3000-$t$ may also include a wearable device such as a wireless earphone. Note that the terminal 3000-$t$ is only required to be a computer capable of realizing its functions in the corresponding facility. The terminal 3000-$t$ may be, for example, a computer placed outside the corresponding facility such as a cloud server.

The ophthalmic imaging apparatus 2000-$i_t$ and the terminal 3000-$t$ may communicate with each other through a network such as a network built in the t-th facility (e.g., in-house LAN), a wide area network (e.g., the Internet), or near-field communication technology.

The ophthalmic imaging apparatus 2000-$i_t$ may have the function as a communication device such as a server. If this is the case, the ophthalmic imaging apparatus 2000-$i_t$ and the terminal 3000-$t$ may communicate directly with each other. This makes it possible for the server 4000 and the terminal 3000-$t$ to communicate with each other via the ophthalmic imaging apparatus 2000-$i_t$. Therefore, the function of performing communication between the terminal 3000-$t$ and the server 4000 becomes omissible.

The server 4000 is typically installed in a facility different from any of the first to t-th facilities, for example, in a management center. The server 4000 can communicate with the remote terminal 5000$m$ (where m=1 to M, M is any positive integer) via a network. The network is, for example, a LAN or a wide area network. Further, the server 4000 can communicate with at least one of the ophthalmic imaging apparatuses 2000-$i_t$ installed in the first to t-th facilities via a wide area network.

The server 4000 has the following functions, for example: the function of relaying communication between the ophthalmic imaging apparatus 2000-$i_t$ and the remote terminal 5000m; the function of recording the contents of the communication; the function of storing data and information acquired by the ophthalmic imaging apparatus 2000-$i_t$; and the function of storing data and information acquired by the remote terminal 5000m. In addition, the server 4000 may have a data processing function.

The remote terminal 5000m includes a computer that can be used for interpretation of images of a subject's eye (e.g., a plurality of anterior segment images or a rendered image of a three dimensional image constructed based on the anterior segment images) acquired by the ophthalmic imaging apparatus 2000-$i_t$, and used for creation of a report. The remote terminal 5000m may have a function of data processing.

Figure 31:
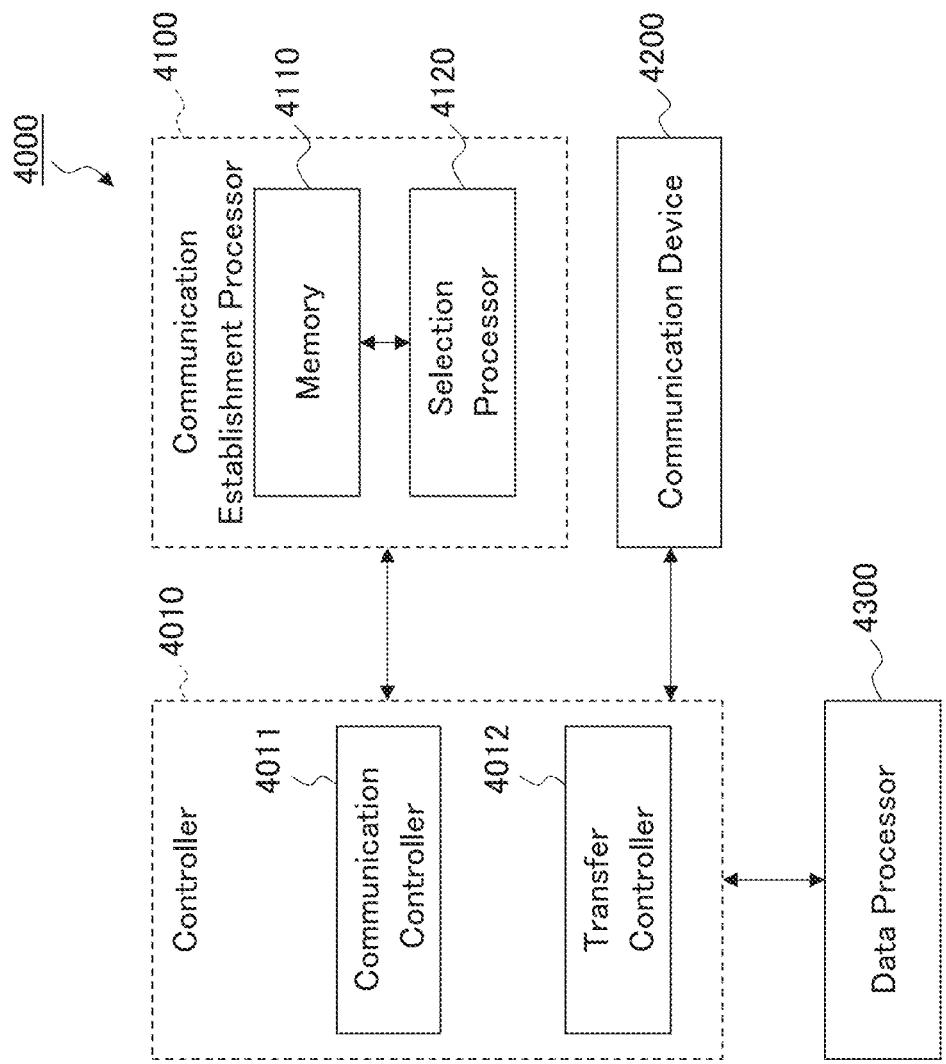
FIG. 31 is a schematic diagram illustrating the configuration of the ophthalmic system according to the embodiment example.

A description is given of the server 4000. The server 4000 illustrated in FIG. 31 includes the controller 4010, the communication establishment processor 4100, and the communication device 4200.

The controller 4010 executes control of each part of the server 4000. The controller 4010 may be capable of executing other processing such as arithmetic processing. The controller 4010 includes a processor. The controller 4010 may further include a RAM, a ROM, a hard disk drive, a solid state drive, etc.

The controller 4010 includes the communication controller 4011 and the transfer controller 4012.

The communication controller 4011 performs control relating to the establishment of communication between a plurality of apparatuses that includes a plurality of ophthalmic imaging apparatuses 2000-$i_t$, a plurality of terminals 3000-$t$, and a plurality of remote terminals 5000m.

For example, the communication controller 4011 sends a control signal for establishing communication to each of two or more apparatuses selected by the selection processor 4120 from among a plurality of apparatuses included in the ophthalmic system 1000. The selection processor 4120 will be described later.

The transfer controller 4012 performs control relating to the exchange of information between two or more apparatuses whose communication has been established by the communication establishment processor 4100 (and the communication controller 4011). For example, the transfer controller 4012 functions to transfer information transmitted from one of the at least two apparatuses whose communication has been established by the communication establishment processor 4100 (and the communication controller 4011), to another apparatus.

As a specific example, in the case where the communication between the ophthalmic imaging apparatus 2000-$i_t$ and the remote terminal 5000m has been established, the transfer controller 4012 can transfer information transmitted from the ophthalmic imaging apparatus 2000-$i_t$ to the remote terminal 5000m. The information transmitted from the ophthalmic imaging apparatus 2000-$i_t$ may include a plurality of anterior segment images acquired by an anterior segment scan using slit light, or a three dimensional image constructed based on these anterior segment images. Conversely, the transfer controller 4012 can transfer information transmitted from the remote terminal 5000m to the ophthalmic imaging apparatus 2000-$i_t$. The information transmitted from the remote terminal 5000m may include an instruction to the ophthalmic imaging apparatus 2000-$i_t$, an interpretation report, and the like.

The transfer controller 4012 may have a function of processing information received from another apparatus. If this is the case, the transfer controller 4012 can transmit at least one of the received information and information created using the processing function, to an apparatus that is a destination of transfer.

For example, the transfer controller 4012 can extract part of the information transmitted from an apparatus such as the ophthalmic imaging apparatus 2000-$i_t$, and transmit the extracted information to an apparatus such as the remote terminal 5000m. Further, the server 4000 or another apparatus may be configured to analyze information transmitted from an apparatus such as the ophthalmic imaging apparatus 2000-$i_t$. The information to be analyzed is, for example, an anterior segment image(s) or a three dimensional image. The transfer controller 4012 can send the result of the analysis of the information (and the original information) to an apparatus such as the remote terminal 5000m.

In the case where a plurality of anterior segment images has been transmitted from the ophthalmic imaging apparatus 2000-$i_t$, the server 4000 or another apparatus can construct a three dimensional image (e.g., stack data or volume data) from the plurality of anterior segment images, and the transfer controller 4012 can send the constructed three dimensional image to the remote terminal 5000m.

In the case where stack data has been transmitted from the ophthalmic imaging apparatus 2000-$i_t$, the server 4000 or another apparatus can construct volume data from the stack data, and the transfer controller 4012 can send the constructed volume data to the remote terminal 5000m.

The data processing executable by the server 4000 or another apparatus is not limited to the examples described above and may include data processing of any kind. For example, the server 4000 or another apparatus may be capable of performing any of the processes described in the first to eleventh embodiment examples, such as rendering of a three dimensional image, artifact elimination, distortion correction, and measurement.

The communication establishment processor 4100 performs processing to establish communication between at least two apparatuses selected from among a plurality of apparatuses including a plurality of ophthalmic imaging apparatuses 2000-$i_t$, a plurality of terminals 3000-$t$ and a plurality of remote terminals 5000m. In the present embodiment example, "establishing communication" refers to a concept which includes, for example, at least one of the followings: (1) establishing unidirectional communication from a state in which communication is disconnected; (2) establishing bidirectional communication from a state in which communication is disconnected; (3) switching from a state in which only data reception is possible to a state in which both data reception and data transmission are possible; and (4) switching from a state in which only data transmission is possible to a state in which both data transmission and data reception are possible.

In addition, the communication establishment processor 4100 can perform processing of disconnecting the established communication. In the present embodiment example, "disconnecting communication" refers to a concept which includes, for example, at least one of the followings: (1) disconnecting communication from a state in which unidirectional communication has been established; (2) disconnecting communication from a state in which bidirectional communication has been established; (3) switching from a state in which bidirectional communication has been established to unidirectional communication; (4) switching from a state in which data transmission and data reception are possible to a state in which only data reception is possible; and (5) switching from a state in which data transmission and data reception are possible to a state in which only data transmission is possible.

Each of the ophthalmic imaging apparatus $2000\text{-}i_t$, the terminal $3000\text{-}t$, and the remote terminal $5000m$ can send at least one of the following communication requests to the server 4000: a communication request (a call request) for calling another apparatus or the user thereof; and a communication request (an interruption request) for interrupting communication between two other apparatuses. A call request is issued manually or automatically, and an interruption request is issued manually or automatically. The server 4000 (the communication device 4200 therein) receives a communication request transmitted from the ophthalmic imaging apparatus $2000\text{-}i_t$, the terminal $3000\text{-}t$, or the remote terminal $5000m$.

The communication establishment processor 4100 of the present embodiment example may include the selection processor 4120. For example, based on a communication request sent from the ophthalmic imaging apparatus $2000\text{-}i_t$, the terminal $3000\text{-}t$, or the remote terminal $5000m$, the selection device 4120 selects one or more apparatuses other than the apparatus that has sent the communication request, from among the ophthalmic imaging apparatus $2000\text{-}i_t$, the terminal $3000\text{-}t$, and the remote terminal $5000m$.

A specific example of the processing executed by the selection processor 4120 will be described. When a communication request sent from the ophthalmic imaging apparatus $2000\text{-}i_t$ or the terminal $3000\text{-}t$ is received (e.g., when a request for interpretation of an image acquired by the ophthalmic imaging apparatus $2000\text{-}i_t$ is received), the selection processor 4120 selects, for example, any apparatus from among the plurality of remote terminals $5000m$. The communication establishment processor 4100 establishes communication between the selected remote terminal $5000m$, and at least one of the ophthalmic imaging apparatus $2000\text{-}i_t$ and the terminal $3000\text{-}t$.

The apparatus selection in response to a communication request is performed, for example, based on a preset attribute. Examples of the attribute include types of examination (e.g., types of imaging modalities, types of images, types of diseases, types of possible diseases), degrees of expertise required, levels of skills required, and types of languages. In order to realize the processing according to the present example, the communication establishment processor 4100 may include the memory 4110 in which attribute information prepared in advance is stored. Attributes corresponding to the remote terminals $5000m$ and/or attributes corresponding to the users thereof (doctors, optometrists) are recorded in the attribute information.

The identification of users is carried out using user identifiers (user IDs) respectively assigned to users in advance. Further, the identification of the remote terminals $5000m$ is carried out using, for example, apparatus identifiers or network addresses respectively assigned to apparatuses in advance. In a typical example, the attribute information includes attributes of each user such as the user's specialized field (e.g., the department, the specialized disease), the user's degree of expertise, the user's level of skills, or the types of languages the user is able to use.

When the selection processor 4120 refers to the attribute information, a communication request to be sent from the ophthalmic imaging apparatus $2000\text{-}i_t$, the terminal $3000\text{-}t$, or the remote terminal $5000m$ may include information related to attributes. For example, an interpretation request (i.e., a diagnosis request) to be transmitted from the ophthalmic imaging apparatus $2000\text{-}i_t$ may include any of the followings: (1) information indicating the type of imaging modality; (2) information indicating the type of image; (3) information indicating the name of disease or the name of possible disease; (4) information indicating the degree of difficulty of interpretation; and (5) information indicating a language(s) the user of the ophthalmic imaging apparatus $2000\text{-}i_t$ and/or the terminal $3000\text{-}t$ uses.

When such an interpretation request is received, the selection processor 4120 can select one of the remote terminals $5000m$ based on the interpretation request and the attribute information stored in the memory 4110. In this selection processing, the selection processor 4120 checks the information related to the attributes included in the interpretation request against the information recorded in the attribute information stored in the memory 4110. With this, the selection processor 4120 selects, for example, the remote terminal $5000m$ corresponding to a doctor (or an optometrist) who satisfies any one of the following attributes: (1) a doctor who is specializing in the concerned imaging modality; (2) a doctor who is specializing in the concerned type of images; (3) a doctor who is specializing in the concerned disease (or the concerned possible disease); (4) a doctor who is capable of performing interpretation of the concerned level of difficulty; and (5) a doctor who is capable of using the concerned language.

The correspondence between doctors or optometrists and the remote terminals $5000m$ is made by, for example, referring to user IDs input, at the time of logging in, to the remote terminals $5000m$ (or to the ophthalmic system 1000).

The communication device 4200 performs data communication with another apparatus. This another apparatus is, for example, any of the ophthalmic imaging apparatus $2000\text{-}i_t$, the terminal $3000\text{-}t$, and the remote terminal $5000m$. The system of the data communication and encryption may be performed in the same manner as in the communication device provided in the ophthalmic imaging apparatus $2000\text{-}i_t$ (the communication device 9 of the first embodiment example).

The server 4000 includes the data processor 4300. The data processor 4300 executes various kinds of data processes. The data processor 4300 may be configured to process a plurality of anterior segment images or a three dimensional image acquired by the ophthalmic imaging apparatus $2000\text{-}i_t$ (in particular, a slit lamp microscope). The data processor 4300 includes a processor, a primary storage, a secondary storage, and the like. The secondary storage stores a data processing program or the like. The function of the data processor 4300 is realized by cooperation of software such as the data processing program and hardware such as the processor.

The data processor 4300 may include any one or more of the followings: the data processor 8; the data processor 8A (the image selecting processor 81, the three dimensional image constructing processor 82); the data processor 8B (the artifact eliminating processor 83, the three dimensional image constructing processor 84); the data processor 8C (the three dimensional image constructing processor 85); the data processor 8D (the three dimensional image constructing processor 86, the image position determining processor 87); the three dimensional image constructing processor 88 (the image region extracting processor 89, the image composing processor 90); the data processor 8E (the three dimensional image constructing processor 91, the rendering processor 92); the data processor 8F (the distortion correcting processor 93); and the data processor 8G (the measuring processor 94).

The server 4000 may provide data obtained by the data processor 4300 to another apparatus. For example, in the case where the data processor 4300 constructs a three dimensional image from a plurality of anterior segment images acquired by the ophthalmic imaging apparatus 2000-$i_t$, the server 4000 can transmit the constructed three dimensional image to the remote terminal 5000*m* by using the communication device 4200. In the case where the data processor 4300 applies the rendering to a three dimensional image constructed by the ophthalmic imaging apparatus 2000-$i_t$ or the data processor 4300, the server 4000 can transmit the constructed rendered image to the remote terminal 5000*m* by using the communication device 4200. In the case where the data processor 4300 applies a measuring process to one or more anterior segment images or a three dimensional image, the server 4000 can transmit the obtained measurement data to the remote terminal 5000*m* by using the communication device 4200. In the case where the data processor 4300 applies the distortion correction to one or more anterior segment images or a three dimensional image, the server 4000 can transmit the corrected image to the remote terminal 5000*m* by using the communication device 4200.

Figure 32:
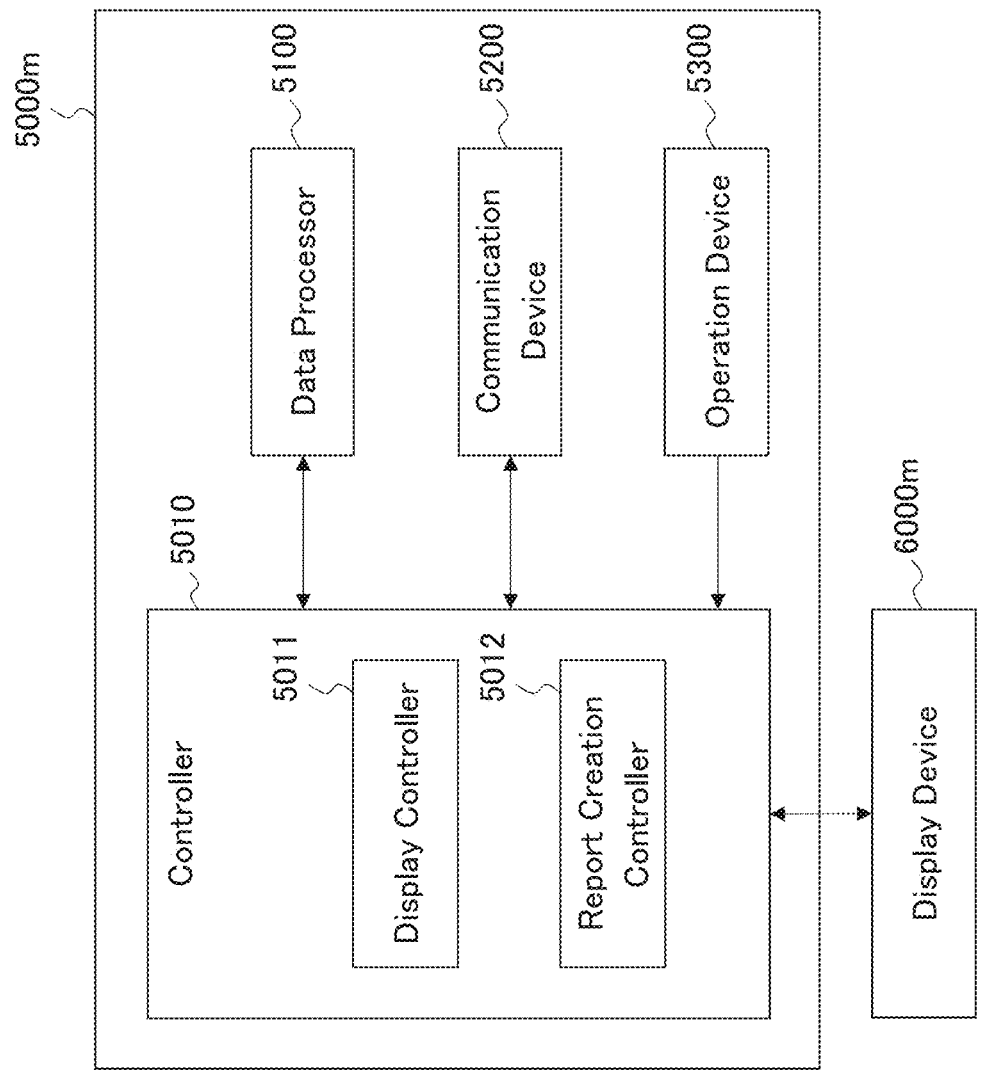
FIG. 32 is a schematic diagram illustrating the configuration of the ophthalmic system according to the embodiment example.

Next, a description is given of the remote terminal 5000*m*. The remote terminal 5000*m* illustrated in FIG. 32 includes the controller 5010, the data processor 5100, the communication device 5200, and the operation device 5300.

The controller 5010 executes control of each part of the remote terminal 5000*m*. The controller 5010 may be capable of executing other processing such as arithmetic processing. The controller 5010 includes a processor, a RAM, a ROM, a hard disk drive, a solid state drive, etc.

The controller 5010 includes the display controller 5011. The display controller 5011 controls the display device 6000*m*. The display device 6000*m* may be included in the remote terminal 5000*m* or may be a peripheral device connected to the remote terminal 5000*m*. The display controller 5011 controls the display device 6000*m* to display an image of the anterior segment of the subject's eye E. Examples of the image of the anterior segment include a slit photographed image, a Scheimpflug photographed image, a rendered image of a three dimensional image, a front image, an image acquired by another modality (e.g., an OCT image), an image representing a measurement result, and an image representing an analysis result.

The controller 5010 includes the report creation controller 5012. The report creation controller 5012 executes various kinds of controls for creating a report regarding the information displayed by the display controller 5011. For example, the report creation controller 5012 controls the display device 6000*m* to display a screen and a graphical user interface (GUI) used for report creation. Further, the report creation controller 5012 inputs or records, into or on a predetermined report template, information input by the user, an image of the anterior segment, measurement data, analysis data, and the like.

<Data Processor 5100>

The data processor 5100 executes various kinds of data processing. The data processor 5100 may be configured to process a plurality of anterior segment images or a three dimensional image acquired by the ophthalmic imaging apparatus 2000-$i_t$ (in particular, a slit lamp microscope). Further, the data processor 5100 may be configured to process a three dimensional image or a rendered image constructed by another information processing apparatus such as the server 4000. The data processor 5100 includes a processor, a primary storage, a secondary storage, and the like. A data processing program or the like is stored in the secondary storage. The function of the data processor 5100 is realized by cooperation of software such as the data processing program and hardware such as the processor.

The data processor 5100 may include any one or more of the followings: the data processor 8; the data processor 8A (the image selecting processor 81, the three dimensional image constructing processor 82); the data processor 8B (the artifact eliminating processor 83, the three dimensional image constructing processor 84); the data processor 8C (the three dimensional image constructing processor 85); the data processor 8D (the three dimensional image constructing processor 86, the image position determining processor 87); the three dimensional image constructing processor 88 (the image region extracting processor 89, the image composing processor 90); the data processor 8E (the three dimensional image constructing processor 91, the rendering processor 92); the data processor 8F (the distortion correcting processor 93); and the data processor 8G (the measuring processor 94).

The communication device 5200 performs data communication with another apparatus. This another apparatus is, for example, any of the ophthalmic imaging apparatus 2000-$i_t$, the terminal 3000-$t$, and the server 4000. The system of the data communication and encryption may be performed in the same manner as in the communication device of the ophthalmic imaging apparatus 2000-$i_t$.

The operation device 5300 is used to operate the remote terminal 5000*m* and input information to the remote terminal 5000*m*. In the present embodiment example, the operation device 5300 is used to create a report. The operation device 5300 includes an operation device and an input device. The operation device 5300 includes, for example, a mouse, a keyboard, a trackball, an operation panel, a switch, a button, a dial, or the like. The operation device 5300 may include a touch screen.

Some advantageous technical effects achieved by the present embodiment example will be described.

The ophthalmic system 1000 includes one or more slit lamp microscopes (the ophthalmic imaging apparatus 2000-$i_t$) and one or more information processing apparatuses (at least one of the server 4000 and the remote terminal 5000*m*). The information processing apparatus is connected to the slit lamp microscope via a communication channel and processes an image of the anterior segment of a subject's eye acquired by the slit lamp microscope.

The slit lamp microscope (the ophthalmic imaging apparatus 2000-$i_t$) includes an illumination system, a photography system, and a movement mechanism. The illumination system is configured to project slit light onto the anterior segment of the subject's eye. The photography system includes an optical system and an image sensor. The optical system is configured to direct light coming from the anterior segment onto which the slit light is being projected. The image sensor includes a light detecting plane that receives the light directed by the optical system. The movement mechanism includes a movement mechanism configured to move the illumination system and the photography system. A subject plane along the optical axis of the illumination system, the optical system, and the light detecting plane satisfy the Scheimpflug condition. The photography system acquires a plurality of images of the anterior segment by performing repetitive photography in parallel with the movement of the illumination system and the photography system performed by the movement mechanism.

The illumination system and the photography system of the slit lamp microscope (the ophthalmic imaging apparatus 2000-$i_t$) may be configured in such a manner that at least a region defined by an anterior corneal surface and a posterior crystalline lens surface becomes in focus of the photography system.

The illumination system may be configured to project the slit light whose longitudinal direction corresponds to a body axis direction of a subject, onto the anterior segment. In the case where this configuration is employed, the movement mechanism may be configured to move the illumination system and the photography system in a direction orthogonal to the body axis direction.

The length of the slit light may be set to be equal to or greater than a corneal diameter in the body axis direction. In addition, the distance of the movement of the illumination system and the photography system performed by the movement mechanism may be set to be equal to or greater than a corneal diameter in the direction orthogonal to the body axis direction.

According to the present embodiment example having such a configuration, at least the same advantageous technical effects as those of the first embodiment example can be achieved. In addition, any of the matters and items such as the configuration, elements, functions, actions, and advantageous technical effects described in the first embodiment example, may be applied to (combined with) the present embodiment example.

In the present embodiment example, the photography system of the slit lamp microscope (the ophthalmic imaging apparatus 2000-$i_t$) may include a first photography system and a second photography system. The first photography system includes a first optical system and a first image sensor. The first optical system is configured to direct the light coming from the anterior segment onto which the slit light is being projected and the first image sensor includes a first light detecting plane that receives the light directed by the first optical system. Further, the first photography system acquires a first image group by performing repetitive photography in parallel with the movement of the illumination system and the photography system. The second photography system includes a second optical system and a second image sensor. The second optical system is configured to direct the light coming from the anterior segment onto which the slit light is being projected, and the second image sensor includes a second light detecting plane that receives the light directed by the second optical system. Further, the second photography system acquires a second image group by performing repetitive photography in parallel with the movement of the illumination system and the photography system. Furthermore, an orientation of an optical axis of the first optical system and an orientation of an optical axis of the second optical system are different from each other. In addition, the subject plane, the first optical system, and the first light detecting plane satisfy the Scheimpflug condition, and the subject plane, the second optical system, and the second light detecting plane satisfy the Scheimpflug condition.

The optical system included in the photography system may include a reflector and at least one lens. The reflector is configured and arranged to reflect the light coming from the anterior segment onto which the slit light is being projected and traveling in a direction away from the optical axis of the illumination system, toward a direction approaching the optical axis of the illumination system. The at least one lens is configured and arranged to form an image of the light reflected by the reflector on the light detecting plane.

According to the present embodiment example having such a configuration, at least the same advantageous technical effects as those of the second embodiment example can be achieved. In addition, any of the matters and items such as the configuration, elements, functions, actions, and advantageous technical effects described in the second embodiment example may be applied to (combined with) the present embodiment example.

The optical axis of the first optical system and the optical axis of the second optical system in the present embodiment example may be tilted in mutually opposite directions with respect to the optical axis of the illumination system. Further, the information processing apparatus (the server 4000 and/or the remote terminal 5000$m$) may include an image selecting processor configured to judge whether at least one of two images substantially simultaneously acquired by the first photography system and the second photography system contains an artifact, and select a first image of the two images if a second image of the two images is judged to contain the artifact.

Further, the information processing apparatus (the server 4000 and/or the remote terminal 5000$m$) may include a three dimensional image constructing processor configured to construct a three dimensional image based on an image group including images selected from the first image group and the second image group by the image selecting processor.

According to the present embodiment example having such a configuration, at least the same advantageous technical effects as those of the third embodiment example can be achieved. In addition, any of the matters and items such as the configuration, elements, functions, actions, and advantageous technical effects described in the third embodiment example may be applied to (combined with) the present embodiment example.

The information processing apparatus (the server 4000 and/or the remote terminal 5000$m$) in the present embodiment example may include an artifact eliminating processor configured to judge whether at least one of two images substantially simultaneously acquired by the first photography system and the second photography system contains an artifact by comparing the two images, and eliminate the artifact if the at least one of the two images is judged to contain the artifact.

Further, the information processing apparatus (the server 4000 and/or the remote terminal 5000$m$) may include a three dimensional image constructing processor configured to construct a three dimensional image based on an image group including an image from which the artifact is eliminated by the artifact eliminating processor.

According to the present embodiment example having such a configuration, at least the same advantageous technical effects as those of the fourth embodiment example can be achieved. In addition, any of the matters and items such as the configuration, elements, functions, actions, and advantageous technical effects described in the fourth embodiment example may be applied to (combined with) the present embodiment example.

In the present embodiment example, the information processing apparatus (the server 4000 and/or the remote terminal 5000$m$) may include a three dimensional image constructing processor configured to construct a three dimensional image based on a plurality of images acquired by the slit lamp microscope (the ophthalmic imaging apparatus 2000-$i_t$).

According to the present embodiment example having such a configuration, at least the same advantageous technical effects as those of the fifth embodiment example can be achieved. In addition, any of the matters and items such as the configuration, elements, functions, actions, and advantageous technical effects described in the fifth embodiment example may be applied to (combined with) the present embodiment example.

In the present embodiment example, the movement mechanism may include the movement mechanism includes a rotation mechanism configured to integrally rotate the illumination system and the photography system about the optical axis of the illumination system. Further, the photography system can acquire the plurality of images in a state where the illumination system and the photography system are arranged in a first rotation position, and the photography system acquires an image of the anterior segment onto which the slit light is being projected by the illumination system in a state where the illumination system and the photography system are arranged in a second rotation position different from the first rotation position. In addition, the three dimensional image constructing processor may include an image position determining processor configured to determine relative positions of the plurality of images based on the image acquired in the second rotation position.

According to the present embodiment example having such a configuration, at least the same advantageous technical effects as those of the sixth embodiment example can be achieved. In addition, any of the matters and items such as the configuration, elements, functions, actions, and advantageous technical effects described in the sixth embodiment example may be applied to (combined with) the present embodiment example.

The three dimensional image constructing processor in the present embodiment example may include an image region extracting processor and an image composing processor. The image region extracting processor is configured to extract image regions corresponding to the regions onto which the slit light is being projected, from each of the plurality of images acquired by the slit lamp microscope (the ophthalmic imaging apparatus $2000\text{-}i_t$). The image composing processor is configured to construct a three dimensional image by composing a plurality of image regions extracted from each of the plurality of images by the image region extracting processor.

The image region extracting processor may be configured in such a manner that an image region corresponding to both the region onto which the slit light is being projected and a predetermined site of the anterior segment is extracted, from each of the plurality of images acquired by the slit lamp microscope (the ophthalmic imaging apparatus $2000\text{-}i_t$).

The predetermined site may be a site defined by the anterior corneal surface and the posterior crystalline lens surface.

According to the present embodiment example having such a configuration, at least the same advantageous technical effects as those of the seventh embodiment example can be achieved. In addition, any of the matters and items such as the configuration, elements, functions, actions, and advantageous technical effects described in the seventh embodiment example may be applied to (combined with) the present embodiment example.

The information processing apparatus (the server 4000 and/or the remote terminal 5000$m$) in the present embodiment example may include a rendering processor configured to apply rendering to a three dimensional image to construct a rendered image.

Upon receiving a result of designation of a cross section for a three dimensional image, the rendering processor may cut the three dimensional image at the designated cross section to construct a three dimensional partial image.

Upon receiving a result of designation of a cross section for a three dimensional image, the rendering processor may construct a two dimensional cross sectional image representing the designated cross section.

Upon receiving a result of designation of a slice for a three dimensional image, the rendering processor may construct a three dimensional slice image corresponding to the designated slice.

According to the present embodiment example having such a configuration, at least the same advantageous technical effects as those of the eighth embodiment example can be achieved. In addition, any of the matters and items such as the configuration, elements, functions, actions, and advantageous technical effects described in the eighth embodiment example may be applied to (combined with) the present embodiment example.

The information processing apparatus (the server 4000 and/or the remote terminal 5000$m$) in the present embodiment example may include a distortion correcting processor. The distortion correcting processor is configured to apply processing to correct distortion caused by an optical axis angle, which is an angle formed by an optical axis of the illumination system and an optical axis of the photography system, to at least one of a plurality of images acquired by the slit lamp microscope (the ophthalmic imaging apparatus $2000\text{-}i_t$).

The optical axis of the optical system included in the photography system may be tilted, with respect to the optical axis of the illumination system, in the third direction orthogonal to both the first direction along the optical axis of the illumination system and the second direction along the longitudinal direction of the slit light. In the case where such a configuration is employed, the distortion correcting processor can execute a process to correct distortion in a plane including (spanned by) both the first direction and the second direction.

The distortion correcting processor may be configured to store in advance a correction factor determined based on a predetermined reference angle and an optical axis angle, and apply a process for correcting the distortion based on the correction factor.

According to the present embodiment example having such a configuration, at least the same advantageous technical effects as those of the ninth embodiment example can be achieved. In addition, any of the matters and items such as the configuration, elements, functions, actions, and advantageous technical effects described in the ninth embodiment example may be applied to (combined with) the present embodiment example.

The information processing apparatus (the server 4000 and/or the remote terminal 5000$m$) in the present embodiment example may include a first measuring processor. The first measuring processor is configured to obtain a predetermined measurement value (a value of a predetermined measurement parameter) by analyzing at least one of a plurality of images acquired by the slit lamp microscope (the ophthalmic imaging apparatus $2000\text{-}i_t$).

Further, in the present embodiment example, the information processing apparatus (the server 4000 and/or the remote terminal 5000$m$) may include a second measuring processor. The second measuring processor is configured to obtain a predetermined measurement value (a value of a predetermined measurement parameter) by analyzing a three dimensional image constructed by the three dimensional image constructing processor.

According to the present embodiment example having such a configuration, at least the same advantageous technical effects as those of the tenth embodiment example can be achieved. In addition, any of the matters and items such as the configuration, elements, functions, actions, and advantageous technical effects described in the tenth embodiment example may be applied to (combined with) the present embodiment example.

The slit lamp microscope (the ophthalmic imaging apparatus 2000-$i_t$) in the present embodiment example may include a moving image photography system. The moving image photography system is configured to perform moving image photography of an anterior segment from a fixed position in parallel with acquisition of a plurality of images performed by the photography system.

Furthermore, the slit lamp microscope (the ophthalmic imaging apparatus 2000-$i_t$) may include a motion detecting processor. The motion detecting processor is configured to detect the motion of the subject's eye by analyzing a moving image acquired by the moving image photography system.

In addition, the slit lamp microscope (the ophthalmic imaging apparatus 2000-$i_t$) may include a movement controller configured to control the movement mechanism based on an output from the motion detecting processor.

According to the present embodiment example having such a configuration, at least the same advantageous technical effects as those of the eleventh embodiment example can be achieved. In addition, any of the matters and items such as the configuration, elements, functions, actions, and advantageous technical effects described in the eleventh embodiment example may be applied to (combined with) the present embodiment example.

SOME ADDITIONAL MATTERS AND ITEMS

The embodiment examples described above are merely typical aspect examples of the implementation of the present disclosure. Therefore, any modifications (e.g., omission, substitution, replacement, addition, etc.) may be made within the scope of the present disclosure.

A program that causes a computer to execute one or more processes according to any one of the first to twelfth embodiment examples or according to a combination of any two or more of the first to twelfth embodiment examples may be configured. In addition, a program that causes a computer to execute one or more processes implemented by applying any modification within the scope of the present disclosure to any one of the first to twelfth embodiment examples or to a combination of any two or more of the first to twelfth embodiment examples may be configured.

Furthermore, a computer-readable non-transitory recording medium that stores such a program can be created. The non-transitory recording medium may be in any form, and examples of the non-transitory recording medium include a magnetic disk, an optical disk, a magneto-optical disk, and a semiconductor memory.

The present disclosure includes a method implemented by any one of the first to twelfth embodiment examples or a combination of any two or more of the first to twelfth embodiment examples. Further, the present disclosure also includes a method implemented by applying any modification within the scope of the present disclosure to any one of the first to twelfth embodiment examples or a combination of any two or more of the first to twelfth embodiment examples.

What is claimed is:

1. A slit lamp microscope comprising:
   an illumination system configured to project slit light onto an anterior segment of an eye;
   a photography system including an optical system and an image sensor, the optical system being configured to direct light coming from the anterior segment onto which the slit light is being projected, and the image sensor including a light detecting plane that receives the light directed by the optical system; and
   a movement mechanism configured to move the illumination system and the photography system, wherein
   a subject plane along an optical axis of the illumination system, the optical system, and the light detecting plane satisfy a Scheimpflug condition,
   the photography system acquires a plurality of images of the anterior segment by performing repetitive photography in parallel with movement of the illumination system and the photography system performed by the movement mechanism,
   the photography system includes a first photography system and a second photography system,
   the first photography system includes a first optical system and a first image sensor, the first optical system being configured to direct the light coming from the anterior segment onto which the slit light is being projected, and the first image sensor including a first light detecting plane that receives the light directed by the first optical system, wherein the first photography system acquires a first image group by performing repetitive photography in parallel with the movement,
   the second photography system includes a second optical system and a second image sensor, the second optical system being configured to direct the light coming from the anterior segment onto which the slit light is being projected, and the second image sensor including a second light detecting plane that receives the light directed by the second optical system, wherein the second photography system acquires a second image group by performing repetitive photography in parallel with the movement,
   an orientation of an optical axis of the first optical system and an orientation of an optical axis of the second optical system are different from each other, and
   the subject plane, the first optical system, and the first light detecting plane satisfy the Scheimpflug condition, and the subject plane, the second optical system, and the second light detecting plane satisfy the Scheimpflug condition.

2. The slit lamp microscope of claim 1, wherein the optical axis of the first optical system and the optical axis of the second optical system are tilted in mutually opposite directions with respect to the optical axis of the illumination system, and
   the slit lamp microscope further comprising an image selecting processor configured to judge whether at least one of two images substantially simultaneously acquired by the first photography system and the second photography system contains an artifact, and select a first image of the two images if a second image of the two images is judged to contain the artifact.

3. The slit lamp microscope of claim 2, further comprising a three dimensional image constructing processor configured to construct a three dimensional image based on an image group including images selected from the first image group and the second image group by the image selecting processor.

4. The slit lamp microscope of claim 3, wherein
the movement mechanism includes a rotation mechanism configured to integrally rotate the illumination system and the photography system about the optical axis of the illumination system,
the photography system acquires the plurality of images when the illumination system and the photography system are arranged in a first rotation position,
the photography system acquires an image of the anterior segment onto which the slit light is being projected by the illumination system when the illumination system and the photography system are arranged in a second rotation position different from the first rotation position, and
the three dimensional image constructing processor includes an image position determining processor configured to determine relative positions of the plurality of images based on the image acquired in the second rotation position.

5. The slit lamp microscope of claim 1, further comprising an artifact eliminating processor configured to judge whether at least one of two images substantially simultaneously acquired by the first photography system and the second photography system contains an artifact by comparing the two images, and eliminate the artifact if the at least one of the two images is judged to contain the artifact.

6. The slit lamp microscope of claim 5, further comprising a three dimensional image constructing processor configured to construct a three dimensional image based on an image group including an image from which the artifact is eliminated by the artifact eliminating processor.

7. The slit lamp microscope of claim 6, wherein
the movement mechanism includes a rotation mechanism configured to integrally rotate the illumination system and the photography system about the optical axis of the illumination system,
the photography system acquires the plurality of images when the illumination system and the photography system are arranged in a first rotation position,
the photography system acquires an image of the anterior segment onto which the slit light is being projected by the illumination system when the illumination system and the photography system are arranged in a second rotation position different from the first rotation position, and
the three dimensional image constructing processor includes an image position determining processor configured to determine relative positions of the plurality of images based on the image acquired in the second rotation position.

8. The slit lamp microscope of claim 1, wherein the illumination system and the photography system are configured in such a manner that at least a region defined by an anterior corneal surface and a posterior crystalline lens surface is in focus of the photography system.

9. The slit lamp microscope of claim 1, wherein
the illumination system projects the slit light whose longitudinal direction corresponds to a body axis direction of a subject, onto the anterior segment, and
the movement mechanism moves the illumination system and the photography system in a direction orthogonal to the body axis direction.

10. The slit lamp microscope of claim 9, wherein
a length of the slit light is equal to or greater than a corneal diameter in the body axis direction, and
a distance of the movement of the illumination system and the photography system performed by the movement mechanism is equal to or greater than a corneal diameter in the direction orthogonal to the body axis direction.

11. The slit lamp microscope of any of claim 1, wherein the optical system of the photography system includes:
a reflector configured to reflect the light coming from the anterior segment onto which the slit light is being projected and traveling in a direction away from the optical axis of the illumination system, toward a direction approaching the optical axis of the illumination system; and
at least one lens configured to form an image of the light reflected by the reflector on the light detecting plane.

12. The slit lamp microscope of claim 1, further comprising a three dimensional image constructing processor configured to construct a three dimensional image based on the plurality of images acquired by the photography system.

13. The slit lamp microscope of claim 1, further comprising a moving image photography system configured to acquire a moving image of the anterior segment from a fixed position in parallel with acquisition of the plurality of images by the photography system.

14. An ophthalmic system comprising the slit lamp microscope of claim 1, and an information processing apparatus that is connected to the slit lamp microscope via a communication channel and processes an image of an anterior segment of an eye acquired by the slit lamp microscope.

* * * * *